United States Patent
Abou-Gharbia et al.

(10) Patent No.: US 11,873,267 B2
(45) Date of Patent: Jan. 16, 2024

(54) FUNCTIONALIZED N,N-DIALKYLAMINO PHENYL ETHERS AND THEIR METHOD OF USE

(71) Applicant: Temple University-Of The Commonwealth System of Higher Education, Philadelphia, PA (US)

(72) Inventors: Magid A. Abou-Gharbia, Exton, PA (US); Wayne E. Childers, New Hope, PA (US); Marlene A. Jacobson, Melrose Park, PA (US); Rong Fan, Philadelphia, PA (US); Rogelio L. Martinez, Trenton, NJ (US)

(73) Assignee: Temple University-Of The Commonwealth System of Higher Education, Philadelphia, PA (US)

( * ) Notice: Subject to any disclaimer, the term of this patent is extended or adjusted under 35 U.S.C. 154(b) by 788 days.

(21) Appl. No.: 16/303,723

(22) PCT Filed: May 24, 2017

(86) PCT No.: PCT/US2017/034143
§ 371 (c)(1),
(2) Date: Nov. 21, 2018

(87) PCT Pub. No.: WO2017/205451
PCT Pub. Date: Nov. 30, 2017

(65) Prior Publication Data
US 2020/0392073 A1 Dec. 17, 2020

Related U.S. Application Data

(60) Provisional application No. 62/340,779, filed on May 24, 2016.

(51) Int. Cl.
| | |
|---|---|
| *C07C 255/50* | (2006.01) |
| *A61P 33/00* | (2006.01) |
| *A61P 3/00* | (2006.01) |
| *A61K 9/00* | (2006.01) |
| *C07C 217/18* | (2006.01) |
| *C07C 217/48* | (2006.01) |

(52) U.S. Cl.
CPC .......... *C07C 255/50* (2013.01); *A61K 9/0053* (2013.01); *A61P 3/00* (2018.01); *A61P 33/00* (2018.01); *C07C 217/18* (2013.01); *C07C 217/48* (2013.01)

(58) Field of Classification Search
CPC ... C07C 255/50; C07C 217/18; C07C 217/48; C07C 2601/02; C07C 217/00; C07C 217/80; A61K 9/0053; A61P 3/00; A61P 33/00; C07D 201/00
See application file for complete search history.

(56) References Cited

U.S. PATENT DOCUMENTS

| 5,192,525 A | 3/1993 | Yang |
| 8,399,525 B2 | 3/2013 | Lockhart |
| 2008/0085874 A1 | 4/2008 | Kushner |

FOREIGN PATENT DOCUMENTS

| GB | 905903 | * | 9/1962 |
| JP | H09315977 A | | 12/1997 |

OTHER PUBLICATIONS

Caplus (Caplus Accession No. 1967:508440). Published 1967.*
Hiyama et al. (CAPLUS Abstract 1963:454659 of JP 37011677 Publ. Aug. 21, 1962).*
Lloyd-Evans, E. et al., "Niemann-Pick disease type C1 is a sphingosine storage disease that causes deregulation of lysosomal calcium", Nat. Med., 2008,14:1247-1255.
Te Vruchte, D. et al., "Measuring relative lysosomal vol. for monitoring lysosomal storage diseases", Methods Cell Biol., 2015, 126:331-347.
Liu, Y. (2016) "Design and Synthesis of MC210150 Derivatives", Bachelor's Thesis, Temple University, Philadelphia PA (17 pages).
Berg, T.O. et al., "Use of glycyl-L-phenylalanin 2-napthylamide, a lysosome-disrupting capthepsin C substrate to distinguish between lysosomes and prelysosomal endocytic vacuoles", Biochem. J., 1994, 300:229-236.
De la Mata, M. et al., "Pharmacological chaperones and Coenzyme Q10 treatment improves mutant β-Glucocerebrosidase activity and mitochondrial function in neuronopathic forms of Gaucher Disease", Sci. Rep., 2015, 5:10903 (18 pages).
Desnick, R. J. et al., "Enzyme replacement and enhancement therapies: lessons from lysosomal disorders," Nat Rev. Genet., 2002, 3:954-966.
Hardcastle, I.R. et al., "Rationally designed analogs of tamoxifen with improved calmodulin antagonism", J. Med. Chem., 1995, 38:241-248.
Jeyakumar, M. et al., "Storage solutions: Treating lysosomal disorders of the brain," Nat. Rev. Neuro., 2005, 6:1-12.
Kilpatrick, B. S. et al., "Endoplasmic reticulum and lysosomal Ca+2 stores are remodeled in GBA1-Linked Parkinson's disease and patient fibroblasts", Cell Calcium, 2016, 59:12-20.
Koltun, E. et al., "Discovery of a new class of glucosylceramide synthase inhibitors," Bioorg. Med. Chem. Lett., 2011, 21: 6773-6777.
Larsen, S. D. et al., "Property-based design of glucosylceramide synthase inhibitor that reduces glucosylceramide in the brain," J. Lipid Res., 2012, 53:282-291.
Lloyd-Evans, E. et al., "Lysosomal Ca(2+) homeostasis: role in pathogenesis of lysosomal storage diseases," Cell Calcium, 2011, 50:200-205.

(Continued)

*Primary Examiner* — Robert H Havlin
(74) *Attorney, Agent, or Firm* — Riverside Law LLP

(57) ABSTRACT

Pharmaceutical compositions of the invention comprise functionalized N,N-dialkylamino phenyl ethers derivatives having a disease-modifying action in the treatment of diseases associated with lysosomal storage dysfunction that include Gaucher's disease, and any disease or condition involving lysosomal storage dysfunction.

13 Claims, 3 Drawing Sheets

(56) References Cited

OTHER PUBLICATIONS

Lloyd-Evans, E. et al., "Niemann-Pick disease type C1 is a sphingosine storage disease that causes deregulation of lysosomal calcium," Nat. Med., 2008,14: 1247-55.

Massa, S. et al., "Antifungal agents. 1. Synthesis and antifungal activities of estrogen-like imidazole and triazole derivatives", Eur. J. Med. Chem., 1992, 27:495-502.

Meegan et al., "Flexible Estrogen Receptor Modulators: Design, Synthesis, and Antagonistic Effects in Human MCF-7 Breast Cancer Cells", Journal of Medicinal Chemistry, (Mar. 6, 2001), vol. 44, No. 7, pp. 1072-1084, XP002215447.

Meikle, P.J. et al., "Prevalence of lysosomal storage diseases", JAMA, 1999, 281:249-254.

Migdalska-Richards, A. et al., "The relationship between glucocerebrosidase mutations and Parkinson disease", J. Neurochem., 2016, 139:77-90.

Morgan, A. J. et al., "Molecular mechanism of endolysosomal Ca2+ signaling in health and disease", Biochem. J., 2011, 439:349-374.

Ogawa, K. et al., "Synthesis and antiestrogenic activity of the compounds related to the metabolites of (Z)-4-[1-[4-[2-(dimethylamino)ethoxy]-phenyl]-2-(4-isopropylphenyl)-1-butenyl]phenyl monophosphate (TAT-59)", Chem. Pharm Bull. 1991, 39:911-916.

Pubmed, U.S. National Library of Medicine, (Dec. 4, 2007), Database accession No. 18988695, XP055442573 (12 pages).

Sawkar A.R. et al., "Gaucher disease-associated glucocerebrosidases show mutation-dependent chemical chaperoning profiles", Chem. Biol., 2005, 12:1235-1244.

Sidransky, E. et al., "The link between the GBA gene and parkinsonism," Lancet Neurol, 2012, 11:986-998.

Stavber, G. et al., "Iodine induced transformations of alcohols under solvent-free conditions", Tetrahedron Lett., 2006, 47:8463-8466.

Stone, D.L. et al., "Glucocerebrosidase gene mutations in patients with type 2 Gaucher disease", Hum. Mutat., 2000, 15:181-188.

Swinney, D. C., "The Contribution of Mechanistic Understanding to Phenotypic Screening for First-in-Class Medicines Phenotypic assays in drug discovery," J. Biomol. Screen, 2013, 18:1186-1192.

Te Vruchte, D. et al., "Measuring relative lysosomal volume for monitoring lysosomal storage diseases", Methods Cell Biol., 2015, 126:331-347.

Waibel, M. et al., "Bibenzyl-and stilbene-core compounds with non-polar linker atom substituents as selective ligands for estrogen receptor beta", Eur. J. Med. Chem., 2009, 44:3412-3424.

Zheng, W. et al., "Three classes of glucocerebrosidase inhibitors identified by,quantitative high-throughput screening are chaperone leads for Gaucher disease", Proc. Natl. Acad. Sci., 2007, 104:13192-13197.

Liu, Y., "Design and Synthesis of MC210150 Derivatives", Bachelor's Thesis, Temple University, Philadelphia, PA, Published by China Pharmaceutical University Jun. 30, 2016, 17 Pages.

\* cited by examiner

FUNCTIONALIZED N,N-DIALKYLAMINO PHENYL ETHERS AND THEIR METHOD OF USE

FIELD OF INVENTION

The present invention describes novel functionalized N,N-dialkylamino phenyl ethers as well as compositions and their methods of use to prevent and/or treat lysosomal storage disorders and related conditions. The present invention further describes a novel chemotype useful for the treatment of Gaucher's disease, Tay-Sachs disease, Sandhoffs disease, Sandhoff-Jatzkewitz disease, Fabry disease, Niemann Pick disease Type C, Pompe disease, type III A mucopolysaccharidosis, Sanfilippo syndrome, α-mannosidosis, GM1 gangliosidosis, GM2 gangliosidosis, and other diseases that involve dysfunction of lysosomal storage.

CROSS-REFERENCE TO RELATED APPLICATIONS

The present application is a 35 U.S.C. § 371 national stage patent application of International Patent Application No. PCT/US2017/034143, filed May 24, 2017, which claims priority under 35 U.S.C. § 119(e) to U.S. Provisional Patent Application No. 62/340,779, filed May 24, 2016, the contents of all of which are incorporated herein by reference in their entireties.

BACKGROUND OF THE INVENTION

Lysosomal storage disorders (LSDs) are inheritable metabolic diseases with deficiencies in enzymes that function within the glycosphingolipid biosynthetic and metabolic pathway. As a consequence, non-degraded substrates accumulate and normal lysosome function is compromised, resulting in cell enlargement, impaired autophagy, disruption of cell signaling and eventually cell death. Two thirds of LSDs have central nervous system involvement resulting in a progressive neurodegeneration and the leading cause of patient death (Jeyakumar, M, Dwek, R A, Butters, T D and Platt, F M. (2005) Storage solutions: Treating lysosomal disorders of the brain, Nat Rev Neuro 6:1-12.). A group of more than 50 diseases have been classified as LSDs, including Gaucher, Tay-Sachs, Sandhoff and Fabry disease, Niemann-Pick type C and GM1 gangliosidosis. The overall prevalence is 1 in every 7700 births. With the exception of Gaucher Type 1, there are no effective treatments for these diseases. The most common lysosomal storage disorder is the autosomal recessive Gaucher disease, with a prevalence of 1 in 57,000 births (Meikle, P J, Hopwood, J J, Clauge, W F and Carery, W F. (1999) Prevalence of lysosomal storage diseases JAMA 281: 249-254.). A high carrier rate exists within Jewish populations of Eastern European decent with a corresponding incidence of 1 in 500 of affected individuals [Horowitz M. and Zimran A. (1994) Mutations causing Gaucher disease. Hum. Mutat. 3: 1-11.).

Gaucher disease is associated with a deficiency in the enzyme β-glucocerebrosidase (GCase) due to mutations of the GBA1 gene and leads to accumulation of its substrate, glucosylceramide. The most prevalent mutations are N370S and L444P. Gaucher Type 1 clinical features include hepatomegaly, splenomegaly, anemia, thrombocytopenia and bone lesions (Grabowski G A, Gaucher disease and other storage disorders. (2012) Hematology Am Soc Hematol Educ Program, 2012; 13-18.). To overcome the deficiency, enzyme replacement therapy (ERT) with administration of recombinant glucocerebrosidase (Cerezyme), has had a significant impact on the treatment of Gaucher disease (Desnick, R J and Schuchman, E H. (2002) Enzyme replacement and enhancement therapies: lessons from lysosomal disorders, Nat Rev. Genet. 3:954-966.), however its effectiveness is limited to patients with non-neuronopathic, or Type 1 Gaucher, due to the inability of the enzyme to cross the blood-brain barrier. The neuronopathic forms of Gaucher disease, associated with L444P homozygotes or compound homozygotes, are classified according to the onset and severity of disease symptoms. Type 3 (subacute juvenile or early adult onset) can begin anytime, and patients can live into early teens or adulthood. Type 2 (acute infantile onset), begins within 6 months of birth, rapidly progresses and is fatal, usually within two years of age (Grabowski G A, Gaucher disease and other storage disorders. (2012) Hematology Am Soc Hematol Educ Program, 2012; 13-18.). ERT has limited efficacy for Gaucher Type 3 disease where mild CNS symptoms are present, and for patients with Gaucher Type 2 disease and severe brain pathologies, ERT shows no efficacy. Detection by newborn screening and early treatment would improve the prognosis for these patients; however, there are no current treatment options to support testing inclusion.

The application of high throughput screening (HTS) approaches to identify small molecule treatments for LSDs has targeted specific enzymes with biochemical assays designed to either identify chaperones for the known defective enzymes (Zheng W, Padia J, Urban D J, Jadhav A, Goker-Alpan O, et al. (2007) Three classes of glucocerebrosidase inhibitors identified by quantitative high-throughput screening are chaperone leads for Gaucher disease. Proc Natl Acad Sci USA 104: 13192-13197.) and/or compounds to clear accumulating substrates resulting from decreased activity of the mutated enzyme (Koltun E, Richards S, Chan V, Nachtigall J, Du H, Noson K, Galan A, Aay N, Hanel A, Harrison A, Zhang J, Won K A, Tam D, Qian F, Wang T, Finn P, Ogilvie K, Rosen J, Mohan R, Larson C, Lamb P, Nuss J and Kearney P (2011) Discovery of a new class of glucosylceramide synthase inhibitors. Bioorg Med Chem Lett. 21: 6773-6777.). Because HTS employs chemical libraries, this strategy has the potential to identify candidates suitable for optimizing physicochemical properties to achieve therapeutic exposures in the brain and develop oral treatments for neuronopathic Gaucher disease. Eliglustat (Cerdelga™) and Miglustat (Zavesca®), compounds targeting inhibition of glucosylceramide synthase to reduce accumulating substrates, have received FDA approval, however both drugs fail to achieve CNS exposures and are limited to only treating Gaucher Type 1 (Larsen, S D, Wilson, M W, Abe, A., Shu, L, George, G H, Kirchoff, P, Hollis Showalter, H D, Xiang, J, Keep, R F and Shayman, J A. (2012) Property-based design of glucosylceramide synthase inhibitor that reduces glucosylceramide in the brain, J. Lipid Res. 53:282-291.). Another approach is to develop small molecules as chemical chaperones to assist misfolded mutant GCase and enhance stability; however, there is substantial heterogeneity within neuronopathic Gaucher disease Type 2 and a single small molecule might not function as a chaperone for all genotypes (Stone, D L, Tayebi N, Orvisky E, Stubblefield B, Madike V, and Sidransky E (2000) Glucocerebrosidase gene mutations in patients with type 2 Gaucher disease. Hum Mutat, 15:181-8. Sawkar A R, Adamski-Werner S. L., Cheng W.-C., Wong C.-H., Beutler E., Zimmer K.-P. et al. (2005) Gaucher disease-associated glucocerebrosidases show mutation-dependent chemical chaperoning profiles. Chem. Biol. 12: 1235-1244.). Moreover, the first clinical trials for a pharmacological chaperone, isofagomine, were ended due to lack of efficacy for patients with Type I Gaucher disease. There is clearly a critical need to develop new therapies to treat neuronopathic Gaucher disease and pursue alternative strategies to discover effective treatments.

The use of patient derived cells in phenotypic assays has great potential to discover new, breakthrough therapeutics and offers an alternative to target based strategies which have failed to deliver effective treatments (Swinney, D C (2013) The Contribution of Mechanistic Understanding to Phenotypic Screening for First-in-Class Medicines Phenotypic assays in drug discovery. J Biomol Screen. 18:1186-1192.). Availability of LSD patient derived cells provides a unique opportunity to develop phenotypic based screens designed to identify compounds which can either attenuate the underlying pathophysiology or restore function to a normal state to support identification of a new class of disease modifying therapeutics. Recent evidence has proposed that dysfunction of calcium signaling from acidic lysosomal stores is a common pathological feature of LSDs (Lloyd-Evans, E, Morgan A J, He X, Smith D A, Elliot-Smith E, Sillence D J, Churchill G C, Schuchman E H, Galione A, Platt F M. (2008) Niemann-Pick disease type C1 is a sphingosine storage disease that causes deregulation of lysosomal calcium. Nat Med. 14(11): 1247-55. Kilpatrick, B. S.; Magalhaes, J.; Beavan, M. S.; McNeill, A.; Gegg, M. E.; Cleeter, M. E.; Bloor-Youn, D.; Churchill, G. C.; Duchen, M. R.; Schapira, A. H.; Patel, S. Endoplasmic reticulum and lysosomal Ca+2 stores are remodeled in GBA1-Linked Parkinson's diseae and patient fibroblasts Ceel Calcium. 2015 Nov. 26, PMID 26691915, Lloyd-Evans E, Platt F M. (2011) Lysosomal Ca(2+) homeostasis: role in pathogenesis of lysosomal storage diseases. Cell Calcium. 50(2):200-205.). Calcium release from acidic stores is required in vesicle membrane fusion and transport in the endosomal/lysosomal system (Morgan, A. J.; Platt, F. M.; Lloyd-Evans, E; Galione, A. (2011) Molecular mechanism of endolysosomal Ca2+ signaling in health and disease. Biochem. J. 439:349-374.). In Niemann-Pick C (NPC) patient derived fibroblasts, a reduction in calcium release from lysosomal acidic stores was detected in response to the lysosmotic agent, Gly-Phe-β-napthylamide (GPN) in comparison with age matched normal patient cells (Lloyd-Evans, E, Morgan A J, He X, Smith D A, Elliot-Smith E, Sillence D J, Churchill G C, Schuchman E H, Galione A, Platt F M. (2008) Niemann-Pick disease type C1 is a sphingosine storage disease that causes deregulation of lysosomal calcium. Nat Med. 14(11):1247-55.). Curcumin, a compound known to increase cytosolic calcium, restored calcium signaling in NPC cells. Furthermore, curcumin treatment improved function and life expectancy in NPC1 disease mouse models ([Lloyd-Evans, E, Morgan A J, He X, Smith D A, Elliot-Smith E, Sillence D J, Churchill G C, Schuchman E H, Galione A, Platt F M. (2008) Niemann-Pick disease type C1 is a sphingosine storage disease that causes deregulation of lysosomal calcium. Nat Med. 14(11): 1247-55.). This study suggested that demonstration of a compound's calcium restorative activity on NPC cells in vitro had potential to predict in vivo efficacy in NPC animal models, and which could lead to the identification of novel therapies for NPC. In principle, the same strategy would apply to other lysosomal storage diseases such as Gaucher disease, Tay-Sachs disease, Sandhoffs diseae, Sandhoff-Jatzkewitz disease, Fabry disease, Niemann Pick disease Type C, Pompe diseae, type III A mucopolysaccharidosis, Sanfilippo syndrome, α-mannosidosis, GM1 gangliosidosis, GM2 gangliosidosis. To date, however, there are no clinically useful compounds that are capable of preventing or treating lysosomal storage diseases.

Separately, it has been observed that patients with homozygous mutations in the glucocerebrosidase (GBA1) gene have an increased risk of developing Parkinson disease (PD). The GBA1 mutation has been associated with a 20 to 30 fold increase in risk of developing PD. In addition, 7-10% of PD patients have GBA1 mutation. Mutations in the GBA1 gene constitute numerically the most important risk factor for PD (Sidransky and Lopez (2012) Lancet Neurol. 11(11): 986-998; Schapira, A; Migdalska-Richards, A. J. Neurochem. (2016), 10.1111/jnc.13385). PD patients with GBA1 mutations tend to experience an earlier onset of PD when compared to patients without the GBA1 mutation. It has been further suggested that modulation of glucocerebrosidase activity could be a novel approach to the treatment of Parkinson's disease. To date, however, there are no clinically useful treatments for PD that utilize this approach, and the availability of PD therapies is limited. There remains a clear and present need for additional therapies capable of treating and preventing Parkinson's disease. Synucleinopathies such as dementia with Lewy bodies (DLB), pure autonomic failure (PAF), and multiple system atrophy (MSA) are also unmet medical needs that could be addressed in the same manner as described for Parkinson's disease. To date, however, therapies for synucleinopathies such as dementia with Lewy bodies (DLB), pure autonomic failure (PAF), and multiple system atrophy (MSA) are not fully effective. Additional therapies are required.

Separately, fungal infection remains a serious global health issue. Cryptococcosis, for example, affects approximately 1 million people annually and kills more HIV/AIDS patients per year than tuberculosis. The gold standard therapy for cryptococcosis is amphotericin B plus 5-flucytosine, but this regimen is not readily available in regions of the world where resources are limited and where the burden of disease is highest. There is a clear and present need for additional methods and therapies capable of treating fungal infections.

BRIEF SUMMARY OF THE INVENTION

The present invention is directed toward novel functionalized N,N-dialkylamino phenyl ethers, compounds of formula (I),

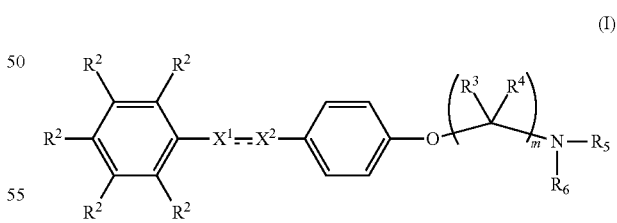

Including enantiomers, diastereomers, hydrates, solvates, pharmaceutically acceptable salts, prodrugs and complexes thereof, wherein:
The bond between $X^1$ and $X^2$ is selected from a double bond and a single bond.
When the bond between $X^1$ and $X^2$ is a single bond
$X^1$ is selected from the group consisting of $CH_2$ and $\underline{CHR^1}$
$X^2$ is selected from $CH_2$, $CHR^1$, and CO;
$X^1$ and $X^2$ are not both $CH_2$, and $X^1$ and $X^2$ are not both $CHR^1$.

When the bond between $X^1$ and $X^2$ is a double bond
  $X^1$ is selected from CH and $CR^1$
  $X^2$ is selected from CH and $CR^1$
  $X^1$ and $X^2$ are not both CH, and $X^1$ and $X^2$ are not both $CR^1$.
$R^1$ is selected from the group consisting of $C_{1-10}$ linear alkyl, $C_{3-10}$ branched alkyl, $C_{3-10}$ cycloalkyl, $C_{1-10}$ linear alkenyl, $C_{3-10}$ branched alkenyl, $C_{1-10}$ linear alkynyl, and $C_{3-10}$ branched alkynyl;
$R^2$ is at each occurrence independently selected from the group consisting of H, OH, halogen, CN, $NO_2$, $C_{1-10}$ alkoxy, $C_{3-10}$ branched alkoxy, $C_{1-10}$ haloalkoxy, $C_{3-10}$ branched haloalkoxy, $NR^7R^8$, $C(O)OR^9$, $C_{1-10}$ thioalkyl, $C_{3-10}$ branched thioalkyl, $C_{1-10}$ halothioalkyl, —$S(O)C_{1-10}$ alkyl, —$S(O)C_{3-10}$ branched alkyl, —$S(O)C_{1-10}$ haloalkyl, —$S(O)C_{3-10}$ branched haloalkyl, —$SO_2C_{1-10}$ alkyl, —$SO_2C_{3-10}$ branched alkyl, —$SO_2C_{1-10}$ haloalkyl, —$SO_2C_{3-10}$ branched haloalkyl, $SO_2NR^{10}R^{11}$, —$NR^{10}SO_2R^{12}$, $C(O)$—$NR^{10}R^{11}$;
$R^3$ is at each occurrence independently selected from the group consisting of hydrogen, $C_{1-6}$ linear alkyl, $C_{3-7}$ branched alkyl;
$R^4$ is at each occurrence independently selected from the group consisting of hydrogen, $C_{1-6}$ linear alkyl, $C_{3-7}$ branched alkyl;
m is 2, 3, 4, 5, 6, 7, 8, 9, or 10;
$R^5$ is selected from the group consisting of $C_{1-6}$ linear alkyl, $C_{3-7}$ branched alkyl;
$R^6$ is selected from the group consisting of $C_{1-6}$ linear alkyl, $C_{3-7}$ branched alkyl;
In some embodiments, $R^5$ and $R^6$ are taken together with the atoms to which they are bound to form a ring containing 4 to 7 members, optionally containing a member selected from the group consisting of O, S, and $NR^{13}$;
$R^7$ is at each occurrence independently selected from the group consisting of hydrogen, $C_{1-6}$ linear alkyl, $C_{3-7}$ branched alkyl;
$R^8$ is at each occurrence independently selected from the group consisting of hydrogen, $C_{1-6}$ linear alkyl, $C_{3-7}$ branched alkyl;
$R^9$ is at each occurrence independently selected from the group consisting of hydrogen, $C_{1-6}$ linear alkyl, $C_{3-7}$ branched alkyl;
$R^{10}$ is at each occurrence independently selected from the group consisting of hydrogen, $C_{1-6}$ linear alkyl, $C_{3-7}$ branched alkyl;
$R^{11}$ is at each occurrence independently selected from the group consisting of hydrogen, $C_{1-6}$ linear alkyl, $C_{3-7}$ branched alkyl;
$R^{12}$ is at each occurrence independently selected from the group consisting of hydrogen, $C_{1-6}$ linear alkyl, $C_{3-7}$ branched alkyl;
$R^{13}$ is at each occurrence independently selected from the group consisting of hydrogen, $C_{1-6}$ linear alkyl, $C_{3-7}$ branched alkyl.

The following compounds are specifically excluded from the scope of the markush:
1-[4-[3-(diethylamino)propoxy]phenyl]-2-phenyl-1-Propanone;
1-[4-[2-(diethylamino)ethoxy]phenyl]-2-phenyl-1-pentanone;
2-phenyl-1-[4-[2-(1-piperidinyl)ethoxy]phenyl]-1-Butanone;
1-[4-[2-(dimethylamino)ethoxy]phenyl]-2-phenyl-1-Butanone;
2-(4-aminophenyl)-1-[4-[2-(1-pyrrolidinyl)ethoxy]phenyl]-1-Butanone;
2-(4-nitrophenyl)-1-[4-[2-(1-pyrrolidinyl)ethoxy]phenyl]-1-Butanone;
1-[4-[2-(dimethylamino)ethoxy]phenyl]-2-[4-(1-methylethyl)phenyl]-1-Butanone;
4'-(2-diethylaminoethoxy)-2-phenylButyrophenone;
2-(4-bromophenyl)-1-[4-[2-(dimethylamino)ethoxy]phenyl]-1-Butanone;
1-[3,5-dibromo-4-[2-(dimethylamino)ethoxy]phenyl]-2-phenyl-1-Butanone;
2-(4-bromophenyl)-1-[4-[2-(dimethylamino)ethoxy]phenyl]-1-Butanone;
1-[4-[[6-(dimethylamino)hexyl]oxy]phenyl]-2-phenyl-1-Butanone;
1-[4-[2-(dimethylamino)ethoxy]phenyl]-2-(4-ethylphenyl)-1-Butanone;
1-[4-[2-(dimethylamino)ethoxy]phenyl]-2-(4-fluorophenyl)-1-Butanone;
1-[4-[3-(diethylamino)propoxy]phenyl]-2-phenyl-1-Butanone;
1-[4-[[5-(dimethylamino)pentyl]oxy]phenyl]-2-phenyl-1-Butanone;
2-phenyl-1-[4-[2-(1-pyrrolidinyl)ethoxy]phenyl]-1-Butanone;
1-[4-[4-(dimethylamino)butoxy]phenyl]-2-phenyl-1-Butanone;
1-[4-[2-(dimethylamino)ethoxy]phenyl]-2-(4-methylphenyl)-1-Butanone;
1-[4-[2-(diethylamino)ethoxy]phenyl]-3-methyl-2-phenyl-1-Butanone;
1-[4-[2-(diethylamino)ethoxy]phenyl]-2-phenyl-1-Butanone;
1-[4-[2-(dimethylamino)ethoxy]phenyl]-2-phenyl-1-Butanone;
4'-(2-morpholinoethoxy)-2-phenyl-Butyrophenone;
1-[4-[2-(dimethylamino)ethoxy]phenyl]-2-phenyl-1-Propanone;
2-cyclohexyl-1-[3,5-dimethyl-4-[2-(4-morpholinyl)ethoxy]phenyl]-2-phenyl-Ethanone;
N,N-dimethyl-2-[4-[(1Z)-2-phenyl-1-buten-1-yl]phenoxy]-Ethanamine;
N,N-diethyl-2-[4-[2-(4-methoxyphenyl)-1-propen-1-yl]phenoxy]-Ethanamine;
4-[(1E)-2-[4-[2-(diethylamino)ethoxy]phenyl]-1-methylethenyl]-Phenol;
4-[2-[4-[2-(diethylamino)ethoxy]phenyl]-1-methylethenyl]-Phenol;
2-[p-(p-methoxy-b-methylstyryl)phenoxy]-Triethylamine;
N,N-diethyl-3-[4-(1-methyl-2-phenylethenyl)phenoxy]-1-Propanamine;
N,N-diethyl-2-[4-[1-(phenylmethylene)propyl]phenoxy]-Ethanamine;
N,N-diethyl-2-[4-(1-methyl-2-phenylethenyl)phenoxy]-Ethanamine;
2-[p-(p-methoxy-a-methylstyryl)phenoxy]-Triethylamine;
4'-[2-(diethylamino)ethoxy]-a'-methyl-4-Stilbenol;
(E)-1-[2-[4-(1-cyclopentyl-2-phenylethenyl)phenoxy]ethyl]-Pyrrolidine;
(Z)-1-[2-[4-(1-cyclopentyl-2-phenylethenyl)phenoxy]ethyl]-Pyrrolidine;
2-[4-[1-cyclohexyl-2-(4-methoxyphenyl)ethenyl]phenoxy]-N,N-diethyl-Ethanamine;
N,N-diethyl-2-[4-[2-(4-methoxyphenyl)propyl]phenoxy]-Ethanamine;
4-[2-[4-[2-(diethylamino)ethoxy]phenyl]-1-methylethyl]-Phenol;
N,N-diethyl-3-[4-(1-methyl-2-phenylethyl)phenoxy]-1-Propanamine;

N,N-diethyl-2-[4-(1-methyl-2-phenylethyl)phenoxy]-Ethanamine;
N,N-diethyl-2-[4-[1-[(4-methoxyphenyl)methyl]propyl]phenoxy]-Ethanamine;
N,N-diethyl-2-[4-[2-(4-methoxyphenyl)-1-methylethyl]phenoxy]-Ethanamine;
4-[2-[4-[2-(diethylamino)ethoxy]phenyl]propyl]-Phenol;
and 2-[4-[1-cyclohexyl-2-(4-methoxyphenyl)ethyl]phenoxy]-N,N-diethyl-Ethanamine;

The embodiments of the present invention include compounds having formula (II):

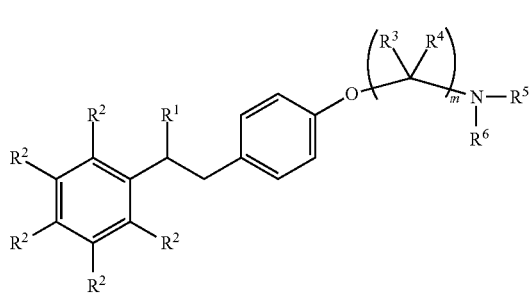

(II)

Including enantiomers, diastereomers, hydrates, solvates, enantiomers, diastereomers, pharmaceutically acceptable salts, and complexes thereof.

The embodiments of the present invention include compounds having formula (III):

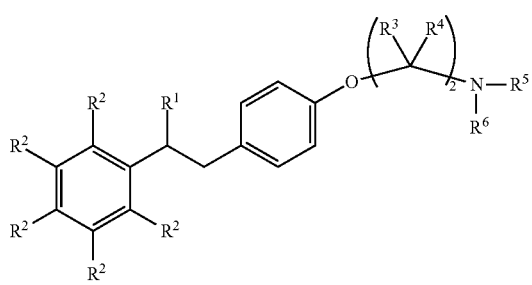

(III)

Including hydrates, solvates, enantiomers, diastereomers, pharmaceutically acceptable salts, and complexes thereof.

The embodiments of the present invention include compounds having formula (IV):

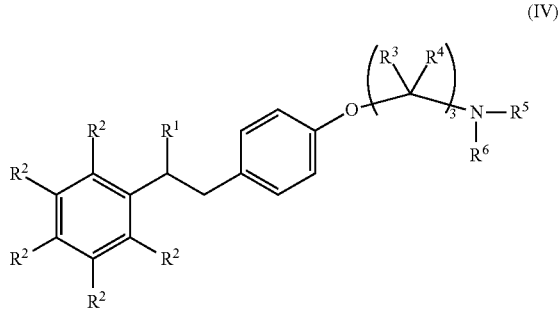

(IV)

Including hydrates, solvates, enantiomers, diastereomers, pharmaceutically acceptable salts, and complexes thereof.

The embodiments of the present invention include compounds having formula (V):

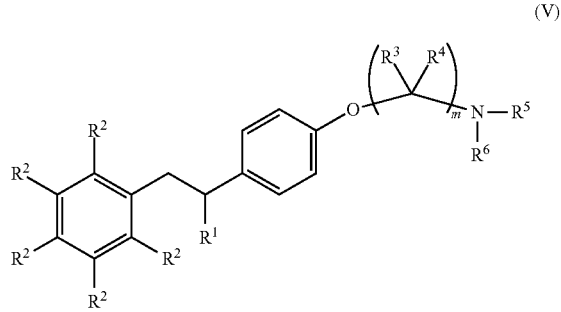

(V)

Including hydrates, solvates, enantiomers, diastereomers, pharmaceutically acceptable salts, and complexes thereof.

The embodiments of the present invention include compounds having formula (V1):

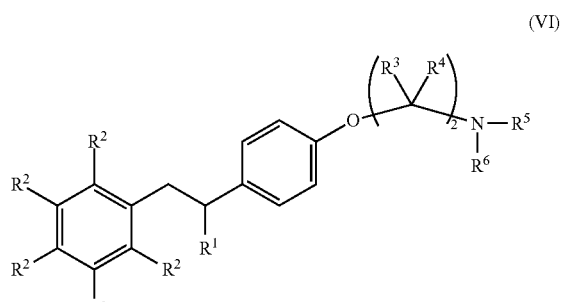

(VI)

Including hydrates, solvates, enantiomers, diastereomers, pharmaceutically acceptable salts, and complexes thereof.

The embodiments of the present invention include compounds having formula (VII):

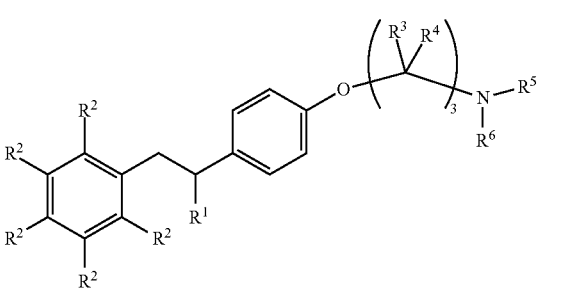

(VII)

Including hydrates, solvates, enantiomers, diastereomers, pharmaceutically acceptable salts, and complexes thereof.

The embodiments of the present invention include compounds having formula (VIII):

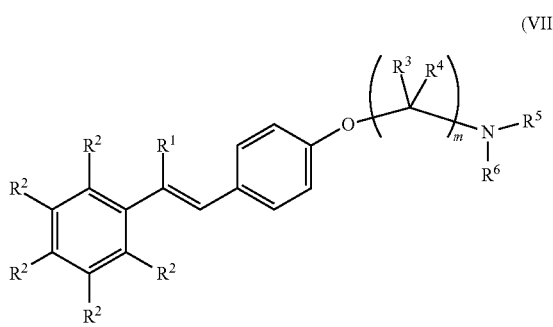

(VIII)

Including hydrates, solvates, enantiomers, diastereomers, pharmaceutically acceptable salts, and complexes thereof.

The embodiments of the present invention include compounds having formula (IX):

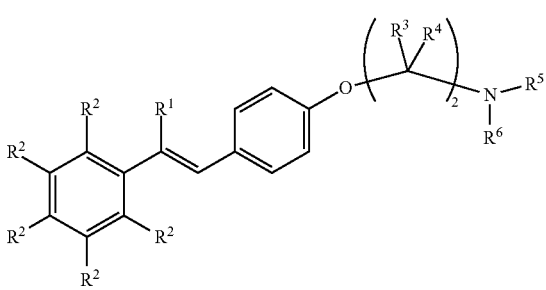

(IX)

Including hydrates, solvates, enantiomers, diastereomers, pharmaceutically acceptable salts, and complexes thereof.

The embodiments of the present invention include compounds having formula (X):

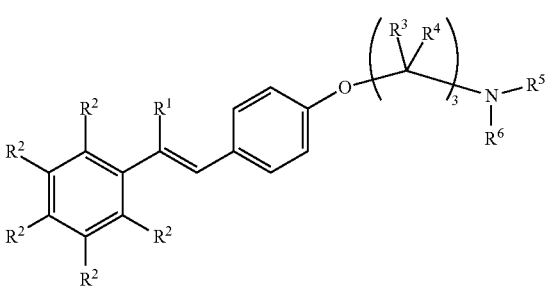

(X)

Including hydrates, solvates, enantiomers, diastereomers, pharmaceutically acceptable salts, and complexes thereof.

The embodiments of the present invention include compounds having formula (XI):

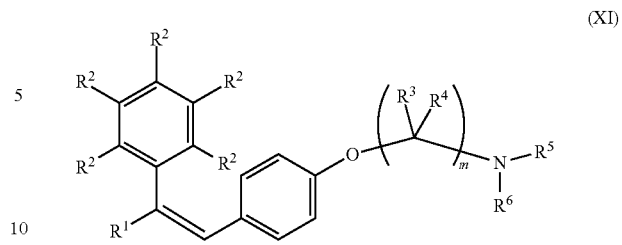

(XI)

Including hydrates, solvates, enantiomers, diastereomers, pharmaceutically acceptable salts, and complexes thereof.

The embodiments of the present invention include compounds having formula (XII):

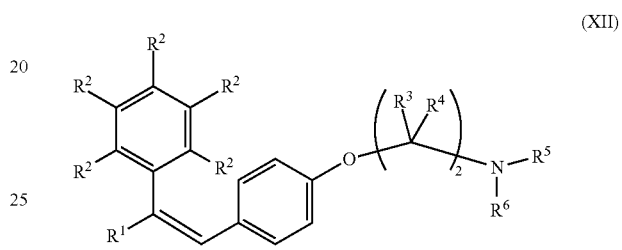

(XII)

Including hydrates, solvates, enantiomers, diastereomers, pharmaceutically acceptable salts, and complexes thereof.

The embodiments of the present invention include compounds having formula (XIII):

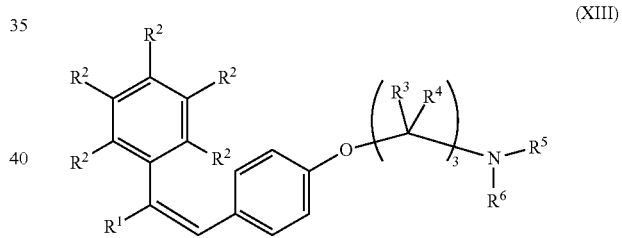

(XIII)

Including hydrates, solvates, enantiomers, diastereomers, pharmaceutically acceptable salts, and complexes thereof.

The embodiments of the present invention include compounds having formula (XIV):

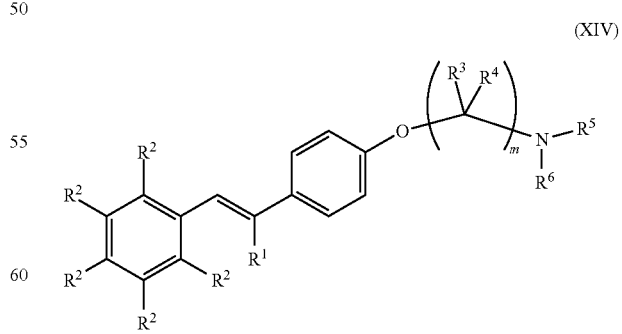

(XIV)

Including hydrates, solvates, enantiomers, diastereomers, pharmaceutically acceptable salts, and complexes thereof.

The embodiments of the present invention include compounds having formula (XV):

(XV)

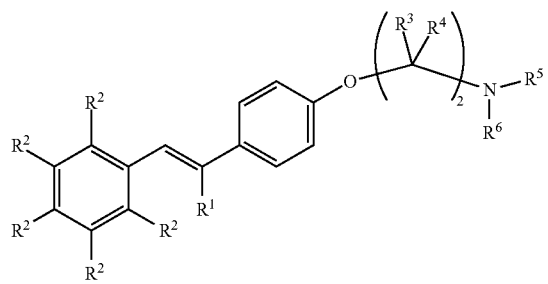

Including hydrates, solvates, enantiomers, diastereomers, pharmaceutically acceptable salts, and complexes thereof.

The embodiments of the present invention include compounds having formula (XVI):

(XVI)

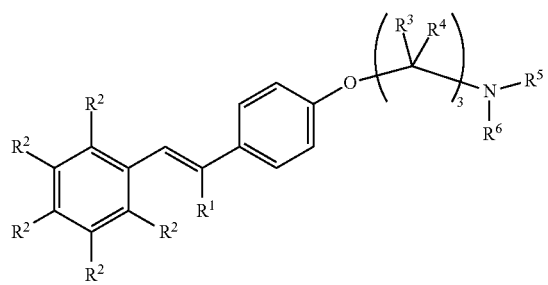

Including hydrates, solvates, enantiomers, diastereomers, pharmaceutically acceptable salts, and complexes thereof.

The embodiments of the present invention include compounds having formula (XVII):

(XVII)

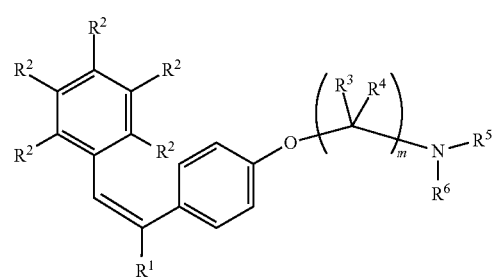

Including hydrates, solvates, enantiomers, diastereomers, pharmaceutically acceptable salts, and complexes thereof.

The embodiments of the present invention include compounds having formula (XVIII):

(XVIII)

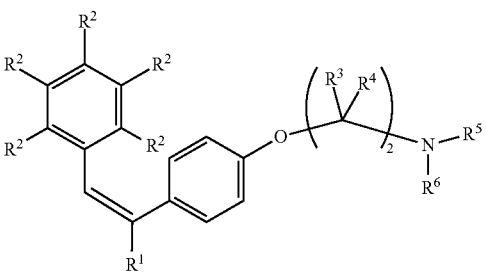

Including hydrates, solvates, enantiomers, diastereomers, pharmaceutically acceptable salts, and complexes thereof.

The embodiments of the present invention include compounds having formula (XIX):

(XIX)

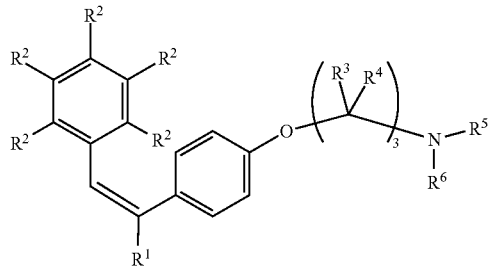

Including hydrates, solvates, enantiomers, diastereomers, pharmaceutically acceptable salts, and complexes thereof.

The embodiments of the present invention include compounds having formula (XX):

(XX)

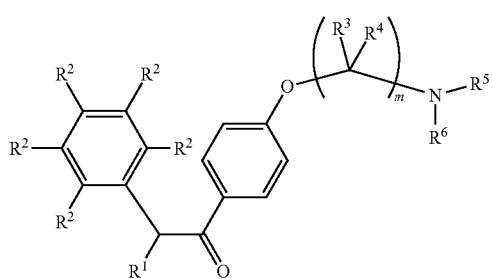

Including hydrates, solvates, enantiomers, diastereomers, pharmaceutically acceptable salts, and complexes thereof.

The embodiments of the present invention include compounds having formula (XXI):

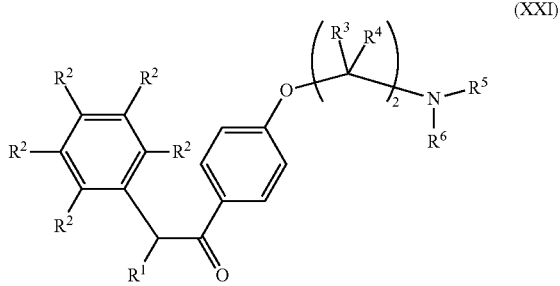

(XXI)

Including hydrates, solvates, enantiomers, diastereomers, pharmaceutically acceptable salts, and complexes thereof.

The embodiments of the present invention include compounds having formula (XXII):

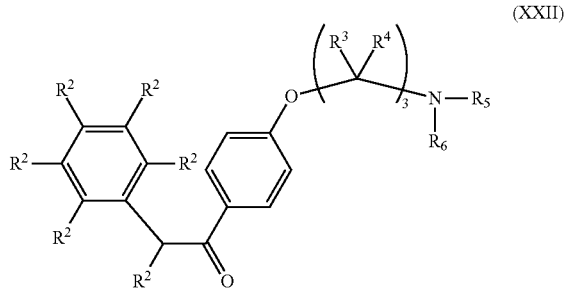

(XXII)

Including hydrates, solvates, enantiomers, diastereomers, pharmaceutically acceptable salts, and complexes thereof.

The present invention further relates to compositions comprising: an effective amount of one or more compounds according to the present invention and an excipient.

The present invention also relates to a method for treating or preventing diseases and conditions that involve lysosomal storage dysfunction, including, for example, Gaucher's disease, Tay-Sachs disease, Sandhoffs diseae, Sandhoff-Jatzkewitz disease, Fabry disease, Niemann Pick disease Type C, Pompe diseae, type III A mucopolysaccharidosis, Sanfilippo syndrome, α-mannosidosis, GM1 gangliosidosis, and GM2 gangliosidosis, said method comprising administering to a subject an effective amount of a compound or composition according to the present invention.

The present invention yet further relates to a method for treating or preventing diseases and conditions that involve lysosomal storage dysfunction, including, for example, Gaucher's disease, Tay-Sachs disease, Sandhoffs diseae, Sandhoff-Jatzkewitz disease, Fabry disease, Niemann Pick disease Type C, Pompe diseae, type III A mucopolysaccharidosis, Sanfilippo syndrome, α-mannosidosis, GM1 gangliosidosis, and GM2 gangliosidosis, wherein said method comprises administering to a subject a composition comprising an effective amount of one or more compounds according to the present invention and an excipient.

The present invention also relates to a method for treating or preventing disease or conditions associated with Gaucher's disease, Tay-Sachs disease, Sandhoffs diseae, Sandhoff-Jatzkewitz disease, Fabry disease, Niemann Pick disease Type C, Pompe diseae, type III A mucopolysaccharidosis, Sanfilippo syndrome, α-mannosidosis, GM1 gangliosidosis, and GM2 gangliosidosis, and diseases that involve lysosomal storage dysfunction. Said methods comprise administering to a subject an effective amount of a compound or composition according to the present invention.

The present invention yet further relates to a method for treating or preventing disease or conditions associated with Gaucher's disease, Tay-Sachs disease, Sandhoffs diseae, Sandhoff-Jatzkewitz disease, Fabry disease, Niemann Pick disease Type C, Pompe diseae, type III A mucopolysaccharidosis, Sanfilippo syndrome, α-mannosidosis, GM1 gangliosidosis, and GM2 gangliosidosis, and diseases that involve lysosomal storage dysfunction, wherein said method comprises administering to a subject a composition comprising an effective amount of one or more compounds according to the present invention and an excipient.

The present invention also relates to a method for treating or preventing diseases and conditions that involve misfolding of lysosomal related proteins including, for example, Gaucher's disease, Tay-Sachs disease, Sandhoffs diseae, Sandhoff-Jatzkewitz disease, Fabry disease, Niemann Pick disease Type C, Pompe diseae, type III A mucopolysaccharidosis, Sanfilippo syndrome, α-mannosidosis, GM1 gangliosidosis, and GM2 gangliosidosis, said method comprising administering to a subject an effective amount of a compound or composition according to the present invention.

The present invention also relates to a method for treating or preventing diseases and conditions that involve misfolding of lysosomal related proteins including, for example, Gaucher's disease, Tay-Sachs disease, Sandhoffs diseae, Sandhoff-Jatzkewitz disease, Fabry disease, Niemann Pick disease Type C, Pompe diseae, type III A mucopolysaccharidosis, Sanfilippo syndrome, α-mannosidosis, GM1 gangliosidosis, and GM2 gangliosidosis, said method comprising administering to a subject an effective amount of a compound or composition according to the present invention and an excipient.

The present invention yet further relates to a method for treating or preventing disease or conditions associated with Gaucher's disease, Tay-Sachs disease, Sandhoffs diseae, Sandhoff-Jatzkewitz disease, Fabry disease, Niemann Pick disease Type C, Pompe diseae, type III A mucopolysaccharidosis, Sanfilippo syndrome, α-mannosidosis, GM1 gangliosidosis, and diseases that involve misfolding of lysosomal related proteins, wherein said method comprises administering to a subject a composition comprising an effective amount of one or more compounds according to the present invention and an excipient.

The present invention also relates to a method for treating or preventing diseases and conditions that involve misfolding of lysosomal related proteins including, for example, Gaucher's disease, Tay-Sachs disease, Sandhoffs diseae, Sandhoff-Jatzkewitz disease, Fabry disease, Niemann Pick disease Type C, Pompe diseae, type III A mucopolysaccharidosis, Sanfilippo syndrome, α-mannosidosis, GM1 gangliosidosis, and GM2 gangliosidosis, said method comprising administering to a subject an effective amount of a compound or composition according to the present invention.

The present invention also relates to a method for treating or preventing Parkinson's disease. Said methods comprise administering to a subject an effective amount of a compound or composition according to the present invention.

The present invention also relates to a method for treating or preventing Parkinson's disease, wherein said methods comprise administering to a subject an effective amount of a compound or composition according to the present invention and an excipient.

The present invention also relates to a method for treating or preventing synucleinopathies such as dementia with Lewy bodies (DLB), pure autonomic failure (PAF), and multiple system atrophy (MSA). Said methods comprise administering to a subject an effective amount of a compound or composition according to the present invention.

The present invention also relates to a method for treating or preventing synucleinopathies such as dementia with Lewy bodies (DLB), pure autonomic failure (PAF), and multiple system atrophy (MSA), wherein said methods comprise administering to a subject an effective amount of a compound or composition according to the present invention and an excipient.

The present invention also relates to a method for treating or preventing disease or conditions associated with calcium signaling dysfunction. Said methods comprise administering to a subject an effective amount of a compound or composition according to the present invention.

The present invention yet further relates to a method for treating or preventing disease or conditions associated with calcium signaling dysfunction, wherein said method comprises administering to a subject a composition comprising an effective amount of one or more compounds according to the present invention and an excipient.

The present invention also relates to a method for treating or preventing disease or conditions associated with β-glucocerebrosidase dysfunction. Said methods comprise administering to a subject an effective amount of a compound or composition according to the present invention.

The present invention yet further relates to a method for treating or preventing disease or conditions associated with β-glucocerebrosidase dysfunction, wherein said method comprises administering to a subject a composition comprising an effective amount of one or more compounds according to the present invention and an excipient.

The present invention also relates to a method for treating or preventing disease or conditions associated with α-galactosidase A dysfunction. Said methods comprise administering to a subject an effective amount of a compound or composition according to the present invention.

The present invention yet further relates to a method for treating or preventing disease or conditions associated with α-galactosidase A dysfunction, wherein said method comprises administering to a subject a composition comprising an effective amount of one or more compounds according to the present invention and an excipient.

The present invention also relates to a method for treating or preventing disease or conditions associated with β-galactosidase dysfunction. Said methods comprise administering to a subject an effective amount of a compound or composition according to the present invention.

The present invention yet further relates to a method for treating or preventing disease or conditions associated with β-galactosidase dysfunction, wherein said method comprises administering to a subject a composition comprising an effective amount of one or more compounds according to the present invention and an excipient.

The present invention also relates to a method for treating or preventing disease or conditions associated with β-hexosaminidase dysfunction. Said methods comprise administering to a subject an effective amount of a compound or composition according to the present invention.

The present invention yet further relates to a method for treating or preventing disease or conditions associated with β-hexosaminidase dysfunction, wherein said method comprises administering to a subject a composition comprising an effective amount of one or more compounds according to the present invention and an excipient.

The present invention also relates to a method for treating or preventing disease or conditions associated with α-glucosidase dysfunction. Said methods comprise administering to a subject an effective amount of a compound or composition according to the present invention.

The present invention yet further relates to a method for treating or preventing disease or conditions associated with α-glucosidase dysfunction, wherein said method comprises administering to a subject a composition comprising an effective amount of one or more compounds according to the present invention and an excipient.

The present invention also relates to a method for treating or preventing disease or conditions associated with N-acetylgalactosamine-4-sulfatase dysfunction. Said methods comprise administering to a subject an effective amount of a compound or composition according to the present invention.

The present invention yet further relates to a method for treating or preventing disease or conditions associated with N-acetylgalactosamine-4-sulfatase dysfunction, wherein said method comprises administering to a subject a composition comprising an effective amount of one or more compounds according to the present invention and an excipient.

The present invention also relates to a method for treating or preventing disease or conditions associated with heparan sulfate acetyl-CoA dysfunction. Said methods comprise administering to a subject an effective amount of a compound or composition according to the present invention.

The present invention yet further relates to a method for treating or preventing disease or conditions associated with heparan sulfate acetyl-CoA dysfunction, wherein said method comprises administering to a subject a composition comprising an effective amount of one or more compounds according to the present invention and an excipient.

The present invention also relates to a method for treating or preventing disease or conditions associated with α-glucosaminidine N-acetyltransferase dysfunction. Said methods comprise administering to a subject an effective amount of a compound or composition according to the present invention.

The present invention yet further relates to a method for treating or preventing disease or conditions associated with α-glucosaminidine N-acetyltransferase dysfunction, wherein said method comprises administering to a subject a composition comprising an effective amount of one or more compounds according to the present invention and an excipient.

The present invention also relates to a method for treating or preventing disease or conditions associated with N-acetylgalactosamine-4-sulfatase dysfunction. Said methods comprise administering to a subject an effective amount of a compound or composition according to the present invention.

The present invention yet further relates to a method for treating or preventing disease or conditions associated with N-acetylgalactosamine-4-sulfatase dysfunction, wherein said method comprises administering to a subject a composition comprising an effective amount of one or more compounds according to the present invention and an excipient.

The present invention also relates to a method for treating or preventing disease or conditions associated with galactocerebrosidase dysfunction. Said methods comprise administering to a subject an effective amount of a compound or composition according to the present invention.

The present invention yet further relates to a method for treating or preventing disease or conditions associated with galactocerebrosidase dysfunction, wherein said method comprises administering to a subject a composition comprising an effective amount of one or more compounds according to the present invention and an excipient.

The present invention also relates to a method for treating or preventing disease or conditions associated with mucolipins 1 (TRPML1) dysfunction. Said methods comprise administering to a subject an effective amount of a compound or composition according to the present invention.

The present invention yet further relates to a method for treating or preventing disease or conditions associated with mucolipins 1 (TRPML1) dysfunction, wherein said method comprises administering to a subject a composition comprising an effective amount of one or more compounds according to the present invention and an excipient.

The present invention also relates to a method for treating or preventing disease or conditions associated with mucolipins 2 (TRPML2) dysfunction. Said methods comprise administering to a subject an effective amount of a compound or composition according to the present invention.

The present invention yet further relates to a method for treating or preventing disease or conditions associated with mucolipins 2 (TRPML2) dysfunction, wherein said method comprises administering to a subject a composition comprising an effective amount of one or more compounds according to the present invention and an excipient.

The present invention also relates to a method for treating or preventing disease or conditions associated with mucolipins 3 (TRPML3) dysfunction. Said methods comprise administering to a subject an effective amount of a compound or composition according to the present invention.

The present invention yet further relates to a method for treating or preventing disease or conditions associated with mucolipins 3 (TRPML3) dysfunction, wherein said method comprises administering to a subject a composition comprising an effective amount of one or more compounds according to the present invention and an excipient.

The present invention yet further relates to a method for treating or preventing fungal infections. Said methods comprise administering to a subject an effective amount of a compound or composition according to the present invention.

The present invention yet further relates to a method for treating or preventing fungal infections wherein said method comprises administering to a subject a composition comprising an effective amount of one or more compounds according to the present invention and an excipient.

The present invention further relates to a process for preparing the functionalized N,N-dialkylamino phenyl ethers of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

Figure 1:
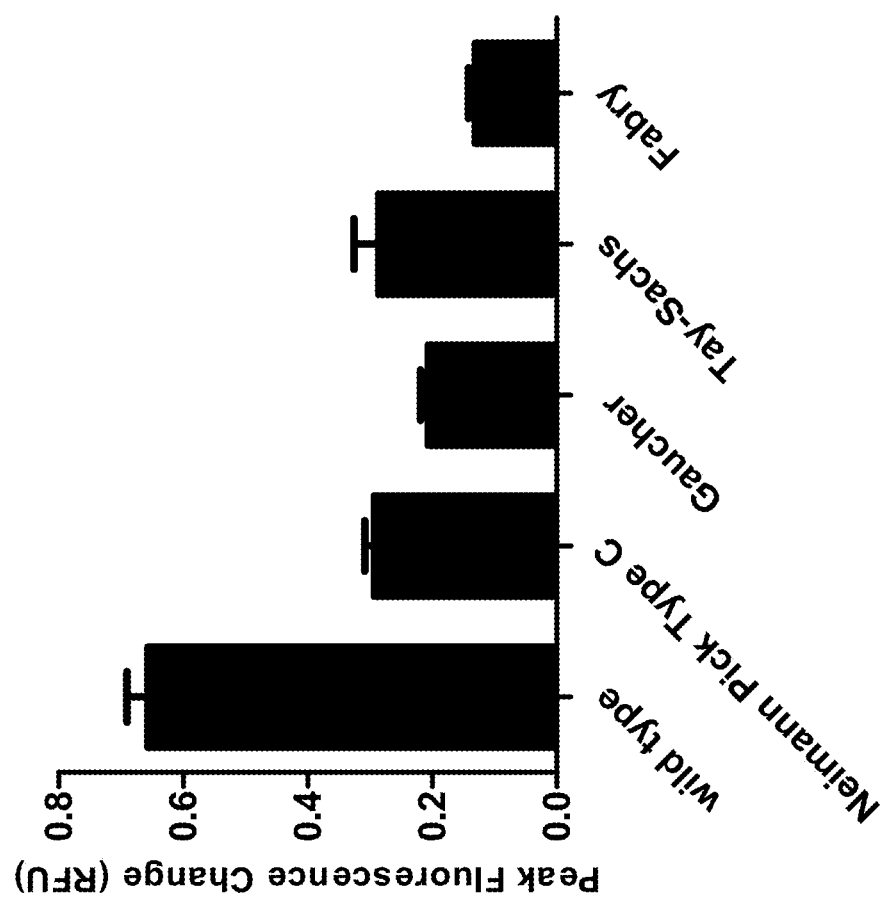
FIG. 1 is a chart depicting the reduction of calcium response to GPN in LSD patient cell lines compared with normal wildtype patient fibroblasts.

The functionalized N,N-dialkylamino phenyl ethers of the present invention and composition thereof are capable of treating and preventing diseases and conditions that involve lysosomal storage dysfunction, for example Gaucher's disease, Tay-Sachs disease, Sandhoffs diseae, Sandhoff-Jatzkewitz disease, Fabry disease, Niemann Pick disease Type C, Pompe diseae, type III A mucopolysaccharidosis, Sanfilippo syndrome, α-mannosidosis, GM1 gangliosidosis, and GM2 gangliosidosis. Further, it has been discovered that the compounds of the disclosure and compositions thereof are useful for treating or preventing disease or conditions associated with Gaucher's disease, Tay-Sachs disease, Sandhoffs diseae, Sandhoff-Jatzkewitz disease, Fabry disease, Niemann Pick disease Type C, Pompe diseae, type III A mucopolysaccharidosis, Sanfilippo syndrome, α-mannosidosis, GM1 gangliosidosis, and GM2 gangliosidosis, and diseases that involve lysosomal storage dysfunction. The compounds of the disclosure and compositions thereof are also capable of treating or preventing diseases and conditions that involve misfolding of lysosomal related proteins. The compounds of the disclosure and compositions thereof are also capable of treating or preventing diseases and conditions that are associated with misfolding of lysosomal related proteins. The compounds of the disclosure and compositions thereof are also capable of treating or preventing diseases and conditions that involve calcium signaling dysfunction. The compounds of the disclosure and compositions thereof are also capable of treating or preventing diseases and conditions that are associated with calcium signaling dysfunction.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously As used herein, the term "halogen" shall mean chlorine, bromine, fluorine and iodine.

As used herein, unless otherwise noted, "alkyl" and/or "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as ($C_{1-6}$alkyl)$_2$amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethene-2-yl), buten-4-yl, and the like. Nonlimiting examples of substituted alkenyl groups include 2-chloroethenyl (also 2-chlorovinyl), 4-hydroxybutene-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), pro-pyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —$CF_3$, —$CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as a an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylene-1-yl, naphthylene-2-yl, 4-fluorophenyl, 2-hydroxyphenyl, 3-methylphenyl, 2-amino-4-fluorophenyl, 2-(N,N-diethylamino)phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylene-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

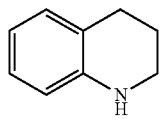

is, for the purposes of the present invention, considered a heterocyclic unit. 6,7-Dihydro-5H-cyclopentapyrimidine having the formula:

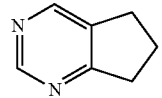

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

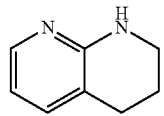

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —NO$_2$, oxo (=O), —OR$^{14}$, —SR$^{14}$, —N(R$^{14}$)$_2$, —NR$^{14}$C(O)R$^{14}$, —SO$_2$R$^{14}$, —SO$_2$OR$^{14}$, —SO$_2$N(R$^{14}$)$_2$, —C(O)R$^{14}$, —C(O)OR$^{14}$, —C(O)N(R$^{14}$)$_2$, C$_{1-6}$ alkyl, C$_{1-6}$ haloalkyl, C$_{1-6}$ alkoxy, C$_{2-8}$ alkenyl, C$_{2-8}$ alkynyl, C$_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and R$^{14}$; wherein R$^{14}$, at each occurrence, independently is hydrogen, —OR$^{15}$, —SR$^{15}$, —C(O)R$^{15}$, —C(O)OR$^{15}$, —C(O)N(R$^{15}$)$_2$, —SO$_2$R$^{15}$, —S(O)$_2$OR$^{15}$, —N(R$^{15}$)$_2$, —NR$^{15}$C(O)R$^{15}$, C$_{1-6}$ alkyl, C$_{1-6}$ haloalkyl, C$_{2-8}$ alkenyl, C$_{2-8}$ alkynyl, cycloalkyl (e.g., C$_{3-6}$ cycloalkyl), aryl, heterocycle, or heteroaryl, or two R$^{14}$ units taken together with the atom(s) to which they are bound form an optionally substituted carbocycle or heterocycle wherein said carbocycle or heterocycle has 3 to 7 ring atoms; wherein R$^{15}$, at each occurrence, independently is hydrogen, C$_{1-6}$ alkyl, C$_{1-6}$ haloalkyl, C$_{2-8}$ alkenyl, C$_{2-8}$ alkynyl, cycloalkyl (e.g., C$_{3-6}$ cycloalkyl), aryl, heterocycle, or heteroaryl, or two R$^{15}$ units taken together with the atom(s) to which they are bound form an optionally substituted carbocycle or heterocycle wherein said carbocycle or heterocycle preferably has 3 to 7 ring atoms.

In some embodiments, the substituents are selected from
i) —OR$^{16}$; for example, —OH, —OCH$_3$, —OCH$_2$CH$_3$, —OCH$_2$CH$_2$CH$_3$;
ii) —C(O)R$^{16}$; for example, —COCH$_3$, —COCH$_2$CH$_3$, —COCH$_2$CH$_2$CH$_3$;
iii) —C(O)OR$^{16}$; for example, —CO$_2$CH$_3$, —CO$_2$CH$_2$CH$_3$, —CO$_2$CH$_2$CH$_2$CH$_3$;
iv) —C(O)N(R$^{16}$)$_2$; for example, —CONH$_2$, —CONHCH$_3$, —CON(CH$_3$)$_2$;
v) —N(R$^{16}$)$_2$; for example, —NH$_2$, —NHCH$_3$, —N(CH$_3$)$_2$, —NH(CH$_2$CH$_3$);
vi) halogen: —F, —Cl, —Br, and —I;
vii) —CH$_e$X$_g$; wherein X is halogen, m is from 0 to 2, e+g=3; for example, —CH$_2$F, —CHF$_2$, —CF$_3$, —CCl$_3$, or —CBr$_3$;
viii) —SO$_2$R$^{16}$; for example, —SO$_2$H; —SO$_2$CH$_3$; —SO$_2$C$_6$H$_5$;
ix) C$_1$-C$_6$ linear, branched, or cyclic alkyl;
x) Cyano
xi) Nitro;
xii) N(R$^{16}$)C(O)R$^{16}$;
xiii) Oxo (=O);
xiv) Heterocycle; and
xv) Heteroaryl.

wherein each R$^{16}$ is independently hydrogen, optionally substituted C$_1$-C$_6$ linear or branched alkyl (e.g., optionally substituted C$_1$-C$_4$ linear or branched alkyl), or optionally substituted C$_3$-C$_6$ cycloalkyl (e.g optionally substituted C$_3$-C$_4$ cycloalkyl); or two R$^{16}$ units can be taken together to form a ring comprising 3-7 ring atoms. In certain aspects, each R$^{16}$ is independently hydrogen, C$_1$-C$_6$ linear or branched alkyl optionally substituted with halogen or C$_3$-C$_6$ cycloalkyl or C$_3$-C$_6$ cycloalkyl.

At various places in the present specification, substituents of compounds are disclosed in groups or in ranges. It is specifically intended that the description include each and every individual subcombination of the members of such groups and ranges. For example, the term "C$_{1-6}$ alkyl" is specifically intended to individually disclose C$_1$, C$_2$, C$_3$, C$_4$, C$_5$, C$_6$, C$_1$-C$_6$, C$_1$-C$_5$, C$_1$-C$_4$, C$_1$-C$_3$, C$_1$-C$_2$, C$_2$-C$_6$, C$_2$-C$_5$, C$_2$-C$_4$, C$_2$-C$_3$, C$_3$-C$_6$, C$_3$-C$_5$, C$_3$-C$_4$, C$_4$-C$_6$, C$_4$-C$_5$, and C$_5$-C$_6$, alkyl.

For the purposes of the present invention the terms "compound," "analog," and "composition of matter" stand equally well for the functionalized N,N-dialkylamino phenyl ethers described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include NaHCO$_3$, Na$_2$CO$_3$, KHCO$_3$, K$_2$CO$_3$, Cs$_2$CO$_3$, LiOH, NaOH, KOH, NaH$_2$PO$_4$, Na$_2$HPO$_4$, and Na$_3$PO$_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, naphthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in N(R$^{15}$)$_2$, each R$^{15}$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The functionalized N,N-dialkylamino phenyl ethers

The compounds of the present invention are functionalized N,N-dialkylamino phenyl ethers, and include all enantiomeric and diastereomeric forms and pharmaceutically accepted salts thereof having the formula:

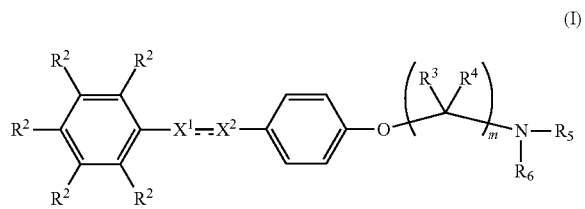

(I)

Including hydrates, solvates, pharmaceutically acceptable salts, prodrugs and complexes thereof, wherein:

The bond between $X^1$ and $X^2$ is selected from a double bond and a single bond.

When the bond between $X^1$ and $X^2$ is a single bond
  $X^1$ is selected from the group consisting of $CH_2$ and $CHR^1$
  $X^2$ is selected from $CH_2$, $CHR^1$, and CO;
  $X^1$ and $X^2$ are not both $CH_2$, and $X^1$ and $X^2$ are not both $CHR^1$.

When the bond between $X^1$ and $X^2$ is a double bond
  $X^1$ is selected from CH and $CR^1$
  $X^2$ is selected from CH and $CR^1$
  $X^1$ and $X^2$ are not both CH, and $X^1$ and $X^2$ are not both $CR^1$.

$R^1$ is selected from the group consisting of $C_{1-10}$ linear alkyl, $C_{3-10}$ branched alkyl, $C_{3-10}$ cycloalkyl, $C_{1-10}$ linear alkenyl, $C_{3-10}$ branched alkenyl, $C_{1-10}$ linear alkynyl, and $C_{3-10}$ branched alkynyl;

$R^2$ is at each occurrence independently selected from the group consisting of H, OH, halogen, CN, $NO_2$, $C_{1-10}$ alkoxy, $C_{3-10}$ branched alkoxy, $C_{1-10}$ haloalkoxy, $C_{3-10}$ branched haloalkoxy, $NR^7R^8$, $C(O)OR^9$, $C_{1-10}$ thioalkyl, $C_{3-10}$ branched thioalkyl, $C_{1-10}$ halothioalkyl, —$S(O)C_{1-10}$ alkyl, —$S(O)C_{3-10}$ branched alkyl, —$S(O)C_{1-10}$ haloalkyl, —$S(O)C_{3-10}$ branched haloalkyl, —$SO_2C_{1-10}$ alkyl, —$SO_2C_{3-10}$ branched alkyl, —$SO_2C_{1-10}$ haloalkyl, —$SO_2C_{3-10}$ branched haloalkyl, $SO_2NR^{10}R^{11}$, —$NR^{10}SO_2R^{12}$, $C(O)$—$NR^{10}R^{11}$;

$R^3$ is at each occurrence independently selected from the group consisting of hydrogen, $C_{1-6}$ linear alkyl, $C_{3-7}$ branched alkyl;

$R^4$ is at each occurrence independently selected from the group consisting of hydrogen, $C_{1-6}$ linear alkyl, $C_{3-7}$ branched alkyl;

m is 2, 3, 4, 5, 6, 7, 8, 9, or 10;

$R^5$ is selected from the group consisting of $C_{1-6}$ linear alkyl, $C_{3-7}$ branched alkyl;

$R^6$ is selected from the group consisting of $C_{1-6}$ linear alkyl, $C_{3-7}$ branched alkyl;

In some embodiments, $R^5$ and $R^6$ are taken together with the atoms to which they are bound to form a ring containing 4 to 7 members, optionally containing a member selected from the group consisting of 0, S, and $NR^{13}$ $R^7$ is at each occurrence independently selected from the group consisting of hydrogen, $C_{1-6}$ linear alkyl, $C_{3-7}$ branched alkyl;

$R^8$ is at each occurrence independently selected from the group consisting of hydrogen, $C_{1-6}$ linear alkyl, $C_{3-7}$ branched alkyl;

$R^9$ is at each occurrence independently selected from the group consisting of hydrogen, $C_{1-6}$ linear alkyl, $C_{3-7}$ branched alkyl;

$R^{10}$ is at each occurrence independently selected from the group consisting of hydrogen, $C_{1-6}$ linear alkyl, $C_{3-7}$ branched alkyl;

$R^{11}$ is at each occurrence independently selected from the group consisting of hydrogen, $C_{1-6}$ linear alkyl, $C_{3-7}$ branched alkyl;

$R^{12}$ is at each occurrence independently selected from the group consisting of hydrogen, $C_{1-6}$ linear alkyl, $C_{3-7}$ branched alkyl;

$R^{13}$ is at each occurrence independently selected from the group consisting of hydrogen, $C_{1-6}$ linear alkyl, $C_{3-7}$ branched alkyl.

The following compounds are specifically excluded from the scope of the markush:
1-[4-[3-(diethylamino)propoxy]phenyl]-2-phenyl-1-Propanone
1-[4-[2-(diethylamino)ethoxy]phenyl]-2-phenyl-1-pentanone
2-phenyl-1-[4-[2-(1-piperidinyl)ethoxy]phenyl]-1-Butanone
1-[4-[2-(dimethylamino)ethoxy]phenyl]-2-phenyl-1-Butanone
2-(4-aminophenyl)-1-[4-[2-(1-pyrrolidinyl)ethoxy]phenyl]-1-Butanone
2-(4-nitrophenyl)-1-[4-[2-(1-pyrrolidinyl)ethoxy]phenyl]-1-Butanone
1-[4-[2-(dimethylamino)ethoxy]phenyl]-2-[4-(1-methylethyl)phenyl]-1-Butanone
4'-(2-diethylaminoethoxy)-2-phenylButyrophenone
2-(4-bromophenyl)-1-[4-[2-(dimethylamino)ethoxy]phenyl]-1-Butanone
1-[3,5-dibromo-4-[2-(dimethylamino)ethoxy]phenyl]-2-phenyl-1-Butanone
2-(4-bromophenyl)-1-[4-[2-(dimethylamino)ethoxy]phenyl]-1-Butanone
1-[4-[[6-(dimethylamino)hexyl]oxy]phenyl]-2-phenyl-1-Butanone
1-[4-[2-(dimethylamino)ethoxy]phenyl]-2-(4-ethylphenyl)-1-Butanone
1-[4-[2-(dimethylamino)ethoxy]phenyl]-2-(4-fluorophenyl)-1-Butanone
1-[4-[3-(diethylamino)propoxy]phenyl]-2-phenyl-1-Butanone 1-[4-[[5-(dimethylamino)pentyl]oxy]phenyl]-2-phenyl-1-Butanone 2-phenyl-1-[4-[2-(1-pyrrolidinyl)ethoxy]phenyl]-1-Butanone 1-[4-[4-(dimethylamino)butoxy]phenyl]-2-phenyl-1-Butanone 1-[4-[2-(dimethylamino)ethoxy]phenyl]-2-(4-methylphenyl)-1-Butanone 1-[4-[2-(diethylamino)ethoxy]phenyl]-3-methyl-2-phenyl-1-Butanone 1-[4-[2-(diethylamino)ethoxy]phenyl]-2-phenyl-1-Butanone 1-[4-[2-(dimethylamino)ethoxy]phenyl]-2-phenyl-1-Butanone 4'-(2-morpholinoethoxy)-2-phenyl-Butyrophenone 1-[4-[2-(dimethylamino)ethoxy]phenyl]-2-phenyl-1-Propanone 2-cyclohexyl-1-[3,5-dimethyl-4-[2-(4-morpholinyl)ethoxy]phenyl]-2-phenyl-Ethanone N,N-dimethyl-2-[4-[(1Z)-2-phenyl-1-buten-1-yl]phenoxy]-Ethanamine N,N-diethyl-2-[4-[2-(4-methoxyphenyl)-1-propen-1-yl]phenoxy]-Ethanamine 4-[(1E)-2-[4-[2-(diethylamino)ethoxy]phenyl]-1-methylethenyl]-Phenol 4-[2-[4-[2-(diethylamino)ethoxy]phenyl]-1-methylethenyl]-Phenol 2-[p-(p-methoxy-b-methylstyryl)phenoxy]-Triethylamine N,N-diethyl-3-[4-(1-methyl-2-phenylethenyl)phenoxy]-1-Propanamine N,N-diethyl-2-[4-[1-(phenylmethylene)propyl]phenoxy]-Ethanamine N,N-diethyl-2-[4-(1-methyl-2-phenylethenyl)phenoxy]-Ethanamine 2-[p-(p-methoxy-a-methylstyryl)phenoxy]-Triethylamine 4'-[2-(diethylamino)ethoxy]-a'-methyl-4-Stilbenol (E)-1-[2-[4-(1-cyclopentyl-2-phenylethenyl)phenoxy]ethyl]-Pyrrolidine (Z)-1-[2-[4-(1-cyclopentyl-2-phenylethenyl)phenoxy]ethyl]-Pyrrolidine 2-[4-[1-cyclohexyl-2-(4-methoxyphenyl)ethenyl]phenoxy]-N,N-diethyl-Ethanamine N,N-diethyl-2-[4-[2-(4-methoxyphenyl)propyl]phenoxy]-Ethanamine 4-[2-[4-[2-(diethylamino)ethoxy]phenyl]-1-methylethyl]-Phenol N,N-diethyl-3-[4-(1-methyl-2-phenylethyl)phenoxy]-1-Propanamine N,N-diethyl-2-[4-(1-methyl-2-phenylethyl)phenoxy]-Ethanamine N,N-diethyl-2-[4-[1-[(4-methoxyphenyl)methyl]propyl]phenoxy]-Ethanamine N,N-diethyl-2-[4-[2-(4-methoxyphenyl)-1-methylethyl]phenoxy]-Ethanamine 4-[2-[4-[2-(diethylamino)ethoxy]phenyl]propyl]-Phenol 2-[4-[1-cyclohexyl-2-(4-methoxyphenyl)ethyl]phenoxy]-N,N-diethyl-Ethanamine The embodiments of the present invention include compounds having formula (II):

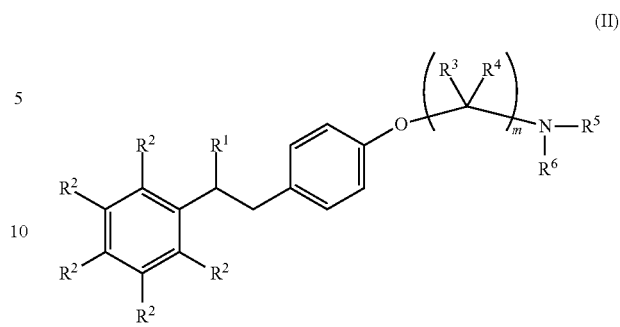

Including hydrates, solvates, enantiomers, diastereomers, pharmaceutically acceptable salts, and complexes thereof.

The embodiments of the present invention include compounds having formula (III):

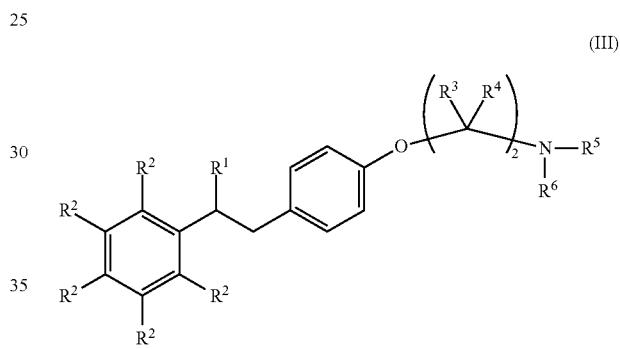

Including hydrates, solvates, enantiomers, diastereomers, pharmaceutically acceptable salts, and complexes thereof.

The embodiments of the present invention include compounds having formula (IV):

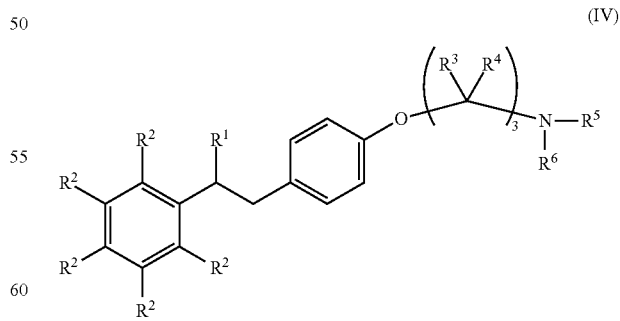

Including hydrates, solvates, enantiomers, diastereomers, pharmaceutically acceptable salts, and complexes thereof.

The embodiments of the present invention include compounds having formula (V):

(V)

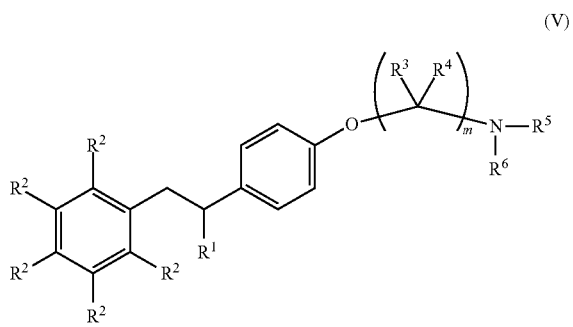

Including hydrates, solvates, enantiomers, diastereomers, pharmaceutically acceptable salts, and complexes thereof.

The embodiments of the present invention include compounds having formula (V1):

(VI)

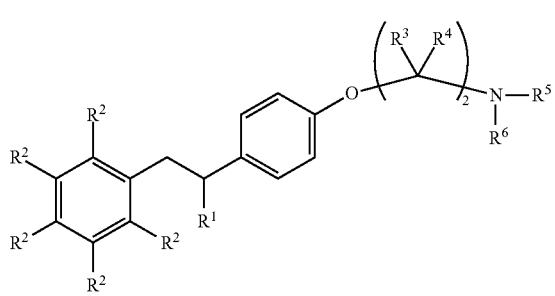

Including hydrates, solvates, enantiomers, diastereomers, pharmaceutically acceptable salts, and complexes thereof.

The embodiments of the present invention include compounds having formula (VII):

(VII)

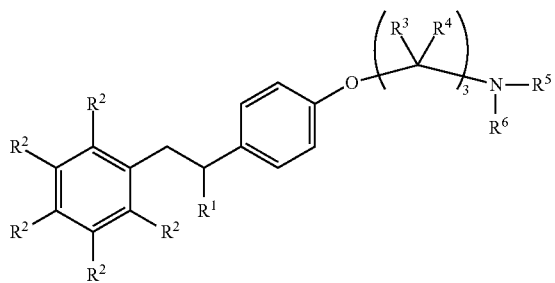

Including hydrates, solvates, enantiomers, diastereomers, pharmaceutically acceptable salts, and complexes thereof.

The embodiments of the present invention include compounds having formula (VIII):

(VIII)

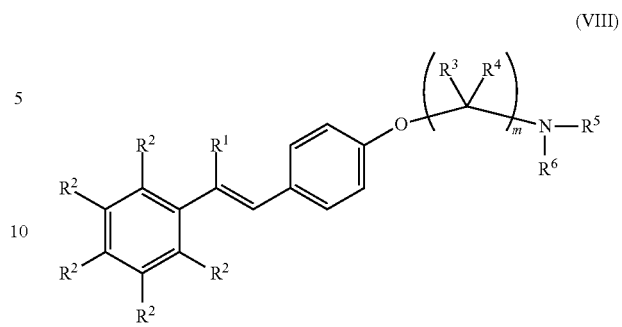

Including hydrates, solvates, enantiomers, diastereomers, pharmaceutically acceptable salts, and complexes thereof.

The embodiments of the present invention include compounds having formula (IX):

(IX)

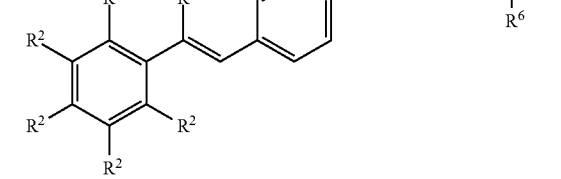

Including hydrates, solvates, enantiomers, diastereomers, pharmaceutically acceptable salts, and complexes thereof.

The embodiments of the present invention include compounds having formula (X):

(X)

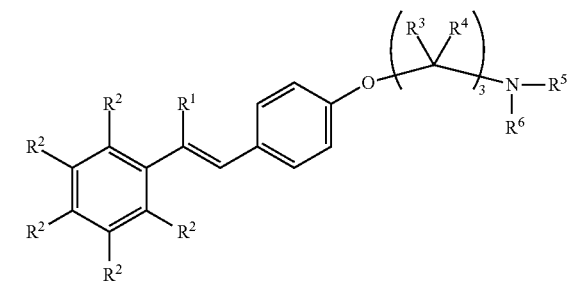

Including hydrates, solvates, enantiomers, diastereomers, pharmaceutically acceptable salts, and complexes thereof.

The embodiments of the present invention include compounds having formula (XI):

(XI)

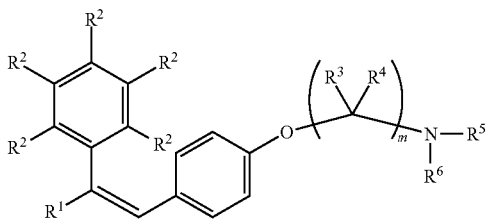

Including hydrates, solvates, enantiomers, diastereomers, pharmaceutically acceptable salts, and complexes thereof.

The embodiments of the present invention include compounds having formula (XII):

(XII)

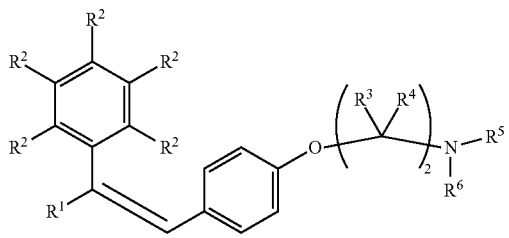

Including hydrates, solvates, enantiomers, diastereomers, pharmaceutically acceptable salts, and complexes thereof.

The embodiments of the present invention include compounds having formula (XIII):

(XIII)

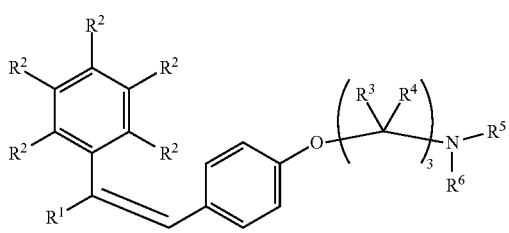

Including hydrates, solvates, enantiomers, diastereomers, pharmaceutically acceptable salts, and complexes thereof.

The embodiments of the present invention include compounds having formula (XIV):

(XIV)

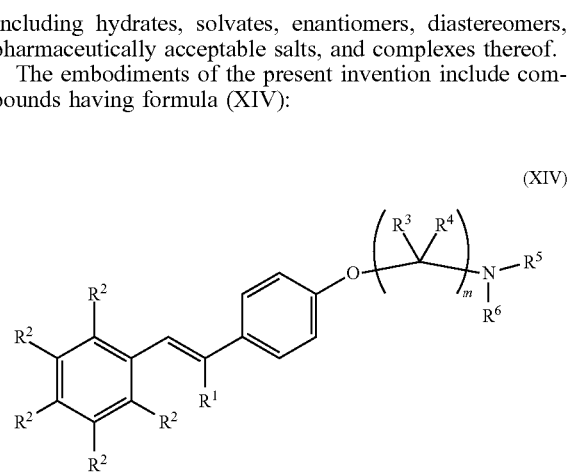

Including hydrates, solvates, enantiomers, diastereomers, pharmaceutically acceptable salts, and complexes thereof.

The embodiments of the present invention include compounds having formula (XV):

(XV)

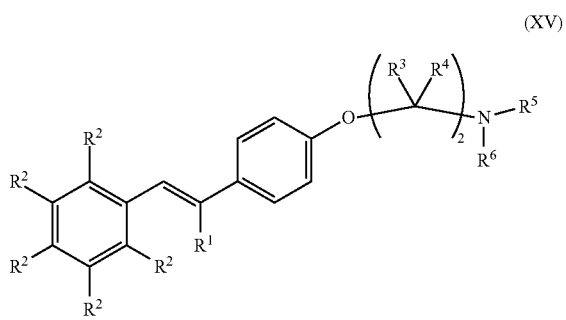

Including hydrates, solvates, enantiomers, diastereomers, pharmaceutically acceptable salts, and complexes thereof.

The embodiments of the present invention include compounds having formula (XVI):

(XVI)

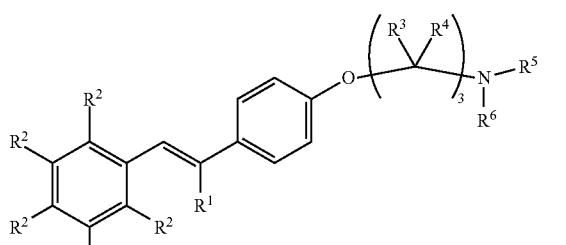

Including hydrates, solvates, enantiomers, diastereomers, pharmaceutically acceptable salts, and complexes thereof.

The embodiments of the present invention include compounds having formula (XVII):

(XVII)

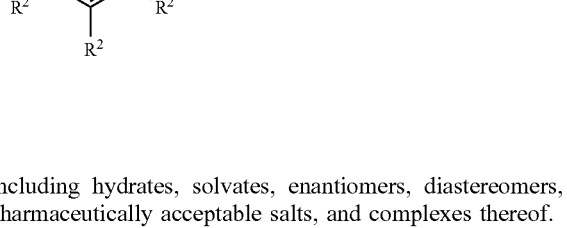

Including hydrates, solvates, enantiomers, diastereomers, pharmaceutically acceptable salts, and complexes thereof.

The embodiments of the present invention include compounds having formula (XVIII):

(XVIII)

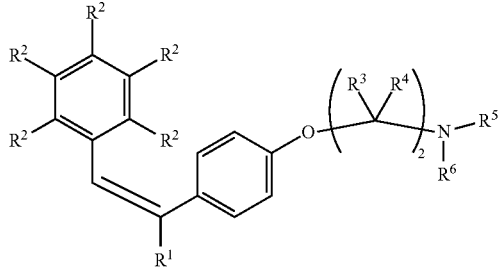

Including hydrates, solvates, enantiomers, diastereomers, pharmaceutically acceptable salts, and complexes thereof.

The embodiments of the present invention include compounds having formula (XIX):

(XIX)

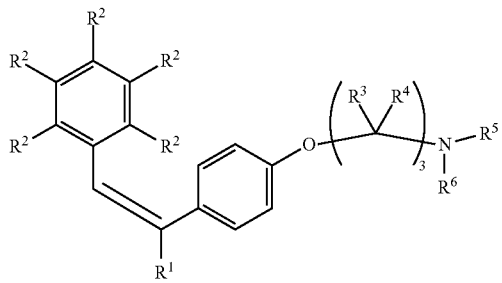

Including hydrates, solvates, enantiomers, diastereomers, pharmaceutically acceptable salts, and complexes thereof.

The embodiments of the present invention include compounds having formula (XX):

(XX)

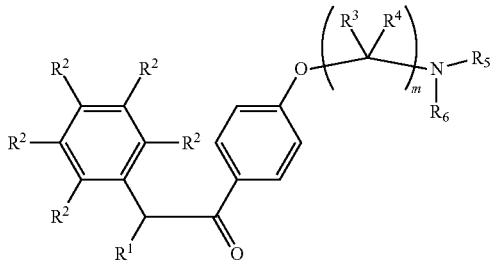

Including hydrates, solvates, enantiomers, diastereomers, pharmaceutically acceptable salts, and complexes thereof.

The embodiments of the present invention include compounds having formula (XXI):

(XXI)

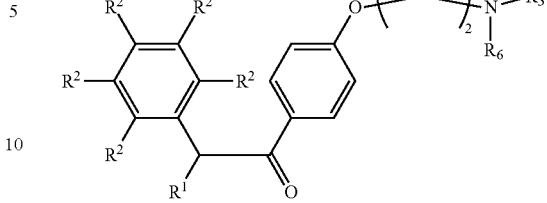

Including hydrates, solvates, enantiomers, diastereomers, pharmaceutically acceptable salts, and complexes thereof.

The embodiments of the present invention include compounds having formula (XXII):

(XXII)

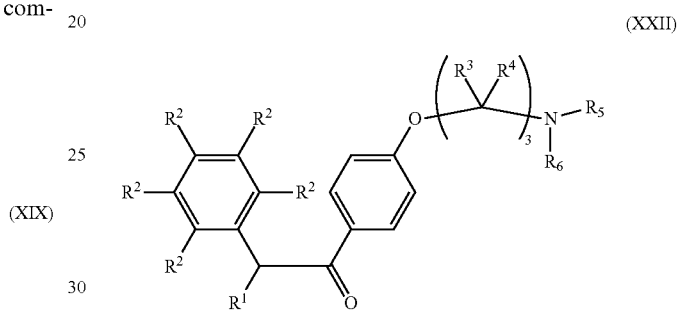

Including hydrates, solvates, enantiomers, diastereomers, pharmaceutically acceptable salts, and complexes thereof.

In some embodiments $X^1$ is $CH_2$.
In some embodiments $X^1$ is $CR^1$.
In some embodiments $X^2$ is $CH_2$.
In some embodiments $X^2$ is $CR^1$.
In some embodiments $X^2$ is CO.
In some embodiments the bond between $X^1$ and $X^2$ is a single bond.
In some embodiments the bond between $X^1$ and $X^2$ is a double bond.
In some embodiments $R^1$ is $C_{1-10}$ linear alkyl.
In some embodiments $R^1$ is $C_{3-10}$ branched alkyl.
In some embodiments $R^1$ is $C_{3-10}$ cycloalkyl.
In some embodiments $R^1$ is $C_{1-10}$ linear alkenyl.
In some embodiments $R^1$ is $C_{3-10}$ branched alkenyl.
In some embodiments $R^1$ is $C_{1-10}$ linear alkynyl.
In some embodiments $R^1$ is $C_{3-10}$ branched alkynyl.
In some embodiments $R^2$ is H.
In some embodiments $R^2$ is OH.
In some embodiments $R^2$ is halogen.
In some embodiments $R^2$ is CN.
In some embodiments $R^2$ is $NO_2$.
In some embodiments $R^2$ is $C_{1-10}$ alkoxy.
In some embodiments $R^2$ is $C_{3-10}$ branched alkoxy.
In some embodiments $R^2$ is $C_{1-10}$ haloalkoxy.
In some embodiments $R^2$ is $C_{3-10}$ branched haloalkoxy.
In some embodiments $R^2$ is $NR^7R^8$.
In some embodiments $R^2$ is $C(O)OR^9$.
In some embodiments $R^2$ is $C_{1-10}$ thioalkyl.
In some embodiments $R^2$ is $C_{3-10}$ branched thioalkyl.
In some embodiments $R^2$ is $C_{1-10}$ halothioalkyl.
In some embodiments $R^2$ is —$S(O)C_{1-10}$ alkyl.
In some embodiments $R^2$ is —$S(O)C_{3-10}$ branched alkyl.
In some embodiments $R^2$ is —$S(O)C_{1-10}$ haloalkyl.

In some embodiments $R^2$ is —S(O)$C_{3-10}$ branched haloalkyl.
In some embodiments $R^2$ is —$SO_2C_{1-10}$ alkyl.
In some embodiments $R^2$ is —$SO_2C_{3-10}$ branched alkyl.
In some embodiments $R^2$ is —$SO_2C_{1-10}$ haloalkyl.
In some embodiments $R^2$ is —$SO_2C_{3-10}$ branched haloalkyl.
In some embodiments $R^2$ is $SO_2NR^{10}R^{11}$.
In some embodiments $R^2$ is —$NR^{10}SO_2R^{12}$.
In some embodiments $R^2$ is C(O)—$NR^{10}R^{11}$.
In some embodiments $R^3$ is hydrogen.
In some embodiments $R^3$ is $C_{1-6}$ linear alkyl.
In some embodiments $R^3$ is $C_{3-7}$ branched alkyl.
In some embodiments $R^4$ is hydrogen.
In some embodiments $R^4$ is $C_{1-6}$ linear alkyl.
In some embodiments $R^4$ is $C_{3-7}$ branched alkyl.
In some embodiments $R^5$ is $C_{1-6}$ linear alkyl.
In some embodiments $R^5$ is, $C_{3-7}$ branched alkyl.
In some embodiments $R^6$ is $C_{1-6}$ linear alkyl.
In some embodiments $R^6$ is $C_{3-7}$ branched alkyl.
In some embodiments $R^5$ and $R^6$ are taken together with the atoms to which they are bound to form a ring containing 4 members, optionally containing a member selected from the group consisting of O, S, and $NR^{13}$.
In some embodiments $R^5$ and $R^6$ are taken together with the atoms to which they are bound to form a ring containing 5 members, optionally containing a member selected from the group consisting of O, S, and $NR^{13}$.
In some embodiments $R^5$ and $R^6$ are taken together with the atoms to which they are bound to form a ring containing 6 members, optionally containing a member selected from the group consisting of O, S, and $NR^{13}$.
In some embodiments $R^5$ and $R^6$ are taken together with the atoms to which they are bound to form a ring containing 7 members, optionally containing a member selected from the group consisting of O, S, and $NR^{13}$.
In some embodiments $R^7$ is hydrogen.
In some embodiments $R^7$ is $C_{1-6}$ linear alkyl.
In some embodiments $R^7$ is $C_{3-7}$ branched alkyl.
In some embodiments $R^8$ is hydrogen.
In some embodiments $R^8$ is $C_{1-6}$ linear alkyl.
In some embodiments $R^8$ is $C_{3-7}$ branched alkyl.
In some embodiments $R^9$ is hydrogen.
In some embodiments $R^9$ is $C_{1-6}$ linear alkyl.
In some embodiments $R^9$ is $C_{3-7}$ branched alkyl.
In some embodiments $R^{10}$ is hydrogen.
In some embodiments $R^{10}$ is $C_{1-6}$ linear alkyl.
In some embodiments $R^{10}$ is $C_{3-7}$ branched alkyl.
In some embodiments $R^{11}$ is hydrogen.
In some embodiments $R^{11}$ is $C_{1-6}$ linear alkyl.
In some embodiments $R^{11}$ is $C_{3-7}$ branched alkyl.
In some embodiments $R^{12}$ is hydrogen.
In some embodiments $R^{12}$ is $C_{1-6}$ linear alkyl.
In some embodiments $R^{12}$ is $C_{3-7}$ branched alkyl.
In some embodiments $R^{13}$ is hydrogen.
In some embodiments $R^{13}$ is $C_{1-6}$ linear alkyl.
In some embodiments $R^{13}$ is $C_{3-7}$ branched alkyl.
In some embodiments m is 2.
In some embodiments m is 3.
In some embodiments m is 4.
In some embodiments m is 5.
In some embodiments m is 6.
In some embodiments m is 7.
In some embodiments m is 8.
In some embodiments m is 9.
In some embodiments m is 10.

For the purposes of demonstrating the manner in which the compounds of the present invention are named and referred to herein, the compound having the formula:

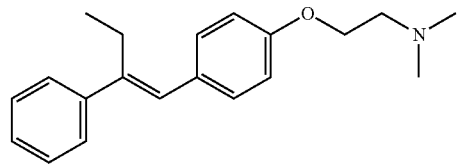 [SMILES: CC/C(=C\c1ccc(OCCN(C)C)cc1)c1ccccc1]

has the chemical name (E)-N,N-Dimethyl-2-(4-(2-(phenyl) but-1-en-1-yl)phenoxy)ethan-1-amine.

For the purposes of demonstrating the manner in which the compounds of the present invention are named and referred to herein, the compound having the formula:

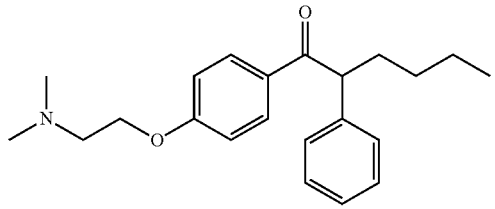

has the chemical name 1-(4-(2-(Dimethylamino)ethoxy) phenyl)-2-phenylhexan-1-one.

For the purposes of demonstrating the manner in which the compounds of the present invention are named and referred to herein, the compound having the formula:

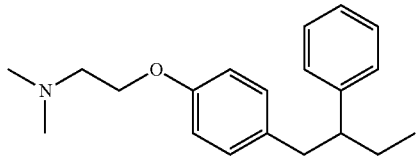 [SMILES: CCC(Cc1ccc(OCCN(C)C)cc1)c1ccccc1]

has the chemical name N,N-Dimethyl-2-(4-(2-phenylbutyl) phenoxy)ethan-1-amine.

For the purposes of the present invention, a compound depicted by the racemic formula, for example:

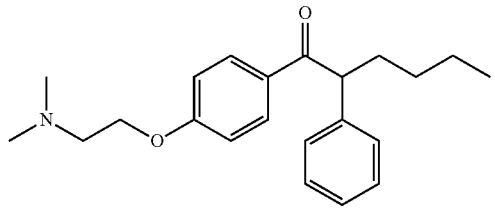

will stand equally well for either of the two enantiomers having the formula:

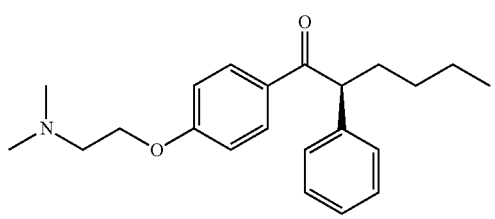 [SMILES: CCCC[C@H](C(=O)c1ccc(OCCN(C)C)cc1)c1ccccc1]

or the formula:

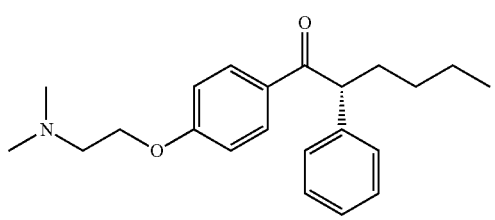 [SMILES: CCCC[C@@H](C(=O)c1ccc(OCCN(C)C)cc1)c1ccccc1]

or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

Compounds of the present invention include compounds having the formula (XXIII) or a pharmaceutically acceptable salt form thereof:

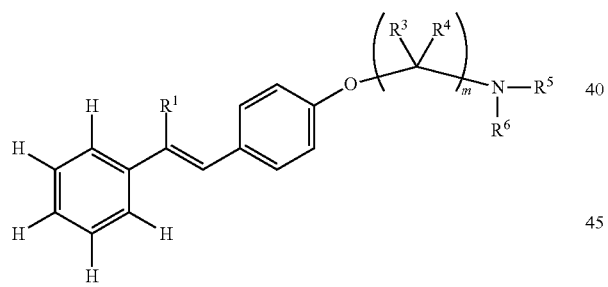

(XXIII)

wherein non-limiting examples of $R^1$, $R^3$, $R^4$, $R^5$, $R^6$, and m are defined herein below in Table 1.

TABLE 1

Exemplary compounds of the formula (XXIII)

| Entry | $R^1$ | $R^3$ | $R^4$ | $R^5$ | $R^6$ | m |
|---|---|---|---|---|---|---|
| 1 | Et | H | H | Me | Me | 3 |
| 2 | Et | H | H | Me | Me | 4 |
| 3 | Et | H | H | Me | Me | 5 |
| 4 | Et | H | H | Me | Me | 6 |
| 5 | Et | H | H | Me | Me | 7 |
| 6 | Et | H | H | Me | Me | 8 |
| 7 | Et | H | H | Me | Me | 9 |
| 8 | Et | H | H | Me | Me | 10 |
| 9 | Et | H | H | Me | Et | 2 |
| 10 | Et | H | H | iPr | n-hexyl | 2 |
| 11 | Et | H | H | Me | Me | 3 |
| 12 | Et | H | H | —(CH$_2$)$_5$— | | 2 |

TABLE 1-continued

Exemplary compounds of the formula (XXIII)

| Entry | $R^1$ | $R^3$ | $R^4$ | $R^5$ | $R^6$ | m |
|---|---|---|---|---|---|---|
| 13 | Et | H | H | —(CH$_2$)$_6$— | | 2 |
| 14 | Et | H | H | —(CH$_2$)$_2$—NH—(CH$_2$)$_2$— | | 2 |
| 15 | Et | H | H | —(CH$_2$)$_2$—NMe—(CH$_2$)$_2$— | | 2 |
| 16 | Et | H | H | —(CH$_2$)$_2$—O—(CH$_2$)$_2$— | | 2 |
| 17 | Et | H | Me | Me | Me | 2 |
| 18 | Et | H | iPr | Me | Me | 2 |
| 19 | Et | H | n-hexyl | Me | Me | 2 |
| 20 | Et | Me | Me | Me | Me | 2 |
| 21 | iPr | H | H | Me | Me | 2 |
| 22 | n-Pr | H | H | Me | Me | 2 |
| 23 | cyclopentyl | H | H | Me | Me | 2 |
| 24 | cyclohexyl | H | H | Me | Me | 2 |
| 25 | —CH$_2$-cyclohexyl | H | H | Me | Me | 2 |
| 26 | isobutyl | H | H | Me | Me | 2 |
| 27 | isopentyl | H | H | Me | Me | 2 |
| 28 | 5-decyl | H | H | Me | Me | 2 |
| 29 | n-butyl | H | H | —(CH$_2$)$_4$— | | 3 |

Compounds of the present invention include compounds having the formula (XXIV) or a pharmaceutically acceptable salt form thereof:

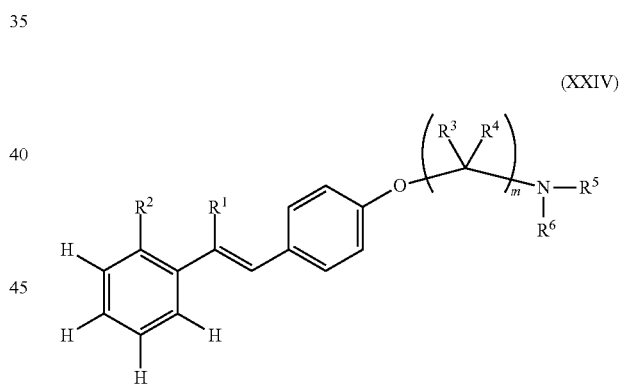

(XXIV)

wherein non-limiting examples of $R^1$, $R^2$, $R^3$, $R^4$, $R^5$, $R^6$, and m are defined herein below in Table 2.

TABLE 2

Exemplary compounds of the formula (XXIV)

| Entry | $R^1$ | $R^2$ | $R^3$ | $R^4$ | $R^5$ | $R^6$ | m |
|---|---|---|---|---|---|---|---|
| 1 | n-butyl | isopropenyl | H | H | Me | Me | 2 |
| 2 | n-butyl | vinyl | H | H | Me | Me | 2 |
| 3 | n-butyl | isopropyl | H | H | Me | Me | 2 |
| 4 | Et | OMe | H | H | Me | Me | 2 |
| 5 | Et | CN | H | H | Me | Me | 2 |

Compounds of the present invention include compounds having the formula (XXV) or a pharmaceutically acceptable salt form thereof:

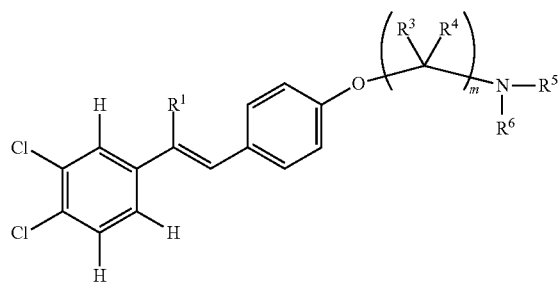

(XXV)

wherein non-limiting examples of $R^1$, $R^3$, $R^4$, $R^5$, $R^6$, and m are defined herein below in Table 3.

TABLE 3

Exemplary compounds of the formula (XXV)

| Entry | $R^1$ | $R^3$ | $R^4$ | $R^5$ | $R^6$ | m |
|---|---|---|---|---|---|---|
| 1 | Et | H | H | Me | Me | 2 |
| 2 | Et | H | H | Me | Me | 3 |
| 3 | Et | H | H | Me | Me | 4 |
| 4 | Et | H | H | Me | Me | 5 |

Compounds of the present invention include compounds having the formula (XXVI) or a pharmaceutically acceptable salt form thereof:

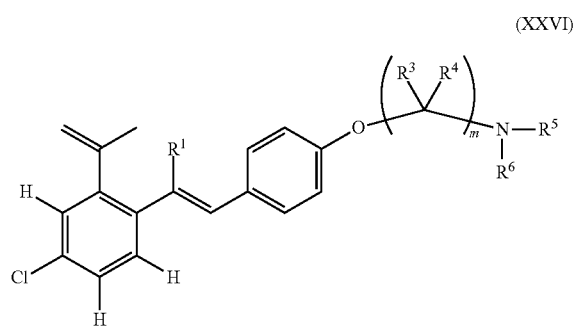

(XXVI)

wherein non-limiting examples of $R^1$, $R^3$, $R^4$, $R^5$, $R^6$, and m are defined herein below in Table 4.

TABLE 4

Exemplary compounds of the formula (XXVI)

| Entry | $R^1$ | $R^3$ | $R^4$ | $R^5$ | $R^6$ | M |
|---|---|---|---|---|---|---|
| 1 | Et | H | H | Me | Me | 2 |
| 2 | Et | H | H | Me | Me | 3 |
| 3 | Et | H | H | Me | Me | 4 |
| 4 | Et | H | H | Me | Me | 5 |

Compounds of the present invention include compounds having the formula (XXVII) or a pharmaceutically acceptable salt form thereof:

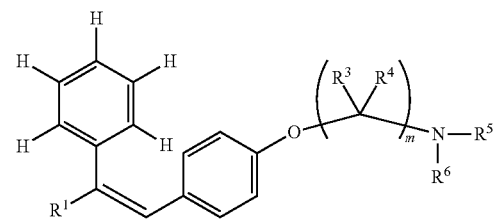

(XXVII)

wherein non-limiting examples of $R^1$, $R^3$, $R^4$, $R^5$, $R^6$, and m are defined herein below in Table 5.

TABLE 5

Exemplary compounds of the formula (XXVII)

| Entry | $R^1$ | $R^3$ | $R^4$ | $R^5$ | $R^6$ | m |
|---|---|---|---|---|---|---|
| 1 | Et | H | H | Me | Me | 3 |
| 2 | Et | H | H | Me | Me | 4 |
| 3 | Et | H | H | Me | Me | 5 |
| 4 | Et | H | H | Me | Me | 6 |
| 5 | Et | H | H | Me | Me | 7 |
| 6 | Et | H | H | Me | Me | 8 |
| 7 | Et | H | H | Me | Me | 9 |
| 8 | Et | H | H | Me | Me | 10 |
| 9 | Et | H | H | Me | Et | 2 |
| 10 | Et | H | H | iPr | n-hexyl | 2 |
| 11 | Et | H | H | Me | Me | 3 |
| 12 | Et | H | H | —(CH$_2$)$_4$— | | 2 |
| 13 | Et | H | H | —(CH$_2$)$_5$— | | 2 |
| 14 | Et | H | H | —(CH$_2$)$_6$— | | 2 |
| 15 | Et | H | H | —(CH$_2$)$_2$—NH—(CH$_2$)$_2$— | | 2 |
| 16 | Et | H | H | —(CH$_2$)$_2$—NMe—(CH$_2$)$_2$— | | 2 |
| 17 | Et | H | H | —(CH$_2$)$_2$—O—(CH$_2$)$_2$— | | 2 |
| 18 | Et | H | Me | Me | Me | 2 |
| 19 | Et | H | iPr | Me | Me | 2 |
| 20 | Et | H | n-hexyl | Me | Me | 2 |
| 21 | Et | Me | Me | Me | Me | 2 |
| 22 | iPr | H | H | Me | Me | 2 |
| 23 | n-Pr | H | H | Me | Me | 2 |
| 24 | cyclopentyl | H | H | Me | Me | 2 |
| 25 | cyclohexyl | H | H | Me | Me | 2 |
| 26 | —CH$_2$-cyclohexyl | H | H | Me | Me | 2 |
| 27 | isobutyl | H | H | Me | Me | 2 |
| 28 | isopentyl | H | H | Me | Me | 2 |
| 29 | 5-decyl | H | H | Me | Me | 2 |
| 30 | n-butyl | H | H | —(CH$_2$)$_4$— | | 3 |

Compounds of the present invention include compounds having the formula (XXVIII) or a pharmaceutically acceptable salt form thereof:

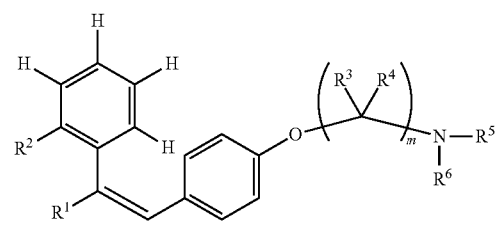

(XXVIII)

wherein non-limiting examples of $R^1$, $R^3$, $R^4$, $R^5$, $R^6$, and m are defined herein below in Table 6.

TABLE 6

Exemplary compounds of the formula (XXVIII)

| Entry | R¹ | R² | R³ | R⁴ | R⁵ | R⁶ | m |
|---|---|---|---|---|---|---|---|
| 1 | n-butyl | isopropenyl | H | H | Me | Me | 2 |
| 2 | n-butyl | vinyl | H | H | Me | Me | 2 |
| 3 | n-butyl | isopropyl | H | H | Me | Me | 2 |
| 4 | Et | OMe | H | H | Me | Me | 2 |
| 5 | Et | CN | H | H | Me | Me | 2 |

Compounds of the present invention include compounds having the formula (XXIX) or a pharmaceutically acceptable salt form thereof:

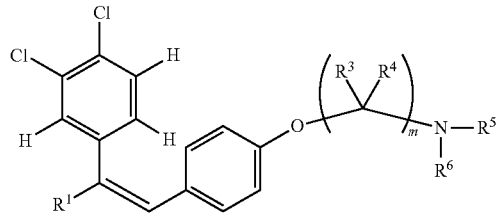

(XXIX)

wherein non-limiting examples of R¹, R³, R⁴, R⁵, R⁶, and m are defined herein below in Table 7.

TABLE 7

Exemplary compounds of the formula (XXIX)

| Entry | R¹ | R³ | R⁴ | R⁵ | R⁶ | m |
|---|---|---|---|---|---|---|
| 1 | Et | H | H | Me | Me | 2 |
| 2 | Et | H | H | Me | Me | 3 |
| 3 | Et | H | H | Me | Me | 4 |
| 4 | Et | H | H | Me | Me | 5 |

Compounds of the present invention include compounds having the formula (XXX) or a pharmaceutically acceptable salt form thereof:

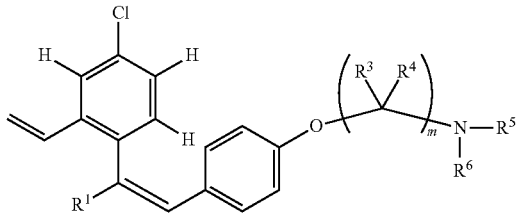

(XXX)

wherein non-limiting examples of R¹, R³, R⁴, R⁵, R⁶, and m are defined herein below in Table 8.

TABLE 8

Exemplary compounds of the formula (XXX)

| Entry | R¹ | R³ | R⁴ | R⁵ | R⁶ | M |
|---|---|---|---|---|---|---|
| 1 | Et | H | H | Me | Me | 2 |
| 2 | Et | H | H | Me | Me | 3 |

TABLE 8-continued

Exemplary compounds of the formula (XXX)

| Entry | R¹ | R³ | R⁴ | R⁵ | R⁶ | M |
|---|---|---|---|---|---|---|
| 3 | Et | H | H | Me | Me | 4 |
| 4 | Et | H | H | Me | Me | 5 |

Compounds of the present invention include compounds having the formula (XXXI) or a pharmaceutically acceptable salt form thereof:

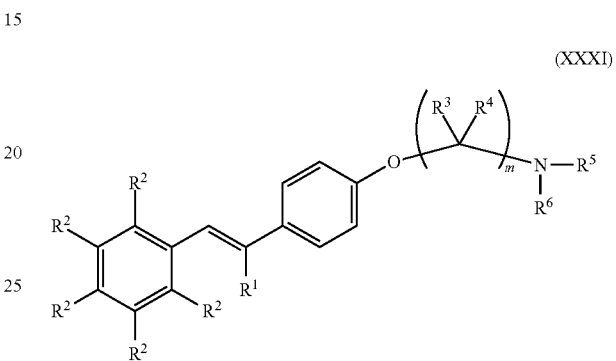

(XXXI)

wherein non-limiting examples of R¹, R³, R⁴, R⁵, R⁶, and m are defined herein below in Table 9

TABLE 9

Exemplary compounds of the formula (XXXI)

| Entry | R¹ | R³ | R⁴ | R⁵ | R⁶ | m |
|---|---|---|---|---|---|---|
| 1 | Et | H | H | Me | Me | 3 |
| 2 | Et | H | H | Me | Me | 4 |
| 3 | Et | H | H | Me | Me | 5 |
| 4 | Et | H | H | Me | Me | 6 |
| 5 | Et | H | H | Me | Me | 7 |
| 6 | Et | H | H | Me | Me | 8 |
| 7 | Et | H | H | Me | Me | 9 |
| 8 | Et | H | H | Me | Me | 10 |
| 9 | Et | H | H | Me | Et | 2 |
| 10 | Et | H | H | iPr | n-hexyl | 2 |
| 11 | Et | H | H | Me | Me | 3 |
| 12 | Et | H | H | —(CH₂)₄— | | 2 |
| 13 | Et | H | H | —(CH₂)₅— | | 2 |
| 14 | Et | H | H | —(CH₂)₆— | | 2 |
| 15 | Et | H | H | —(CH₂)₂—NH—(CH₂)₂— | | 2 |
| 16 | Et | H | H | —(CH₂)₂—NMe—(CH₂)₂— | | 2 |
| 17 | Et | H | H | —(CH₂)₂—O—(CH₂)₂— | | 2 |
| 18 | Et | H | Me | Me | Me | 2 |
| 19 | Et | H | iPr | Me | Me | 2 |
| 20 | Et | H | n-hexyl | Me | Me | 2 |
| 21 | Et | Me | Me | Me | Me | 2 |
| 22 | iPr | H | H | Me | Me | 2 |
| 23 | n-Pr | H | H | Me | Me | 2 |
| 24 | cyclopentyl | H | H | Me | Me | 2 |
| 25 | cyclohexyl | H | H | Me | Me | 2 |
| 26 | —CH₂-cyclohexyl | H | H | Me | Me | 2 |
| 27 | isobutyl | H | H | Me | Me | 2 |
| 28 | isopentyl | H | H | Me | Me | 2 |
| 29 | 5-decyl | H | H | Me | Me | 2 |
| 30 | n-butyl | H | H | —(CH₂)₄— | | 3 |

Compounds of the present invention include compounds having the formula (XXXII) or a pharmaceutically acceptable salt form thereof:

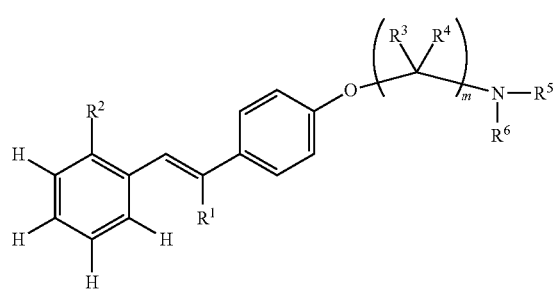

(XXXII)

wherein non-limiting examples of $R^1$, $R^2$, $R^3$, $R^4$, $R^5$, $R^6$, and m are defined herein below in Table 10

TABLE 10

Exemplary compounds of the formula (XXXII)

| Entry | $R^1$ | $R^2$ | $R^3$ | $R^4$ | $R^5$ | $R^6$ | m |
|---|---|---|---|---|---|---|---|
| 1 | n-butyl | isopropenyl | H | H | Me | Me | 2 |
| 2 | n-butyl | vinyl | H | H | Me | Me | 2 |
| 3 | n-butyl | isopropyl | H | H | Me | Me | 2 |
| 4 | Et | OMe | H | H | Me | Me | 2 |
| 5 | Et | CN | H | H | Me | Me | 2 |

Compounds of the present invention include compounds having the formula (XXXIII) or a pharmaceutically acceptable salt form thereof:

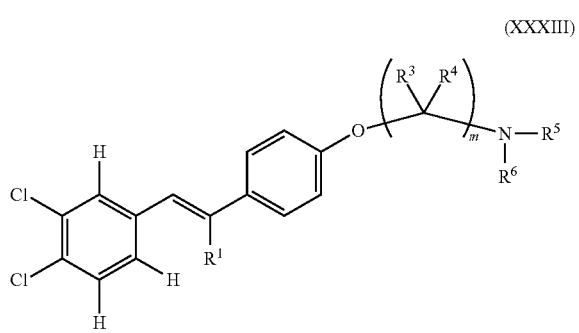

(XXXIII)

wherein non-limiting examples of $R^1$, $R^3$, $R^4$, $R^5$, $R^6$, and m are defined herein below in Table 11

TABLE 11

Exemplary compounds of the formula (XXXIII)

| Entry | $R^1$ | $R^3$ | $R^4$ | $R^5$ | $R^6$ | m |
|---|---|---|---|---|---|---|
| 1 | Et | H | H | Me | Me | 2 |
| 2 | Et | H | H | Me | Me | 3 |
| 3 | Et | H | H | Me | Me | 4 |
| 4 | Et | H | H | Me | Me | 5 |

Compounds of the present invention include compounds having the formula (XXXIV) or a pharmaceutically acceptable salt form thereof:

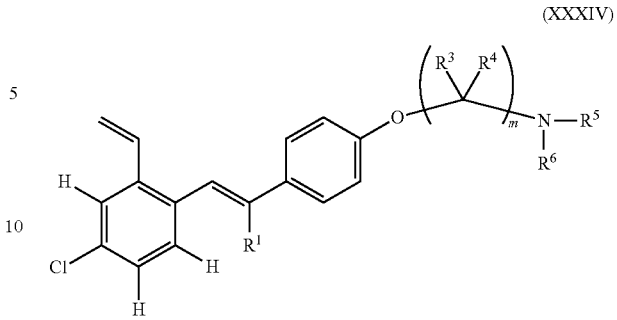

(XXXIV)

wherein non-limiting examples of $R^1$, $R^3$, $R^4$, $R^5$, $R^6$, and m are defined herein below in Table 12

TABLE 12

Exemplary compounds of the formula (XXXIV)

| Entry | $R^1$ | $R^3$ | $R^4$ | $R^5$ | $R^6$ | M |
|---|---|---|---|---|---|---|
| 1 | Et | H | H | Me | Me | 2 |
| 2 | Et | H | H | Me | Me | 3 |
| 3 | Et | H | H | Me | Me | 4 |
| 4 | Et | H | H | Me | Me | 5 |

Compounds of the present invention include compounds having the formula (XXXV) or a pharmaceutically acceptable salt form thereof:

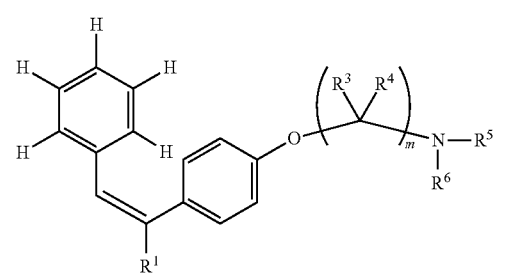

(XXXV)

wherein non-limiting examples of $R^1$, $R^3$, $R^4$, $R^5$, $R^6$, and m are defined herein below in Table 13

TABLE 13

Exemplary compounds of the formula (XXXV)

| Entry | $R^1$ | $R^3$ | $R^4$ | $R^5$ | $R^6$ | m |
|---|---|---|---|---|---|---|
| 1 | Et | H | H | Me | Me | 3 |
| 2 | Et | H | H | Me | Me | 4 |
| 3 | Et | H | H | Me | Me | 5 |
| 4 | Et | H | H | Me | Me | 6 |
| 5 | Et | H | H | Me | Me | 7 |
| 6 | Et | H | H | Me | Me | 8 |
| 7 | Et | H | H | Me | Me | 9 |
| 8 | Et | H | H | Me | Me | 10 |
| 9 | Et | H | H | Me | Et | 2 |
| 10 | Et | H | H | iPr | n-hexyl | 2 |
| 11 | Et | H | H | Me | Me | 3 |
| 12 | Et | H | H | —(CH$_2$)$_5$— | | 2 |
| 13 | Et | H | H | —(CH$_2$)$_6$— | | 2 |
| 14 | Et | H | H | —(CH$_2$)$_2$—NH—(CH$_2$)$_2$— | | 2 |
| 15 | Et | H | H | —(CH$_2$)$_2$—NMe—(CH$_2$)$_2$— | | 2 |
| 16 | Et | H | H | —(CH$_2$)$_2$—O—(CH$_2$)$_2$— | | 2 |

TABLE 13-continued

Exemplary compounds of the formula (XXXV)

| Entry | $R^1$ | $R^3$ | $R^4$ | $R^5$ | $R^6$ | m |
|---|---|---|---|---|---|---|
| 17 | Et | H | Me | Me | Me | 2 |
| 18 | Et | H | iPr | Me | Me | 2 |
| 19 | Et | H | n-hexyl | Me | Me | 2 |
| 20 | Et | Me | Me | Me | Me | 2 |
| 21 | iPr | H | H | Me | Me | 2 |
| 22 | n-Pr | H | H | Me | Me | 2 |
| 23 | cyclopentyl | H | H | Me | Me | 2 |
| 24 | cyclohexyl | H | H | Me | Me | 2 |
| 25 | —CH$_2$-cyclohexyl | H | H | Me | Me | 2 |
| 26 | isobutyl | H | H | Me | Me | 2 |
| 27 | isopentyl | H | H | Me | Me | 2 |
| 28 | 5-decyl | H | H | Me | Me | 2 |
| 29 | n-butyl | H | H | —(CH$_2$)$_4$— | | 3 |

Compounds of the present invention include compounds having the formula (XXXVI) or a pharmaceutically acceptable salt form thereof:

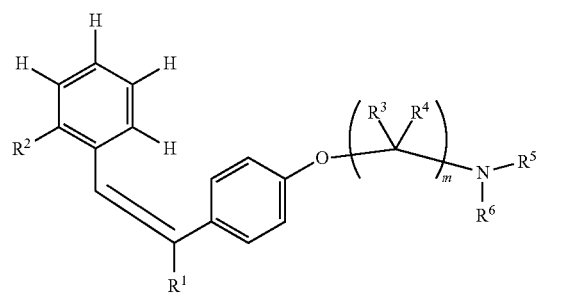

(XXXVI)

wherein non-limiting examples of $R^1$, $R^2$, $R^3$, $R^4$, $R^5$, $R^6$, and m are defined herein below in Table 14

TABLE 14

Exemplary compounds of the formula (XXXVI)

| Entry | $R^1$ | $R^2$ | $R^3$ | $R^4$ | $R^5$ | $R^6$ | m |
|---|---|---|---|---|---|---|---|
| 1 | n-butyl | isopropenyl | H | H | Me | Me | 2 |
| 2 | n-butyl | vinyl | H | H | Me | Me | 2 |
| 3 | n-butyl | isopropyl | H | H | Me | Me | 2 |
| 4 | Et | OMe | H | H | Me | Me | 2 |
| 5 | Et | CN | H | H | Me | Me | 2 |

Compounds of the present invention include compounds having the formula (XXXVII) or a pharmaceutically acceptable salt form thereof:

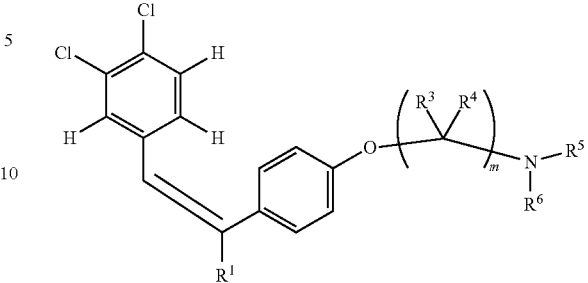

(XXXVII)

wherein non-limiting examples of $R^1$, $R^3$, $R^4$, $R^5$, $R^6$, and m are defined herein below in Table 15

TABLE 15

Exemplary compounds of the formula (XXXVII)

| Entry | $R^1$ | $R^3$ | $R^4$ | $R^5$ | $R^6$ | m |
|---|---|---|---|---|---|---|
| 1 | Et | H | H | Me | Me | 2 |
| 2 | Et | H | H | Me | Me | 3 |
| 3 | Et | H | H | Me | Me | 4 |
| 4 | Et | H | H | Me | Me | 5 |

Compounds of the present invention include compounds having the formula (XXXVIII) or a pharmaceutically acceptable salt form thereof:

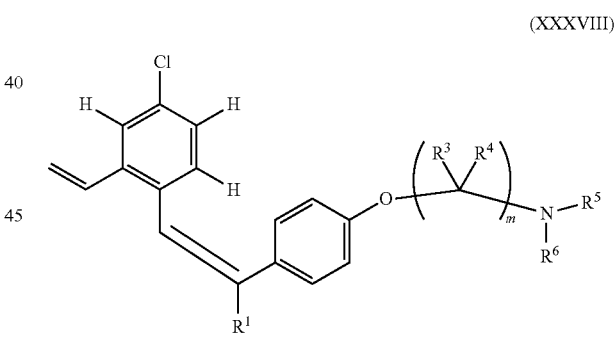

(XXXVIII)

wherein non-limiting examples of $R^1$, $R^3$, $R^4$, $R^5$, $R^6$, and m are defined herein below in Table 16

TABLE 16

Exemplary compounds of the formula (XXXVIII)

| Entry | $R^1$ | $R^3$ | $R^4$ | $R^5$ | $R^6$ | M |
|---|---|---|---|---|---|---|
| 1 | Et | H | H | Me | Me | 2 |
| 2 | Et | H | H | Me | Me | 3 |
| 3 | Et | H | H | Me | Me | 4 |
| 4 | Et | H | H | Me | Me | 5 |

Compounds of the present invention include compounds having the formula (XXXIX) or a pharmaceutically acceptable salt form thereof:

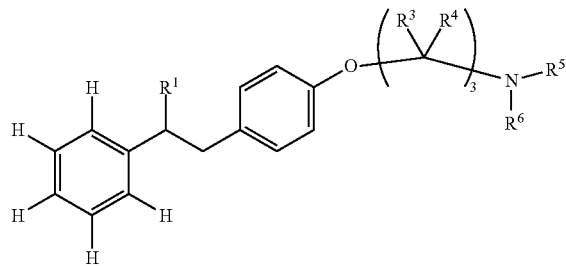

(XXXIX)

wherein non-limiting examples of $R^1$, $R^3$, $R^4$, $R^5$, $R^6$, and m are defined herein below in Table 17

TABLE 17

Exemplary compounds of the formula (XXXIX)

| Entry | $R^1$ | $R^3$ | $R^4$ | $R^5$ | $R^6$ | m |
|---|---|---|---|---|---|---|
| 1 | Et | H | H | Me | Me | 3 |
| 2 | Et | H | H | Me | Me | 4 |
| 3 | Et | H | H | Me | Me | 5 |
| 4 | Et | H | H | Me | Me | 6 |
| 5 | Et | H | H | Me | Me | 7 |
| 6 | Et | H | H | Me | Me | 8 |
| 7 | Et | H | H | Me | Me | 9 |
| 8 | Et | H | H | Me | Me | 10 |
| 9 | Et | H | H | Me | Et | 2 |
| 10 | Et | H | H | iPr | n-hexyl | 2 |
| 11 | Et | H | H | Me | Me | 3 |
| 12 | Et | H | H | —(CH$_2$)$_4$— | | 2 |
| 13 | Et | H | H | —(CH$_2$)$_5$— | | 2 |
| 14 | Et | H | H | —(CH$_2$)$_6$— | | 2 |
| 15 | Et | H | H | —(CH$_2$)$_2$—NH—(CH$_2$)$_2$— | | 2 |
| 16 | Et | H | H | —(CH$_2$)$_2$—NMe—(CH$_2$)$_2$— | | 2 |
| 17 | Et | H | H | —(CH$_2$)$_2$—O—(CH$_2$)$_2$— | | 2 |
| 18 | Et | H | Me | Me | Me | 2 |
| 19 | Et | H | iPr | Me | Me | 2 |
| 20 | Et | H | n-hexyl | Me | Me | 2 |
| 21 | Et | Me | Me | Me | Me | 2 |
| 22 | iPr | H | H | Me | Me | 2 |
| 23 | n-Pr | H | H | Me | Me | 2 |
| 24 | cyclopentyl | H | H | Me | Me | 2 |
| 25 | cyclohexyl | H | H | Me | Me | 2 |
| 26 | —CH$_2$-cyclohexyl | H | H | Me | Me | 2 |
| 27 | isobutyl | H | H | Me | Me | 2 |
| 28 | isopentyl | H | H | Me | Me | 2 |
| 29 | 5-decyl | H | H | Me | Me | 2 |
| 30 | n-butyl | H | H | —(CH$_2$)$_4$— | | 3 |

Compounds of the present invention include compounds having the formula (XXXX) or a pharmaceutically acceptable salt form thereof:

(XXXX)

wherein non-limiting examples of $R^1$, $R^2$, $R^3$, $R^4$, $R^5$, $R^6$, and m are defined herein below in Table 18

TABLE 18

Exemplary compounds of the formula (XXXX)

| Entry | $R^1$ | $R^2$ | $R^3$ | $R^4$ | $R^5$ | $R^6$ | m |
|---|---|---|---|---|---|---|---|
| 1 | n-butyl | isopropenyl | H | H | Me | Me | 2 |
| 2 | n-butyl | vinyl | H | H | Me | Me | 2 |
| 3 | n-butyl | isopropyl | H | H | Me | Me | 2 |
| 4 | Et | OMe | H | H | Me | Me | 2 |
| 5 | Et | CN | H | H | Me | Me | 2 |

Compounds of the present invention include compounds having the formula (XXXX) or a pharmaceutically acceptable salt form thereof:

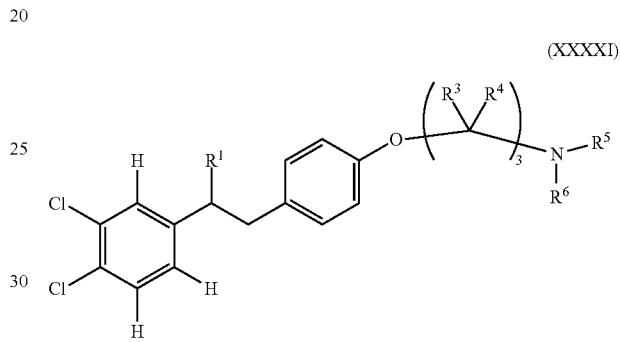

(XXXXI)

wherein non-limiting examples of $R^1$, $R^3$, $R^4$, $R^5$, $R^6$, and m are defined herein below in Table 19

TABLE 19

Exemplary compounds of the formula (XXXXI)

| Entry | $R^1$ | $R^3$ | $R^4$ | $R^5$ | $R^6$ | m |
|---|---|---|---|---|---|---|
| 1 | Et | H | H | Me | Me | 2 |
| 2 | Et | H | H | Me | Me | 3 |
| 3 | Et | H | H | Me | Me | 4 |
| 4 | Et | H | H | Me | Me | 5 |

Compounds of the present invention include compounds having the formula (XXXXII) or a pharmaceutically acceptable salt form thereof:

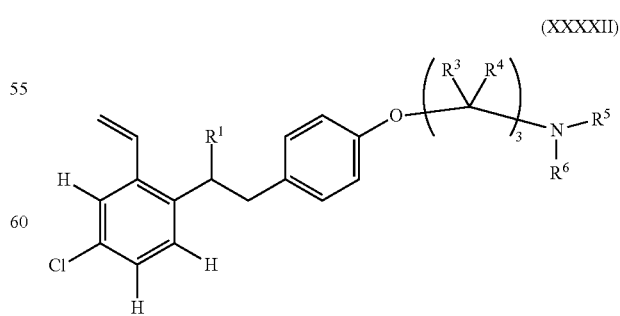

(XXXXII)

wherein non-limiting examples of $R^1$, $R^3$, $R^4$, $R^5$, $R^6$, and m are defined herein below in Table 20

TABLE 20

| Entry | R¹ | R³ | R⁴ | R⁵ | R⁶ | M |
|---|---|---|---|---|---|---|
| 1 | Et | H | H | Me | Me | 2 |
| 2 | Et | H | H | Me | Me | 3 |
| 3 | Et | H | H | Me | Me | 4 |
| 4 | Et | H | H | Me | Me | 5 |

Exemplary compounds of the formula (XXXXII)

Compounds of the present invention include compounds having the formula (XXXXIII) or a pharmaceutically acceptable salt form thereof:

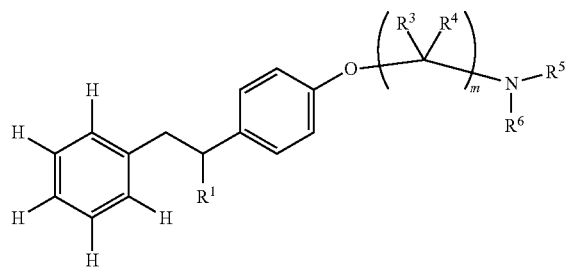

(XXXXIII)

wherein non-limiting examples of $R^1$, $R^3$, $R^4$, $R^5$, $R^6$, and m are defined herein below in Table 21.

TABLE 21

Exemplary compounds of the formula (XXXXIII)

| Entry | R¹ | R³ | R⁴ | R⁵ | R⁶ | m |
|---|---|---|---|---|---|---|
| 1 | Et | H | H | Me | Me | 2 |
| 2 | Et | H | H | Me | Me | 3 |
| 3 | Et | H | H | Me | Me | 4 |
| 4 | Et | H | H | Me | Me | 5 |
| 5 | Et | H | H | Me | Me | 6 |
| 6 | Et | H | H | Me | Me | 7 |
| 7 | Et | H | H | Me | Me | 8 |
| 8 | Et | H | H | Me | Me | 9 |
| 9 | Et | H | H | Me | Me | 10 |
| 10 | Et | H | H | Me | Et | 2 |
| 11 | Et | H | H | iPr | n-hexyl | 2 |
| 12 | Et | H | H | Me | Me | 3 |
| 13 | Et | H | H | —(CH₂)₄— | | 2 |
| 14 | Et | H | H | —(CH₂)₅— | | 2 |
| 15 | Et | H | H | —(CH₂)₆— | | 2 |
| 16 | Et | H | H | —(CH₂)₂—NH—(CH₂)₂— | | 2 |
| 17 | Et | H | H | —(CH₂)₂—NMe—(CH₂)₂— | | 2 |
| 18 | Et | H | H | —(CH₂)₂—O—(CH₂)₂— | | 2 |
| 19 | Et | H | Me | Me | Me | 2 |
| 20 | Et | H | iPr | Me | Me | 2 |
| 21 | Et | H | n-hexyl | Me | Me | 2 |
| 22 | Et | Me | Me | Me | Me | 2 |
| 23 | iPr | H | H | Me | Me | 2 |
| 24 | n-Pr | H | H | Me | Me | 2 |
| 25 | cyclopentyl | H | H | Me | Me | 2 |
| 26 | cyclohexyl | H | H | Me | Me | 2 |
| 27 | —CH₂-cyclohexyl | H | H | Me | Me | 2 |
| 28 | isobutyl | H | H | Me | Me | 2 |
| 29 | isopentyl | H | H | Me | Me | 2 |
| 30 | 5-decyl | H | H | Me | Me | 2 |
| 31 | n-butyl | H | H | —(CH₂)₄— | | 3 |

Compounds of the present invention include compounds having the formula (XXXXIV) or a pharmaceutically acceptable salt form thereof:

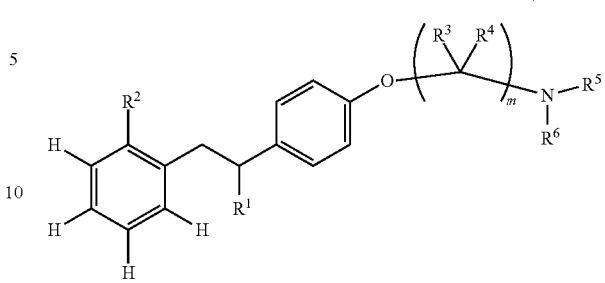

(XXXXIV)

wherein non-limiting examples of $R^1$, $R^2$, $R^3$, $R^4$, $R^5$, $R^6$, and m are defined herein below in Table 22.

TABLE 22

Exemplary compounds of the formula (XXXXIV)

| Entry | R¹ | R² | R³ | R⁴ | R⁵ | R⁶ | m |
|---|---|---|---|---|---|---|---|
| 1 | n-butyl | isopropenyl | H | H | Me | Me | 2 |
| 2 | n-butyl | vinyl | H | H | Me | Me | 2 |
| 3 | n-butyl | isopropyl | H | H | Me | Me | 2 |
| 4 | Et | OMe | H | H | Me | Me | 2 |
| 5 | Et | CN | H | H | Me | Me | 2 |

Compounds of the present invention include compounds having the formula (XXXXV) or a pharmaceutically acceptable salt form thereof:

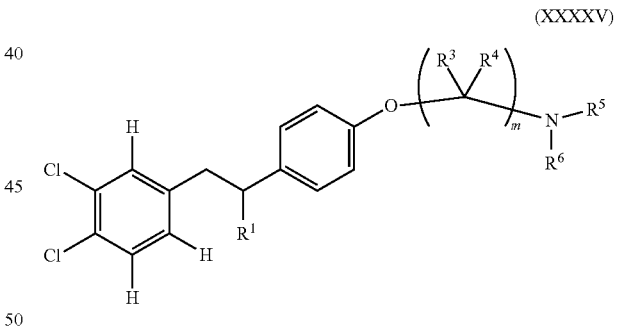

(XXXXV)

wherein non-limiting examples of $R^1$, $R^3$, $R^4$, $R^5$, $R^6$, and m are defined herein below in Table 23.

TABLE 23

Exemplary compounds of the formula (XXXXV)

| Entry | R¹ | R³ | R⁴ | R⁵ | R⁶ | m |
|---|---|---|---|---|---|---|
| 1 | Et | H | H | Me | Me | 2 |
| 2 | Et | H | H | Me | Me | 3 |
| 3 | Et | H | H | Me | Me | 4 |
| 4 | Et | H | H | Me | Me | 5 |

Compounds of the present invention include compounds having the formula (XXXXVI) or a pharmaceutically acceptable salt form thereof:

(XXXXVI)

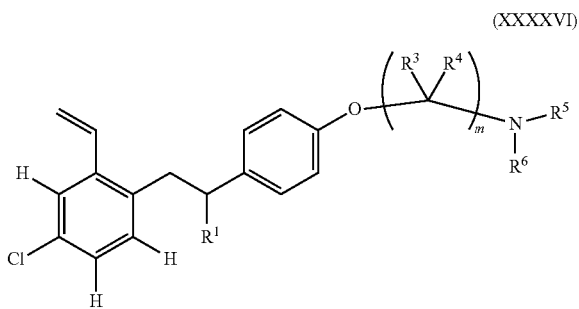

wherein non-limiting examples of $R^1$, $R^3$, $R^4$, $R^5$, $R^6$, and m are defined herein below in Table 24.

TABLE 24

Exemplary compounds of the formula (XXXXVI)

| Entry | $R^1$ | $R^3$ | $R^4$ | $R^5$ | $R^6$ | M |
|---|---|---|---|---|---|---|
| 1 | Et | H | H | Me | Me | 2 |
| 2 | Et | H | H | Me | Me | 3 |
| 3 | Et | H | H | Me | Me | 4 |
| 4 | Et | H | H | Me | Me | 5 |

Compounds of the present invention include compounds having the formula (XXXXVII) or a pharmaceutically acceptable salt form thereof:

(XXXXVII)

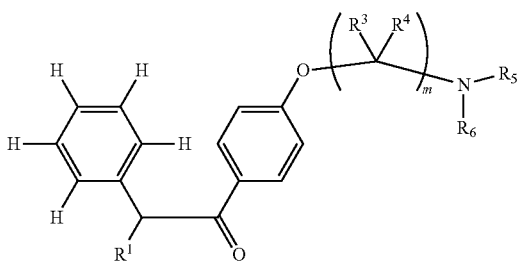

wherein non-limiting examples of $R^1$, $R^3$, $R^4$, $R^5$, $R^6$, and m are defined herein below in Table 25.

TABLE 25

Exemplary compounds of the formula (XXXXVII)

| Entry | $R^1$ | $R^3$ | $R^4$ | $R^5$ | $R^6$ | m |
|---|---|---|---|---|---|---|
| 1 | Et | H | H | Me | Me | 2 |
| 2 | Et | H | H | Me | Me | 3 |
| 3 | Et | H | H | Me | Me | 4 |
| 4 | Et | H | H | Me | Me | 5 |
| 5 | Et | H | H | Me | Me | 6 |
| 6 | Et | H | H | Me | Me | 7 |
| 7 | Et | H | H | Me | Me | 8 |
| 8 | Et | H | H | Me | Me | 9 |
| 9 | Et | H | H | Me | Me | 10 |
| 10 | Et | H | H | Me | Et | 2 |
| 11 | Et | H | H | iPr | n-hexyl | 2 |
| 12 | Et | H | H | Me | Me | 3 |
| 13 | Et | H | H | —(CH$_2$)$_4$— | | 2 |
| 14 | Et | H | H | —(CH$_2$)$_5$— | | 2 |
| 15 | Et | H | H | —(CH$_2$)$_6$— | | 2 |
| 16 | Et | H | H | —(CH$_2$)$_2$—NH—(CH$_2$)$_2$— | | 2 |
| 17 | Et | H | H | —(CH$_2$)$_2$—NMe—(CH$_2$)$_2$— | | 2 |

TABLE 25-continued

Exemplary compounds of the formula (XXXXVII)

| Entry | $R^1$ | $R^3$ | $R^4$ | $R^5$ | $R^6$ | m |
|---|---|---|---|---|---|---|
| 18 | Et | H | H | | —(CH$_2$)$_2$—O—(CH$_2$)$_2$— | 2 |
| 19 | Et | H | Me | Me | Me | 2 |
| 20 | Et | H | iPr | Me | Me | 2 |
| 21 | Et | H | n-hexyl | Me | Me | 2 |
| 22 | Et | Me | Me | Me | Me | 2 |
| 23 | n-Pr | H | H | Me | Me | 2 |
| 24 | cyclopentyl | H | H | Me | Me | 2 |
| 25 | cyclohexyl | H | H | Me | Me | 2 |
| 26 | —CH$_2$-cyclohexyl | H | H | Me | Me | 2 |
| 27 | 5-decyl | H | H | Me | Me | 2 |
| 28 | n-butyl | H | H | | —(CH$_2$)$_4$— | 3 |

Compounds of the present invention include compounds having the formula (XXXXVIII) or a pharmaceutically acceptable salt form thereof:

(XXXXVIII)

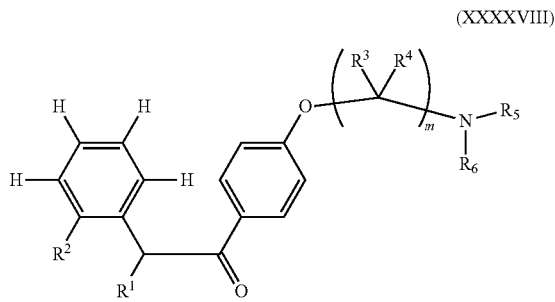

wherein non-limiting examples of $R^1$, $R^3$, $R^4$, $R^5$, $R^6$, and m are defined herein below in Table 26.

TABLE 26

Exemplary compounds of the formula (XXXXVIII)

| Entry | $R^1$ | $R^2$ | $R^3$ | $R^4$ | $R^5$ | $R^6$ | m |
|---|---|---|---|---|---|---|---|
| 1 | n-butyl | isopropenyl | H | H | Me | Me | 2 |
| 2 | n-butyl | vinyl | H | H | Me | Me | 2 |
| 3 | n-butyl | isopropyl | H | H | Me | Me | 2 |
| 4 | Et | OMe | H | H | Me | Me | 2 |
| 5 | Et | CN | H | H | Me | Me | 2 |

Compounds of the present invention include compounds having the formula (XXXXIX) or a pharmaceutically acceptable salt form thereof:

(XXXXIX)

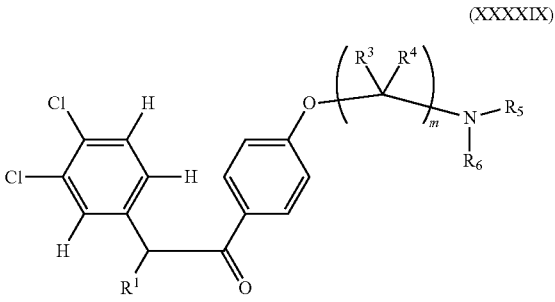

wherein non-limiting examples of $R^1$, $R^3$, $R^4$, $R^5$, $R^6$, and m are defined herein below in Table 26.

TABLE 26

Exemplary compounds of the formula (XXXXIX)

| Entry | $R^1$ | $R^3$ | $R^4$ | $R^5$ | $R^6$ | m |
|---|---|---|---|---|---|---|
| 1 | Et | H | H | Me | Me | 2 |
| 2 | Et | H | H | Me | Me | 3 |
| 3 | Et | H | H | Me | Me | 4 |
| 4 | Et | H | H | Me | Me | 5 |

Compounds of the present invention include compounds having the formula (XXXXX) or a pharmaceutically acceptable salt form thereof:

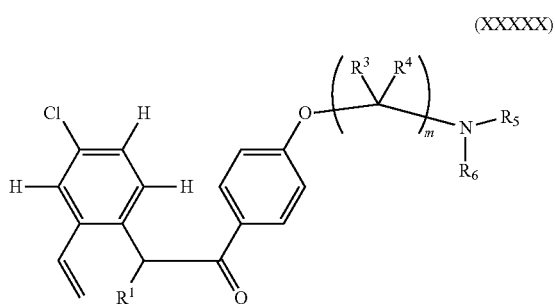

(XXXXX)

wherein non-limiting examples of $R^1$, $R^3$, $R^4$, $R^5$, $R^6$, and m are defined herein below in Table 27.

TABLE 27

Exemplary compounds of the formula (XXXXX)

| Entry | $R^1$ | $R^3$ | $R^4$ | $R^5$ | $R^6$ | M |
|---|---|---|---|---|---|---|
| 1 | Et | H | H | Me | Me | 2 |
| 2 | Et | H | H | Me | Me | 3 |
| 3 | Et | H | H | Me | Me | 4 |
| 4 | Et | H | H | Me | Me | 5 |

Process

The present invention further relates to a process for preparing the functionalized N,N-dialkylamino phenyl ethers of the present invention.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis*, 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out. A given reaction can be carried out in one solvent or a mixture of more than one solvent. Depending on the particular reaction step, suitable solvents for a particular reaction step can be selected.

An aspect of the process of the present invention relates to a process for preparing the functionalized N,N-dialkylamino phenyl ethers of the present invention having the formula (I).

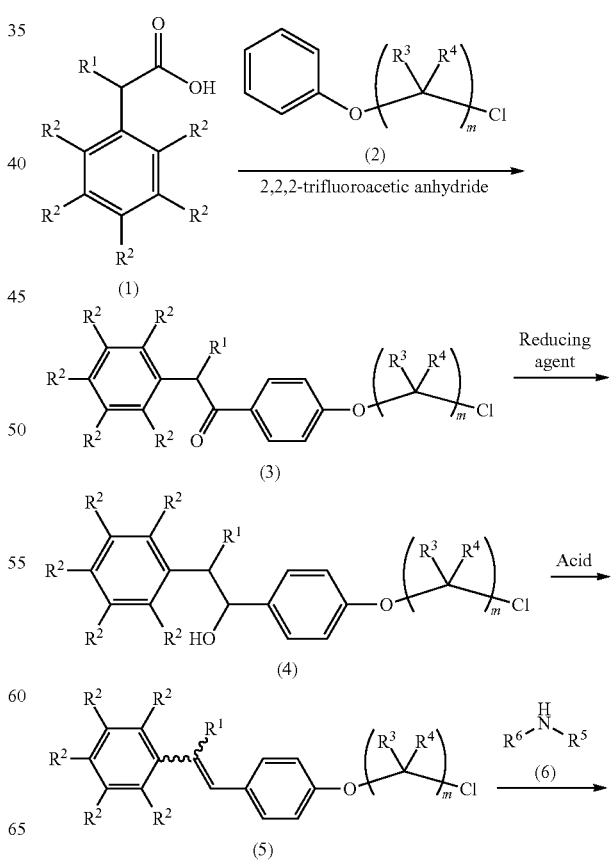

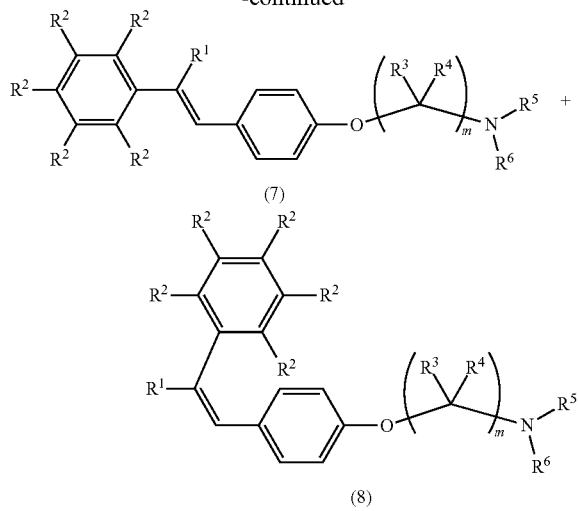

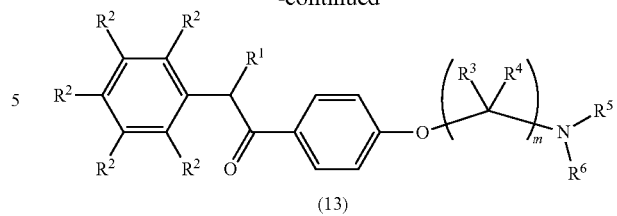

A compound of the formula (1), a known compound or a compound prepared by known methods, is reacted with a compound of the formula (2), a known compound or a compound prepared by known methods, in the presence of 2,2,2-trifluoroacetic anhydride, optionally in the presence of a solvent such as tetrahydrofuran, 1,4-dioxane, methylene chloride, and the like, optionally with heating, optionally with microwave irradiation to provide a compound of the formula (3). A compound of the formula (3) is reacted with a reducing agent such as lithium aluminum hydride, diisobutyl aluminum hydride, sodium borohydride, lithium borohydride, and the like, in a solvent such as tetrahydrofuran, 1,4-dioxane, methylene chloride, and the like, optionally with heating, optionally with microwave irradiation to provide a compound of the formula (4). A compound of the formula (4) is reacted with an acid such as hydrochloric acid, hydrobromic acid, sulfuric acid, and the like, optionally in the presence of a solvent such as methanol, ethanol, isopropanol, and the like, optionally with heating, optionally with microwave irradiation to provide a compound of the formula (5). A compound of the formula (5) is reacted with a compound of the formula (6), a known compound or a compound prepared by known methods, in the presence of a solvent such as methanol, ethanol, isopropanol, tetrahydrofuran, 1,4-dioxane, and the like, optionally in the presence of water, optionally with heating, optionally with microwave irradiation to provide a compound of the formula (7) and a compound of the formula (8) that are separated chromatographically or by crystallization.

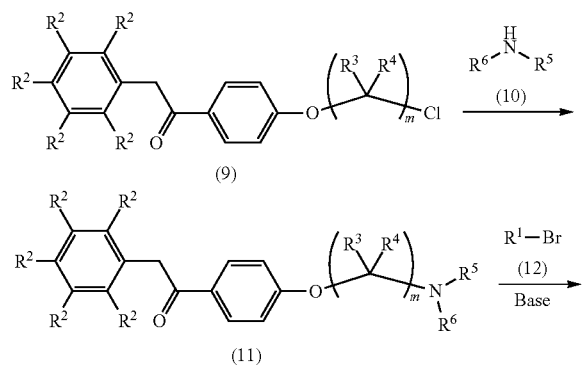

A compound of the formula (9), a known compound or a compound prepared by known methods, is reacted with a compound of the formula (10), a known compound or a compound prepared by known methods, in the presence of a solvent such as methanol, ethanol, isopropanol, tetrahydrofuran, 1,4-dioxane, and the like, optionally in the presence of water, optionally with heating, optionally with microwave irradiation to provide a compound of the formula (11). A compound of the formula (11) is reacted with a compound of the formula (12), a known compound or a compound prepared by known methods, in the presence of a base such as a lithium diisopropyl amine, sodium diisopropyl amine, sodium hydride, lithium bis(trimethylsilyl) amide, and the like, in a solvent such as tetrahydrofuran, 1,4-dioxane, methylene chloride, and the like, optionally with heating, optionally with microwave irradiation, to provide a compound of the formula (13).

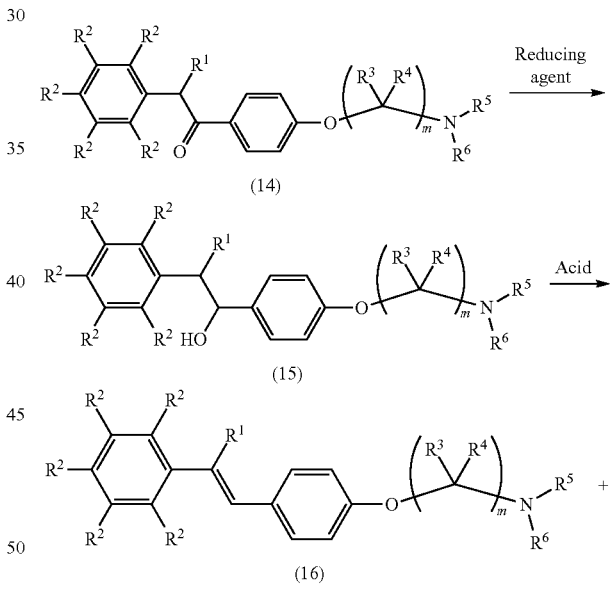

A compound of the formula (14) is reacted with a reducing agent such as lithium aluminum hydride, diisobutyl aluminum hydride, sodium borohydride, lithium borohydride, and the like, in a solvent such as tetrahydrofuran, 1,4-dioxane, methylene chloride, and the like, optionally with heating, optionally with microwave irradiation to provide a compound of the formula (15). A compound of the formula (15) is reacted with an acid such as hydrochloric acid, hydrobromic acid, sulfuric acid, and the like, optionally in the presence of a solvent such as methanol, ethanol, isopropanol, and the like, optionally with heating, optionally with microwave irradiation to provide a compound of the formula (16) and a compound of the formula (17) that are separated chromatographically.

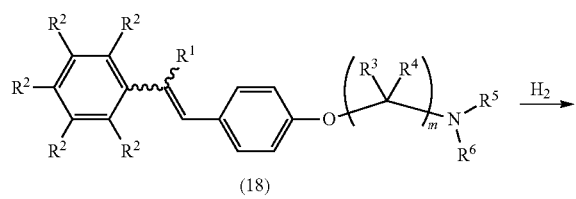

(18)

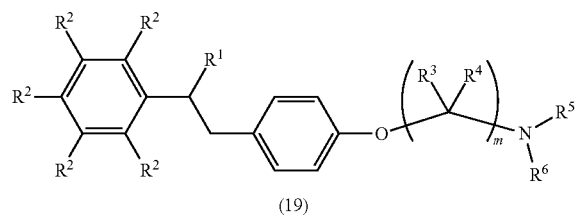

(19)

A compound of the formula (18) is reacted with hydrogen gas in the presence of a palladium catalyst such as palladium on carbon, palladium acetate, palladium bis(triphenylphosphine) dichloride, palladium tetrakis(triphenylphosphine)bis(acetonitrile), and the like, in an organic solvent such as methanol, ethanol, isopropanol, ethyl acetate, tetrahydrofuran, 1,4-dioxane, and the like to provide a compound of the formula (19).

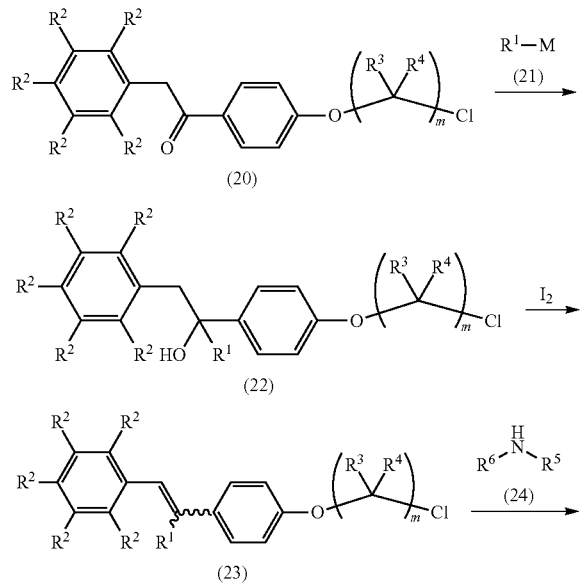

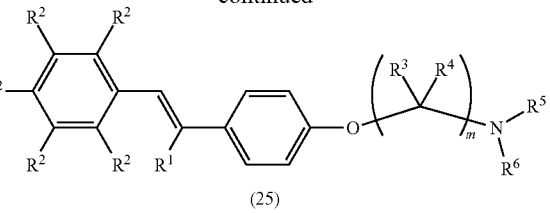

(25)

+

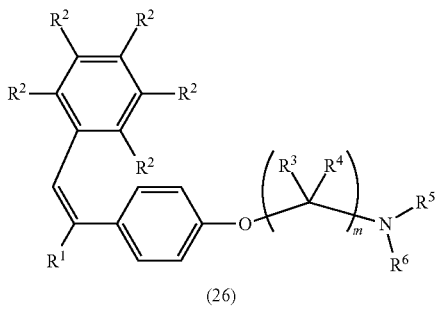

(26)

A compound of the formula (20) is reacted with a compound of the formula (21), a known compound or a compound prepared by known methods in which M is a metal such as magnesium, lithium, potassium, zinc, and the like, in the presence of a solvent such as tetrahydrofuran, 1,4-dioxane, methylene chloride, and the like, optionally with heating, optionally with microwave irradiation to provide a compound of the formula (22). A compound of the formula (22) is reacted with iodine in the presence of a solvent such as acetonitrile, tetrahydrofuran, 1,4-dioxane, methylene chloride, and the like, optionally with heating, optionally with microwave irradiation to provide a compound of the formula (23). A compound of the formula (23) is reacted with a compound of the formula (24), a known compound or a compound prepared by known methods, in the presence of a solvent such as methanol, ethanol, isopropanol, tetrahydrofuran, 1,4-dioxane, and the like, optionally in the presence of water, optionally with heating, optionally with microwave irradiation to provide a compound of the formula (25) and a compound of the formula (26) that are separated chromatographically.

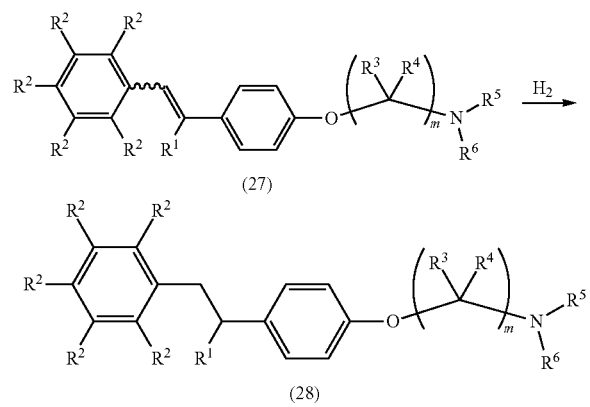

A compound of the formula (27) is reacted with hydrogen gas in the presence of a palladium catalyst such as palladium on carbon, palladium acetate, palladium bis(triphenylphosphine) dichloride, palladium tetrakis(triphenylphosphine)bis(acetonitrile), and the like, in an organic solvent such as methanol, ethanol, isopropanol, ethyl acetate, tetrahydrofuran, 1,4-dioxane, and the like to provide a compound of the formula (28).

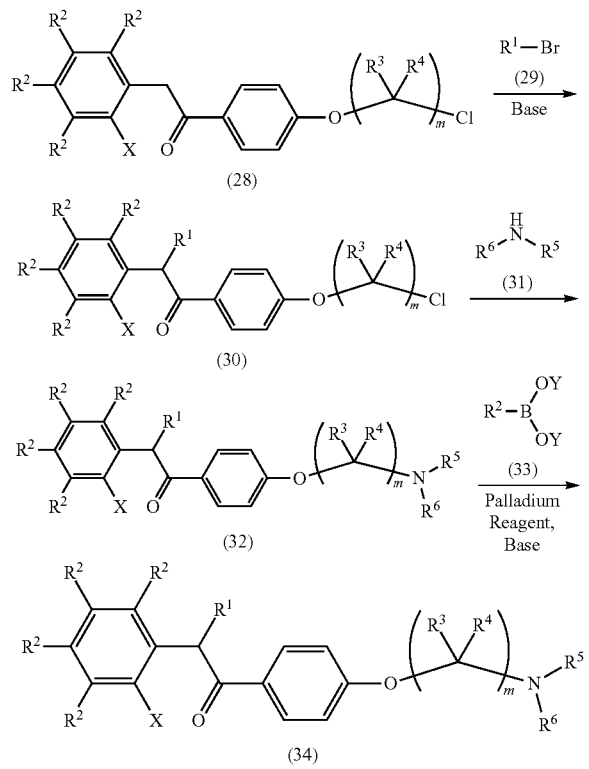

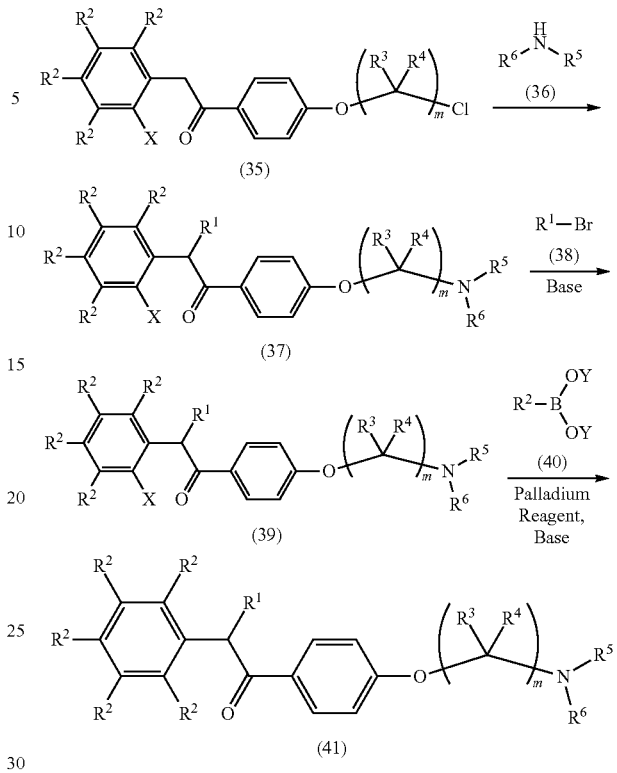

A compound of the formula (28), a known compound or a compound prepared by known methods where X is a suitable leaving group such as chlorine, bromine, iodine, toluenesulfonate, methanesulfonate and the like, is reacted with a compound of the formula (29), a known compound or a compound prepared by known methods, in the presence of a base such as a lithium diisopropyl amine, sodium diisopropyl amine, sodium hydride, lithium bis(trimethylsilyl) amide, and the like, in a solvent such as tetrahydrofuran, 1,4-dioxane, methylene chloride, and the like, optionally with heating, optionally with microwave irradiation, to provide a compound of the formula (30). A compound of the formula (30) is reacted with a compound of the formula (31), a known compound or a compound prepared by known methods, in the presence of a solvent such as methanol, ethanol, isopropanol, tetrahydrofuran, 1,4-dioxane, and the like, optionally in the presence of water, optionally with heating, optionally with microwave irradiation to provide a compound of the formula (32). A compound of formula (32) is reacted with a compound of formula (33), a known compound or a compound prepared by known methods where Y is H or the two Y groups taken together form a 1,1,2,2-tetramethylethylene moiety and a palladium reagent such as tetrakis(triphenylphosphine(palladium(0), bis (dibenzylidineacetone)palladium(O) and the like and a base such as sodium carbonate, sodium ethoxide, potassium carbonate, potassium fluoride and the like, in a solvent such as tetrahydrofuran, 1,4-dioxane and the like, optionally with the addition of water, optionally with heating, optionally with microwave irradiation, to provide a compound of the formula (34).

A compound of the formula (35), a known compound or a compound prepared by known methods where X is a suitable leaving group such as chlorine, bromine, iodine, toluenesulfonate, methanesulfonate and the like, is reacted with a compound of the formula (36), a known compound or a compound prepared by known methods, in the presence of a solvent such as methanol, ethanol, isopropanol, tetrahydrofuran, 1,4-dioxane, and the like, optionally in the presence of water, optionally with heating, optionally with microwave irradiation to provide a compound of the formula (37). A compound of formula (37), is reacted with a compound of the formula (38), a known compound or a compound prepared by known methods, in the presence of a base such as a lithium diisopropyl amine, sodium diisopropyl amine, sodium hydride, lithium bis(trimethylsilyl)amide, and the like, in a solvent such as tetrahydrofuran, 1,4-dioxane, methylene chloride, and the like, optionally with heating, optionally with microwave irradiation, to provide a compound of the formula (39). A compound of formula (39), is reacted with a compound of formula (40), a known compound or a compound prepared by known methods where Y is H or the two Y groups taken together form a 1,1,2,2-tetramethylethylene moiety and a palladium reagent such as tetrakis(triphenylphosphine(palladium(0), bis (dibenzylidineacetone)palladium(0) and the like and a base such as sodium carbonate, sodium ethoxide, potassium carbonate, potassium fluoride and the like, in a solvent such as tetrahydrofuran, 1,4-dioxane and the like, optionally with the addition of water, optionally with heating, optionally with microwave irradiation, to provide a compound of the formula (41).

The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

Example 1: Synthesis of (E)-N,N-Dimethyl-2-(4-(2-(phenyl)but-1-en-1-yl)phenoxy)ethan-1-amine (MC210150)

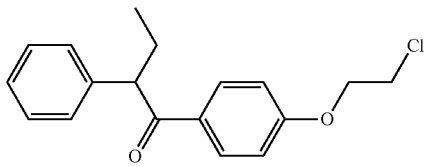

Step 1: 1-(4-(2-Chloroethoxy)phenyl)-2-phenylbutan-1-one: 2-Phenylbutanoic acid (5.2 g, 31.7 mmol) was suspended in 2,2,2-trifluoroacetic anhydride (5.12 mL, 31.7 mmol). Then (2-chloroethoxy)benzene (4 mL, 28.8 mmol) was added dropwise and the resulting mixture was stirred at room temperature overnight. The reaction was quenched with saturated sodium bicarbonate solution (70 mL) and extracted with ethyl acetate (2×50 mL). The combined organic layers were dried over anhydrous magnesium sulfate and concentrated on a rotary evaporator to afford 9.39 g (100%) of the desired product as a yellow solid that was used without further purification. $^1$H NMR (400 MHz, CDCl$_3$) δ 7.88 (d, J=8.9 Hz, 2H), 7.17 (m, 5H), 6.80 (d, J=8.9 Hz, 2H), 4.31 (t, J=7.2 Hz, 1H), 4.16 (t, J=5.8 Hz, 2H), 3.72 (t, J=5.8 Hz, 2H), 2.10 (m, 1H), 1.76 (m, 1H), 0.82 (t, J=7.36 Hz, 3H); MS (ESI) (m/z) 303.1/305.1 (M+H)$^+$.

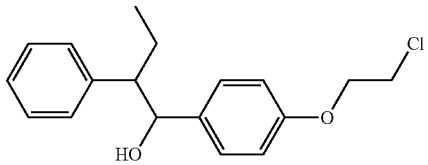 [SMILES: CCC(c1ccccc1)C(O)c1ccc(OCCCl)cc1]

Step 2: 1-(4-(2-Chloroethoxy)phenyl)-2-phenylbutan-1-ol: Lithium aluminum hydride (64.0 mg, 1.7 mmol) was suspended in anhydrous tetrahydrofuran (5 mL) in an oven-dried flask under a nitrogen atmosphere. Then a solution of 1-(4-(2-chloroethoxy)phenyl)-2-phenylbutan-1-one (300.0 mg, 1.0 mmol) in anhydrous tetrahydrofuran (5 mL) was added dropwise at room temperature. The resulting mixture was allowed to stir at room temperature for 2 days. The reaction was then quenched with 1N aqueous hydrochloric acid and extracted with ethyl acetate (2×20 mL). The combined organic layers were dried over anhydrous magnesium sulfate and concentrated on a rotary evaporator to afford 300.0 mg (100%) of the desired product as a white solid that was used without further purification. $^1$H NMR (400 MHz, CDCl$_3$) δ 7.89 (d, J=8.9 Hz, 2H), 7.27 (m, 2H), 7.17 (m, 3H), 6.83 (d, J=8.8 Hz, 2H), 4.60 (t, J=8.4 Hz, 1H), 4.17 (t, J=5.9 Hz, 2H), 3.75 (t, J=5.9 Hz, 2H), 1.38-1.33 (m, 2H), 0.56 (t, J=7.3 Hz, 3H); MS (ESI) (m/z) 287.1/289.1 (M-H$_2$O)$^+$.

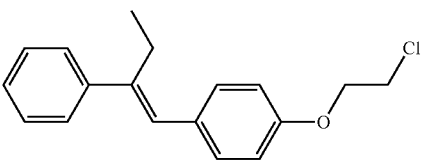 [SMILES: CC/C(=C\c1ccc(OCCCl)cc1)c1ccccc1]

Step 3: (E)-1-(2-Chloroethoxy)-4-(2-phenylbut-1-en-1-yl)benzene: 1-(4-(2-Chloro ethoxy)phenyl)-2-phenylbutan-1-ol (300.0 mg, 1.0 mmol) was suspended in ethanol (5 mL) and concentrated hydrochloric acid (1.25 mL). The stirred mixture was stirred at reflux for 2 hours and then stirred overnight at room temperature. The reaction mixture was concentrated on a rotary evaporator and purified by chromatography on silica gel (ethyl acetate/hexane) to afford 200 mg of a yellow solid that contained both E and Z isomers. The desired E isomer was obtained as a yellow solid by recrystallization from ethanol (40.0 mg, 14%). $^1$H NMR (400 MHz, CDCl$_3$) δ 7.38 (d, J=8.6 Hz, 2H), 7.29 (m, 2H), 7.22 (m, 3H), 6.9 (d, J=8.7 Hz, 2H), 6.56 (s, 1H), 4.19 (t, J=6.0 Hz, 2H), 3.76 (t, J=5.9 Hz, 2H), 2.66 (q, J=7.4 Hz, 2H), 0.99 (t, J=7.4 Hz, 3H). MS (ESI) (m/z) 287.1/289.1 (M+H)$^+$.

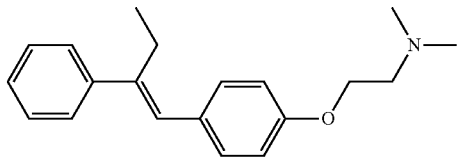 [SMILES: CC/C(=C\c1ccc(OCCN(C)C)cc1)c1ccccc1]

Step 4: (E)-N,N-Dimethyl-2-(4-(2-(phenyl)but-1-en-1-yl)phenoxy)ethan-1-amine (Example 1): (E)-1-(2-Chloroethoxy)-4-(2-phenylbut-1-en-1-yl)benzene (29.0 mg, 0.1 mmol) was dissolved in a mixture of 40% aqueous dimethylamine (1 mL) and ethanol (1 mL) and stirred at reflux overnight. The reaction mixture was cooled to room temperature and concentrated on a rotary evaporator. The resulting residue was purified by chromatography on silica gel (methanol/ethyl acetate with 0.1% NH$_4$H) to afford 16.0 mg (55%) of the desired product as a light yellow solid. $^1$H NMR (400 MHz, CDCl$_3$) δ 7.38 (d, J=8.7 Hz, 2H), 7.28 (m, 2H), 7.20 (m, 3H), 6.85 (d, J=8.7 Hz, 2H), 6.55 (s, 1H), 4.02 (t, J=5.8 Hz, 2H), 2.69-2.64 (m, 4H), 2.28 (s, 6H), 0.99 (t, J=7.48 Hz, 3H); MS (ESI) (m/z) 296.2 (M+H)$^+$.

Example 2: Synthesis of (Z)—N,N-Dimethyl-2-(4-(2-(phenyl)but-1-en-1-yl)phenoxy)ethan-1-amine trifluoroacetate (MC210151)

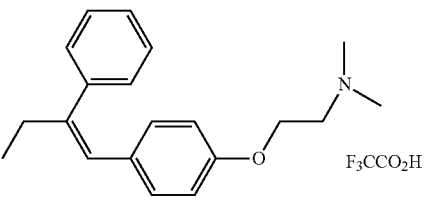

Step 1: (Z)—N,N-Dimethyl-2-(4-(2-(phenyl)but-1-en-1-yl)phenoxy)ethan-1-amine trifluoroacetate: The mixture of E and Z isomers from Example 1, Step 3 (29.0 mg, 0.1 mmol) were stirred at reflux in a mixture of 40% aqueous dimethylamine (1 mL) and ethanol (1 mL) for 2 hours. The residue was cooled and concentrated on a rotary evaporator and the residue was purified by chromatography on silica gel (methanol/ethyl acetate with 0.1% NH$_4$OH) followed by reversed-phase chromatography (C-18 column, gradient of acetonitrile in water with 0.1% trifluoroacetic acid) to afford 10.0 mg (25%) of the trifluoroacetate salt of the desired product as a white solid. $^1$H NMR (400 MHz, CDCl$_3$) δ 12.24 (s, 1H), 7.24-7.20 (m, 3H), 7.06 (m, 2H), 6.78 (d, J=8.80 Hz, 2H), 6.52 (d, J=8.8 Hz, 2H), 6.28 (s, 1H), 4.19 (t, J=3.4 Hz, 2H), 3.40 (t, J=4.5 Hz, 2H), 2.86 (s, 6H), 2.41 (q, J=7.0 Hz, 2H), 0.98 (t, J=7.4 Hz, 3H); MS (ESI) (m/z) 296.2 (M+H)$^+$.

Example 3: Synthesis of (E)-1-(2-(4-(2-phenylbut-1-en-1-yl)phenoxy)ethyl)pyrrolidine (MC210154)

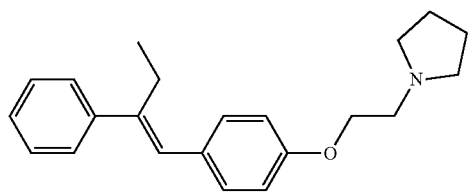 [SMILES: CC/C(=C\c1ccc(OCCN2CCCC2)cc1)c1ccccc1]

(E)-1-(2-(4-(2-Phenylbut-1-en-1-yl)phenoxy)ethyl)pyrrolidine: To a suspension of (E)-1-(2-Chloroethoxy)-4-(2-phenylbut-1-en-1-yl)benzene (Step 3, Example 1, 10.3 mg, 0.04 mmol) in ethanol (0.5 mL) was added pyrrolidine (70.8 µl, 0.86 mmol,). The resulting reaction mixture was stirred at reflux for 12 hours. The reaction was cooled to room temperature and concentrated on a rotary evaporator. The resulting residue was purified by chromatography on silica gel (methanol/acetate with 0.1% NH$_4$H) to afford 10.2 mg (88%) of the desired product as a light yellow solid. $^1$H NMR (400 MHz, CDCl$_3$) δ 7.37 (d, J=8.7 Hz, 2H), 7.30 (m, 2H), 7.19 (m, 3H), 6.87 (d, J=8.7 Hz, 2H), 6.55 (s, 1H), 4.10 (t, J=5.9 Hz, 2H), 2.89 (t, J=5.8 Hz, 2H), 2.66 (m, 6H), 1.77 (m, 4H), 0.99 (t, J=7.5 Hz, 3H); MS (ESI) (m/z) 322.2 (M+H)$^+$.

Example 4: Synthesis of (Z)—N,N-dimethyl-2-(4-(2-phenylhex-1-en-1-yl)phenoxy)ethan-1-amine trifluoroacetate (MC210167)

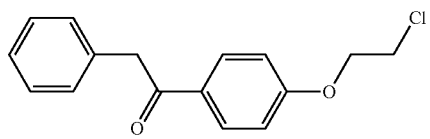

Step 1: 1-(4-(2-Chloroethoxy)phenyl)-2-phenylethan-1-one: Phenyl acetic acid (2.6 g, 19 mmol) was suspended in trifluoroacetic anhydride (11 mL, 76 mmol). Chloroethoxylbenzene (2.7 mL, 19 mmol) was added to the stirred suspension dropwise. The resulting mixture was allowed to stir overnight at room temperature. The reaction was quenched with 40% aqueous sodium hydroxide solution and then extracted with ethyl acetate (2×15 mL). The combined organic layers were dried over anhydrous magnesium sulfate and concentrated on a rotary evaporator. The resulting residue was purified by chromatography on silica gel (ethyl acetate/hexane) to afford 3.56 g (68%) of the desired product as a yellow solid. $^1$H NMR (400 MHz, CDCl$_3$) δ 7.93 (d, J=6.8 Hz, 2H), 7.22 (m, 5H), 6.87 (d, J=6.9 Hz, 2H), 4.21 (t, J=5.8 Hz, 2H), 4.17 (s, 2H), 3.76 (t, J=5.8 Hz, 2H); MS (ESI) (m/z) 275.1/277.1 (M+H)$^+$.

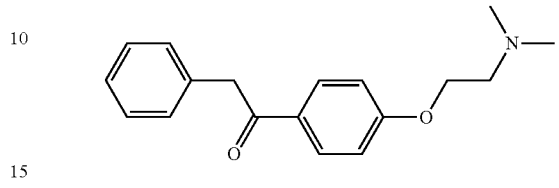

Step 2: 1-(4-(2-(Dimethylamino)ethoxy)phenyl)-2-phenylethan-1-one: 1-(4-(2-Chloro ethoxy)phenyl)-2-phenylethan-1-one (85.5 mg, 0.31 mmol) was suspended in 40% aqueous dimethylamine (4 mL) and stirred at reflux for 12 hours. The reaction mixture was cooled and then concentrated on a rotary evaporator. The resulting residue was purified by chromatography on silica gel (methanol/ethyl acetate with 0.1% concentrated ammonium hydroxide) to provide 52.2 mg (60%) of the desired product as a yellow solid. $^1$H NMR (40 0 MHz, CDCl$_3$) δ 7.91 (d, J=8.9 Hz, 2H), 7.23 (m, 5H), 6.87 (d, J=8.9 Hz, 2H), 4.16 (s, 2H), 4.09 (t, J=5.5 Hz, 2H), 2.74 (t, J=4.5 Hz, 2H), 2.32 (s, 6H); MS (ESI) (m/z) 284.2 (M+H)$^+$.

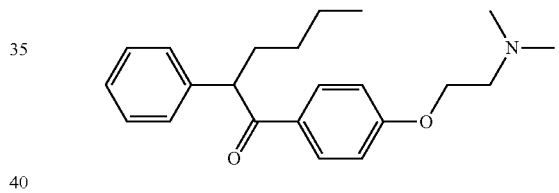

Step 3: 1-(4-(2-(Dimethylamino)ethoxy)phenyl)-2-phenylhexan-1-one: 1-(4-(2-(Dimethyl amino)-ethoxy)phenyl)-2-phenylethan-1-one (80.4 mg, 0.28 mmol) and n-butylbromide (33.7 µL, 0.31 mmol) dissolved in anhydrous tetrahydrofuran were treated with 60% sodium hydride in mineral oil (22.7 mg, 0.57 mmol) at 0° C. under a nitrogen atmosphere. The reaction was then stirred at reflux for 30 minutes, followed by stirring overnight at room temperature. The reaction was quenched by careful addition of methanol and concentrated to dryness on a rotary evaporator. The residue was partitioned between water (10 ml) and ethyl acetate (15 mL). The aqueous layer was extracted eiyh ethyl acetate (2×10 mL) and the combined organic layers were dried over anhydrous magnesium sulfate and concentrated on a rotary evaporator. The resulting residue was purification by reversed-phase chromatography (C-18 column, gradient of acetonitrile in water with 0.1% formic acid) to afford 58 mg (54%) of the desired product as a yellow solid. $^1$H NMR (400 MHz, MeOD) δ 8.06 (d, J=8.8 Hz, 2H), 7.28 (m, 5H), 7.05 (d, J=8.9 Hz, 2H), 4.68 (t, J=5.9 Hz, 1H), 4.43 (d, J=5.7 Hz, 2H), 3.65 (d, J=5.7 Hz, 2H), 3.00 (s, 6H), 2.18 (m, 1H), 1.77 (m, 1H), 1.38 (m, 4H), 0.88 (t, J=6.4 Hz, 3H); MS (ESI) (m/z) 340.2 (M+H)$^+$.

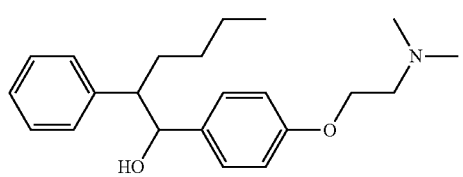 [SMILES: CCCCC(c1ccccc1)C(O)c1ccc(OCCN(C)C)cc1]

Step 4—1-(4-(2-(Dimethylamino)ethoxy)phenyl)-2-phenylhexan-1-ol: Lithium aluminum hydride 11.0 mg, 0.29 mmol) was suspended in anhydrous tetrahydrofuran (1 mL) in an oven-dried flask under a nitrogen atmosphere. A solution of 1-(4-(2-(dimethylamino)ethoxy)phenyl)-2-phenylhexan-1-one (58.0 mg, 0.17 mmol) in anhydrous tetrahydrofuran (1 mL) was added dropwise at room temperature. The resulting mixture was allowed to stir at room temperature for 2 days. The reaction was then quenched with 1N aqueous hydrochloric acid and then made basic by careful addition of saturated aqueous sodium bicarbonate. The mixture was extracted with ethyl acetate (2×5 mL). The combined organic layers were dried over anhydrous magnesium sulfate and concentrated on a rotary evaporator. The resulting residue was purified by reversed-phase chromatography (C-18 column, gradient of acetonitrile in water with 0.1% formic acid) to provide 50.0 mg (86%) of the desired product as a white solid. $^1$H NMR (400 MHz, MeOD) δ 7.87 (d, J=8.7 Hz, 2H), 7.29 (m, 5H), 6.99 (d, J=8.6 Hz, 2H), 4.70 (m, 1H), 4.31 (t, J=5.3 Hz, 2H), 3.58 (t, J=5.3 Hz, 2H), 2.98 (s, 6H), 2.83 (m, 1H), 2.1.56 (m, 6H), 0.80 (t, J=6.3 Hz, 3H); MS (ESI) (m/z) 323.2 (M−H$_2$O)$^+$.

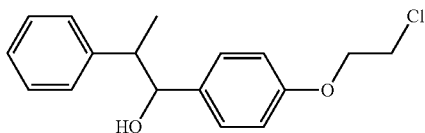

Step 5: (Z)—N,N-Dimethyl-2-(4-(2-phenylhex-1-en-1-yl)phenoxy)ethan-1-amine trifluoroacetate: 1-(4-(2-(Dimethylamino)ethoxy)phenyl)-2-phenylhexan-1-ol (50.0 mg, 0.15 mmol.) was suspended in ethanol (1 mL) and concentrated aqueous hydrochloric acid (0.125 mL) was added. The mixture was stirred at reflux for 2 hours and then at room temperature overnight. The reaction mixture was cooled and concentrated on a rotary evaporator. The resulting residue was purified by reversed-phase chromatography twice (C-18 column, gradient of acetonitrile in water with 0.1% trifluoroacetic acid) to provide 8.2 mg (17%) of the trifluoroacetate salt of the desired product as a white solid. $^1$H NMR (400 MHz, MeOD) δ 7.27 (d, J=8.8 Hz, 2H), 7.05 (m, 5H), 6.73 (d, J=8.8 Hz, 2H), 6.43 (s, 1H), 4.26 (t, J=5.3 Hz, 2H), 3.54 (t, J=5.2 Hz, 2H), 2.52 (t, J=6.2 Hz, 2H), 1.39-1.36 (m, 4H), 0.91 (t, J=7.0 Hz, 3H); MS (ESI) (m/z) 323.2 (M+H)$^+$.

Example 5: Synthesis of (Z)-1-(2-(4-(2-phenylprop-1-en-1-yl)phenoxy)ethyl)pyrrolidine (MC150262)

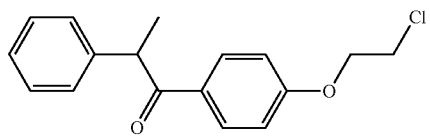 [SMILES: CC(C(=O)c1ccc(OCCCl)cc1)c1ccccc1]

Step 1—1-(4-(2-Chloroethoxy)phenyl)-2-phenylpropan-1-one: To a stirred solution of 2-phenylpropanoic acid (77.6 g, 516.6 mmol) in trifluoroacetic anhydride (85 mL, 600.0 mmol) cooled in an ice-water bath was added (2-chloroethoxy)benzene (96.8 mL, 633.4 mmol). After addition was complete the ice-water bath was removed and the reaction mixture was allowed to come up to room temperature and stir for 24 hours. The resulting mixture was carefully poured into water (500 mL) in an Erlenmeyer flask and the side of the flask was scratched with a glass rod until crystallization began. The crude solid product was collected by vacuum filtration, washed with water and dried in vacuo over P$_2$O$_5$. Recrystallization from light petroleum ether (bp 80-100° C.) afforded 84.0 g (54%) of the desired product as an off-white solid. $^1$H NMR (400 MHz, CDCl$_3$) δ 7.88 (d, J=9.0 Hz, 2H), 7.25 (m, 5H), 6.95 (d, J=9.0 Hz, 2H), 4.55 (q, J=6.7 Hz, 1H), 4.19 (t, J=5.8 Hz, 2H), 3.73, (t, J=5.8 Hz, 2H), 1.44 (d, J=6.6 Hz, 3H); MS (ESI) (m/z) 289.1/291.1 (M+H)$^+$.

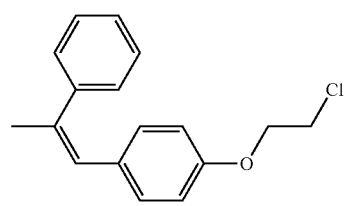 [SMILES: C/C(=C/c1ccc(OCCCl)cc1)c1ccccc1]

Step 2: 1-(4-(2-Chloroethoxy)phenyl)-2-phenylpropan-1-ol: Lithium aluminum hydride (140.0 mg, 3.7 mmol) was suspended in anhydrous tetrahydrofuran (50 mL) in an oven-dried flask under a nitrogen atmosphere. Then a solution of 1-(4-(2-chloroethoxy)phenyl)-2-propan-1-one (625.0 mg, 2.2 mmol) in anhydrous tetrahydrofuran (25 mL) was added dropwise at room temperature. The resulting mixture was allowed to stir at room temperature for 2 days. The reaction was then quenched with 1N aqueous hydrochloric acid and extracted with ethyl acetate (2×25 mL). The combined organic layers were dried over anhydrous magnesium sulfate and concentrated on a rotary evaporator to afford 581.0 mg (91%) of the desired product as a white solid that was used without further purification. $^1$H NMR (400 MHz, CDCl$_3$) δ 7.86 (d, J=8.8 Hz, 2H), 7.26-7.08 (m, 5H), 6.77 (d, J=8.8 Hz, 2H), 4.63 (d, J=7.4 Hz, 1H), 4.22 (t, J=5.8 Hz, 2H), 3.69 (t, J=5.8 Hz, 2H), 2.62 (m, 1H), 1.10 (d, J=7.4 Hz, 3H); MS (ESI) (m/z) 272.1/274.1 (M−H$_2$O)$^+$.

Step 3: (Z)-1-(2-Chloroethoxy)-4-(2-phenylprop-1-en-1-yl)benzene: 1-(4-(2-Chloroethoxy) phenyl)-2-phenylpropan-1-ol (100.0 mg, 0.34 mmol) was suspended in a mixture of ethanol (15 mL) and concentrated HCl (4.0 mL). The stirred mixture was stirred at reflux for 2 hours and then stirred overnight at room temperature. The reaction mixture was concentrated on a rotary evaporator and purified by chromatography on silica gel (ethyl acetate/hexane) to afford 75 mg of a yellow solid that contained both E and Z isomers. The desired Z isomer (17.0 mg, 17%) was obtained by reversed-phase chromatography (gradient of acetonitrile in water with 0.1% trifluoroacetic acid). $^1$H NMR (400 MHz, CDCl$_3$) δ 7.45 (d, J=8.2 Hz, 2H), 7.27 (m, 5H), 6.88 (d, J=8.3 Hz, 2H), 6.51 (s, 1H), 4.23 (t, J=5.7 Hz, 2H), 3.79 (t, J=5.8 Hz, 2H), 1.99 (s, 3H). MS (ESI) (m/z) 273.1/275.1 (M+H)$^+$.

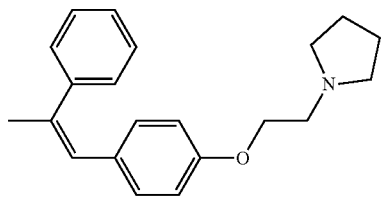 [SMILES: C/C(=C/c1ccc(OCCN2CCCC2)cc1)c1ccccc1]

Step 4: (Z)-1-(2-(4-(2-Phenylprop-1-en-1-yl)phenoxy) ethyl)pyrrolidine (Example 5): To a suspension of (Z)-1-(2-chloroethoxy)-4-(2-phenylprop-1-en-1-yl)benzene (10.3 mg, 0.05 mmol) in ethanol (0.75 mL) was added pyrrolidine (90.0 μL, 1.08 mmol,). The resulting reaction mixture was stirred at reflux for 12 hours. The reaction was cooled to room temperature and concentrated on a rotary evaporator. The resulting residue was purified by chromatography on silica gel (methanol/acetate with 0.1% NH$_4$H) to afford 13.1 mg of the desired product as a yellow solid. (Yield 85%) $^1$H NMR (400 MHz, CDCl$_3$) δ 7.42 (d, J=8.55 Hz, 2H), 7.28 (m, 2H), 7.18 (m, 3H), 6.87 (d, J=8.56 Hz, 2H), 6.32 (s, 1H), 4.20 (t, J=5.67 Hz, 2H), 2.86 (t, J=5.58 Hz, 2H), 2.64 (m, 4H), 2.56 (s, 3H), 1.72 (m, 4H); MS (ESI) (m/z) 308.2 (M+H)$^+$.

Example 6: Synthesis of (Z)—N,N-Dimethyl-2-(4-(2-(4-nitrophenyl)but-1-en-1-yl)phenoxy) ethan-1-amine (MC260001)

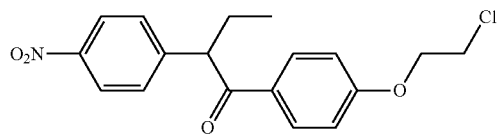 [SMILES: CCC(C(=O)c1ccc(OCCCl)cc1)c1ccc([N+](=O)[O-])cc1]

Step 1: 1-(4-(2-Chloroethoxy)phenyl)-2-(4-nitrophenyl) butan-1-one: 2-(4-Nitrophenyl) butanoic acid (1.66 g, 7.9 mmol) was dissolved in trifluoroacetic anhydride (1.1 mL, 7.9 mmol), then (2-chloroethoxy)benzene (1.0 ml, 7.2 mmol) was added dropwise. The resulting mixture was allowed to stir at room temperature overnight. The reaction mixture was poured into saturated aqueous sodium bicarbonate solution (50 mL) and extracted with ethyl acetate (2×50 mL). The combined organic phases were dried over anhydrous magnesium sulfate and concentrated on a rotary evaporator. The resulting residue was purified by chromatography on silica gel (ethyl acetate/hexane) to afford 1.49 g (59%) of the desired compound as a white solid. $^1$H NMR (400 MHz, CDCl$_3$) δ 8.21 (d, J=8.8 Hz, 2H), 7.96 (d, J=8.9 Hz, 2H), 7.51 (d, J=8.8 Hz, 2H), 6.93 (d, J=9.0 Hz, 2H), 4.56 (t, J=7.3 Hz, 1H), 4.28 (t, J=5.8 Hz 2H), 3.83 (t, J=5.8 Hz, 2H), 2.26 (m, 1H), 1.78 (m, 1H), 0.94 (t, J=7.4 Hz, 3H); MS (ESI) (m/z) 348.1/350.1 (M+H)$^+$.

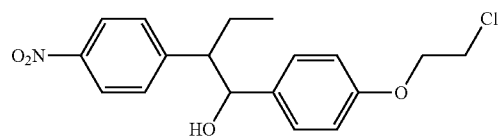

Step 2: 1-(4-(2-Chloroethoxy)phenyl)-2-(4-nitrophenyl) butan-1-ol: 1-(4-(2-Chloroethoxy)phenyl)-2-(4-nitrophenyl) butan-1-one (1.01 g, 2.9 mmol) was dissolved in dry tetrahydrofuran (28 mL) in an oven-dried flask under a nitrogen atmosphere, then lithium aluminum hydride (185.9 mg, 4.9 mmol) was added to the solution portion wise. The resulting mixture was allowed to stir at room temperature overnight. The reaction mixture was quenched with Rochelle's salt solution and then extracted with ethyl acetate (2×25 mL). The organic layers were combined, dried over anhydrous magnesium sulfate and concentrated on a rotary evaporator. Purification of the resulting residue by chromatography on silica gel (ethyl acetate/hexane) afforded 468.5 mg (43%) of the desired product as a yellow solid. (43%). $^1$H NMR (400 MHz, CDCl$_3$) δ 8.10 (d, J=8.7 Hz, 2H), 7.14 (m, 5H), 6.81 (d, J=8.6 Hz, 2H), 4.73 (d, J=7.5 Hz, 1H), 4.17 (t, J=5.9 Hz, 2H), 3.75 (t, J=5.8 Hz, 2H), 2.79 (m, 1H), 1.53 (m, 2H), 0.61 (t, J=7.4 Hz, 3H); MS (ESI) (m/z) 331.1/333.1 (M–H$_2$O)$^+$.

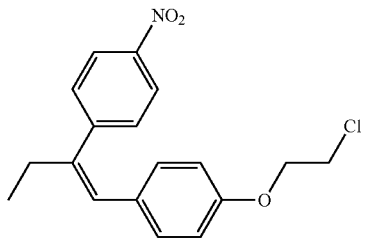 [SMILES: CC/C(=C/c1ccc(OCCCl)cc1)c1ccc([N+](=O)[O-])cc1]

Step 3: (Z)-1-(2-Chloroethoxy)-4-(2-(4-nitrophenyl)but-1-en-1-yl)benzene: 1-(4-(2-Chloroethoxy)phenyl)-2-(4-nitrophenyl)butan-1-one (351.5 mg, 1.0 mmol) was suspended in ethanol (5 mL), then concentrated hydrochloric acid (1.25 mL) was added. The resulting mixture was heated to 120° C. and stirred for 30 minutes. The reaction was cooled to room temperature and concentrated on a rotary evaporator. Purification of the resulting residue by chromatography on silica gel (ethyl acetate/hexane) afforded 72.9 mg (22%) of the desired product as a yellow solid. $^1$H NMR (400 MHz, CDCl$_3$) δ 8.08 (d, J=8.8 Hz, 2H), 7.24 (d, J=8.7 Hz, 2H), 6.68 (d, J=8.6 Hz, 2H), 6.59 (d, J=8.8 Hz, 2H), 6.43 (s, 1H), 4.08 (t, J=6.0 Hz, 2H), 3.69 (t, J=5.9 Hz, 2H), 2.46 (m, 2H), 0.98 (t, J=7.4 Hz, 3H); MS (ESI) (m/z) 332.1/334.7 (M+H)$^+$.

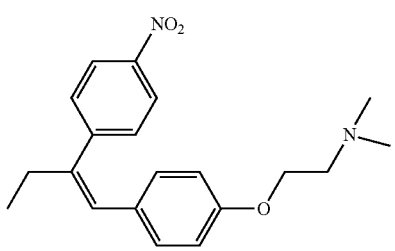 [SMILES: CC/C(=C/c1ccc(OCCN(C)C)cc1)c1ccc([N+](=O)[O-])cc1]

Step 4: (Z)—N,N-Dimethyl-2-(4-(2-(4-nitrophenyl)but-1-en-1-yl)phenoxy)ethan-1-amine: (Z)-1-(2-Chloroethoxy)-

4-(2-(4-nitrophenyl)but-1-en-1-yl)benzene (42.5 mg, 0.1 mmol) was suspended in 40% aqueous dimethylamine (2.0 mL). The reaction was stirred at 100° C. and stirred for 1 hour. The reaction mixture was cooled to room temperature and then concentrated on a rotary evaporator. The resulting residue was purified by reversed-phase chromatography (C-18 column, gradient of acetonitrile in water with 0.1% formic acid) to afforded 22.3 mg (51%) of the desired product as a yellow oil. ¹H NMR (400 MHz, CDCl₃) δ 8.08 (d, J=8.8 Hz, 2H), 7.23 (d, J=8.7 Hz, 2H), 6.76 (d, J=8.6 Hz, 2H), 6.56 (d, J=8.76 Hz, 2H), 6.43 (s, 1H), 4.21 (t, J=5.8 Hz, 2H), 3.44 (t, J=5.9 Hz, 2H), 2.38 (q, J=7.3 Hz, 2H), 0.98 (t, J=7.4 Hz, 3H); MS (ESI) (m/z) 341.2 (M+H)⁺.

Example 7: (Z)—N,N-Dimethyl-2-(4-(2-(4-chlorophenyl)but-1-en-1-yl)phenoxy)ethan-1-amine (MC260001)

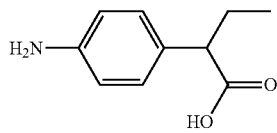

Step 1: 2-(4-Aminophenyl)butanoic acid: 2-(4-nitrophenyl)butanoic acid (10.0 g, 47.8 mmol) and palladium over carbon (0.25 g) were suspended in methanol (100 mL). The mixture was stirred at r.t. under 1 atmosphere of hydrogen overnight. The resulting mixture was filtered through Celite. The Celite was washed with methanol (50 mL) and the combined organic phases were concentrated on a rotary evaporator. Water (200 mL) was added and the reaction mixture was recrystallized. Cooling in an ice bath afforded 5.8 g (68%) of the desired product as a pink solid that was collected by vacuum filtration and dried in vacuo. ¹H NMR (400 MHz, DMSO) δ 11.88 (s, 1H), 6.73 (d, J=8.4 Hz, 2H), 6.31 (d, J=8.4 Hz, 2H), 4.77 (s, 2H), 2.98 (t, J=7.5 Hz, 1H), 1.68 (m, 1H), 1.39 (m, 1H), 0.62 (t, J=7.3 Hz 3H); MS (ESI) (m/z) 202.1 (M+Na)⁺.

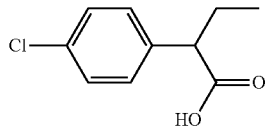

Step 2 2-(4-Chlorophenyl) butanoic acid: 2-(4-Aminophenyl)butanoic acid (358.4 mg, 2.0 mmol) was dissolved in concentrated hydrochloric acid (3 mL) by using sonication. The solution was cooled to 0° C. (ice/salt bath) for 5 min and then a solution of sodium nitrite (205.0 mg, 3.9 mmol) in water (1.5 mL) was added to the cooled solution dropwise over 30 minutes at a rate that kept the internal temperature of the reaction below 0° C. A solution of copper(I) chloride (396.0 mg, 4.0 mmol) in concentrated hydrochloric acid (3 mL) was cooled to 4° C. (ice/water bath) and then added to the reaction mixture dropwise at a rate that maintained the internal temperature of the reaction below 5° C. The resulting mixture was stirred at 0° C. for 2 hours, then allowed to come up to room temperature and stirred overnight. A yellow precipitate had formed, which was collected by vacuum filtration, washed with cold water and dried in vacuo to afford 289.6 mg (73%) of the desired product as a yellow solid. ¹H NMR (400 MHz, DMSO-d6) δ 12.39 (s, 1H), 7.35 (m, 4H), 3.47 (d, J=6.9 Hz, 1H), 1.95 (m, 1H), 1.64 (m, 1H), 0.82 (t, J=7.1 Hz, 3H). MS (ESI) (m/z) 221.0/223.0 (M+Na)⁺.

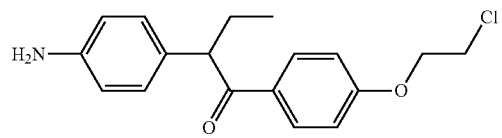

Step 3: 2-(4-Aminophenyl)-1-(4-(2-chloroethoxy)phenyl)butan-1-one: 2-(4-Aminophenyl) butanoic acid (397.3 mg, 2.0 mmol) was suspended with stirring in trifluoroacetic anhydride (277.4 uL, 2.0 mmol). Then (2-chloroethoxy)benzene (252.4 uL, 1.8 mmol) was added dropwise and the resulting mixture was stirred at room temperature overnight. The reaction was quenched with saturated sodium bicarbonate solution (5 mL) and extracted with ethyl acetate (2×15 mL). The combined organic layers were dried over anhydrous magnesium sulfate and concentrated on a rotary evaporator. The resulting residue was purified by reverse-phased chromatography (C-10 column, gradient of acetonitrile in water with 0.1% formic acid) to afford 297.1 mg (49%) of the desired product as a yellow solid. ¹H NMR (400 MHz, MeOD) δ 7.99 (d, J=8.9 Hz, 2H), 7.28 (m, 4H), 6.96 (d, J=8.9 Hz, 2H), 4.58 (t, J=7.2 Hz, 1H), 4.27 (t, J=5.5 Hz, 2H), 3.84 (t, J=5.5 Hz, 2H), 2.11 (m, 1H), 1.78 (m, 1H), 0.88 (t, J=7.3 Hz 3H); MS (ESI) (m/z) 318.1/320.1 (M+H)⁺.

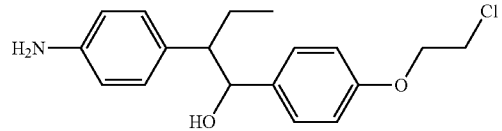

Step 4: 2-(4-Aminophenyl)-1-(4-(2-chloroethoxy)phenyl)butan-1-ol: 1-(4-(2-Chloroethoxy) phenyl)-2-(4-chlorophenyl)butan-1-one (287.1 mg, 0.9 mmol) was dissolved in dry tetrahydrofuran (14.5 mL) in an oven-dried flask under a nitrogen atmosphere, then a solution of lithium aluminum hydride in tetrahydrofuran (1M, 1.5 mL, 1.5 mmol) was added to the solution dropwise. The resulting mixture was allowed to stir at room temperature overnight under a nitrogen atmosphere. The reaction mixture was quenched with Rochelle's salt solution and then extracted with ethyl acetate (2×25 mL). The combined organic layers were dried over anhydrous magnesium sulfate and concentrated on a rotary evaporator. The desired product (249.3 mg, 87%) was isolated as a yellow solid and used without further purification. ¹H NMR (400 MHz, CDCl₃) δ 7.24 (d, J=8.4 Hz, 2H), 7.15 (d, J=8.6 Hz, 2H), 7.08 (d, J=8.4 Hz, 2H), 6.81 (d, J=8.7 Hz, 2H), 4.61 (d, J=8.1 Hz, 1H), 4.17 (t, J=5.9 Hz, 2H), 3.75 (t, J=5.8 Hz, 2H), 2.60 (m, 1H), 1.40 (m, 2H), 0.58 (t, J=7.4 Hz, 3H); MS (ESI) (m/z) 301.1/303.1 (M−H₂O)⁺.

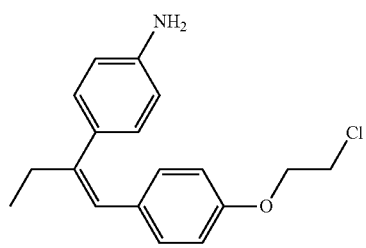 [SMILES: CC/C(=C/c1ccc(OCCCl)cc1)c1ccc(N)cc1]

Step 5: (Z)-1-(2-Chloroethoxy)-4-(2-(4-nitrophenyl)but-1-en-1-yl)benzene: 1-(4-(2-Chloro ethoxy)-phenyl)-2-(4-chlorophenyl)butan-1-ol (117.9 mg, 0.37 mmol) was dissolved in toluene (5 mL), then oven-dried 3A molecular sieves (100 mg) was added followed by anhydrous p-toluenesulfonic acid (74.0 mg, 0.04 mmol). The resulting mixture was stirred at 120° C. for 2 hours. The reaction mixture was cooled to room temperature, filtered to remove the molecular sieves and concentrated on a rotary evaporator. Purification of the resulting residue with reversed-phase chromatography (C-18 column, gradient of acetonitrile in water with 0.1% formic acid) afforded 66.1 mg (59%) of the desired product as a yellow solid. $^1$H NMR (400 MHz, MeOD) δ 7.20 (d, J=8.8 Hz, 2H), 7.01 (d, J=8.7 Hz, 2H), 6.74 (d, J=8.5 Hz, 2H), 6.57 (d, J=8.4 Hz, 2H), 6.33 (s, 1H), 4.04 (t, J=5.3 Hz, 2H), 3.69 (t, J=5.4 Hz, 2H), 2.39 (q, J=7.5 Hz, 2H), 0.93 (t, J=7.4 Hz, 3H); MS (ESI) (m/z) 302.1/304.1 (M+H)$^+$.

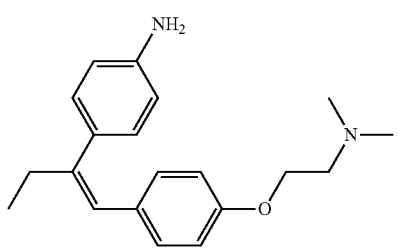 [SMILES: CC/C(=C/c1ccc(OCCN(C)C)cc1)c1ccc(N)cc1]

Step 6: (Z)—N,N-Dimethyl-2-(4-(2-(4-aminophenyl)but-1-en-1-yl)phenoxy)ethan-1-amine: (Z)-1-chloro-4-(1-(4-(2-chloroethoxy)phenyl)but-1-en-2-yl)benzene (26.7 mg, 0.09 mmol) was suspended in 40% aqueous dimethylamine (1.8 mL). The reaction was stirred at 100° C. for 3 hours. The reaction mixture was cooled to room temperature and then concentrated on a rotary evaporators The residue was purified by reversed-phase chromatography (gradient of acetonitrile in water with 0.1% formic acid) to afforded 4.7 (17%) mg of the desired product as a yellow oil. $^1$H NMR (400 MHz, MeOD) δ7.18 (d, J=8.5 Hz, 2H), 7.00 (d, J=8.4 Hz, 2H), 6.79 (d, J=8.7 Hz, 2H), 6.66 (d, J=8.8 Hz, 2H), 6.36 (s, 1H), 4.15 (t, J=4.96, 2H), 3.44 (t, J=4.96, 2H), 2.85 (s, 6H), 2.43-2.37 (m, 2H), 0.93 (t, J=7.4 Hz, 3H); MS (ESI) (m/z) 311.2 (M+H)$^+$.

Example 8: Synthesis of N,N-Dimethyl-2-(4-(2-phenylbutyl)phenoxy)ethan-1-amine trifluoroacetate (MC210155)

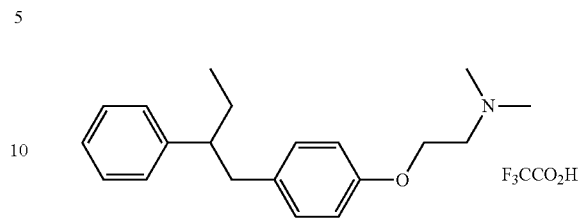

N,N-Dimethyl-2-(4-(2-phenylbutyl)phenoxy)ethan-1-amine trifluoroacetate: The mixture of E and Z isomers from Example 1, Step 3 (118.0 mg, 0.4 mmol.), Step 3 were dissolved in a mixture of methanol (5 mL) and ethanol (5 mL) with warming. The solution was cooled to room temperature and then 20 mg of 10% palladium on carbon was added and the reaction was allowed to stir at room temperature under 1 atmosphere of hydrogen for 24 hours. The reaction mixture was filtered through Celite to remove the catalyst. The Celite was washed with methanol and the combined organic filtrates were concentrated on a rotary evaporator. The resulting residue was purified by reversed-phase chromatography (gradient of acetonitrile in water with 0.1% TFA) to afford 98 mg (60%) of the trifluoroacetate salt of the desired product as a yellow solid. $^1$H NMR (400 MHz, CDCl$_3$) δ 7.18 (d, J=8.8 Hz, 2H), 7.02 (m, 5H), 6.63 (d, J=8.6 Hz, 2H), 4.22 (t, J=5.4 Hz, 2H), 3.42 (t, J=5.5 Hz, 2H), 2.88 (s, 6H), 2.74 (d, J=6.9 Hz, 2H), 2.55 (m, 1H), 1.67 (m, 1H), 1.44 (nm, 1H), 0.69 (t, J=7.3 Hz, 3H); MS (ESI) (m/z) 298.2 (M+H)$^+$.

Example 9: Synthesis of (E)-N,N-Dimethyl-2-(4-(1-phenylbut-1-en-2-yl)phenoxy)ethan-1-amine (MC210163)

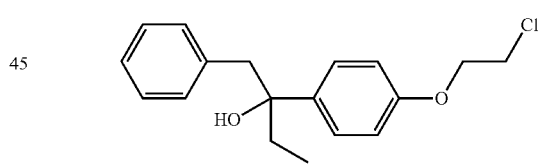

Step 1: 2-(4-(2-Chloroethoxy)phenyl)-1-phenylbutan-2-ol: 1-(4-(2-Chloroethoxy)phenyl)-2-phenylethan-1-one (Example 4, Step 1, 550.0 mg, 2.0 mmol) was dissolved in anhydrous tetrahydrofuran (10 mL) in an oven-dried flask under a nitrogen atmosphere. Ethylmagnesium bromide solution in diethyl ether (3 M, 607.0 μL, 2.0 mmol) was added at room temperature and the resulting mixture was stirred at reflux overnight. The reaction mixture was concentrated on a rotary evaporator and the resulting residue was purified by chromatography on silica gel (ethyl acetate/hexane) to afford 540.0 mg (89%) of the desired product as a yellow solid $^1$H NMR (400 MHz, CDCl$_3$) δ 7.89 (d, J=8.7 Hz, 2H), 7.15 (m, 5H), 6.88 (d, J=8.8 Hz, 2H), 4.15 (t, J=5.9 Hz, 2H), 3.74 (t, J=5.8 Hz, 2H), 3.01 (m, 2H), 1.87 (m, 1H), 1.75 (m, 1H), 0.68 (t, J=7.4 Hz, 3H); MS (ESI) (m/z) 286.81288.1 (M–H$_2$O)$^+$.

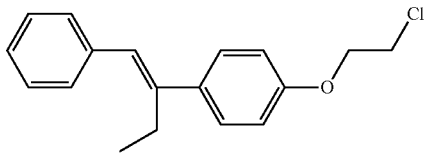 [SMILES: CC/C(=C\c1ccccc1)c1ccc(OCCCl)cc1]

Step 2: (E)-1-(2-Chloroethoxy)-4-(1-phenybut-1-en-2-yl) benzene: 2-(4-(2-Chloroethoxy) phenyl)-1-phenylbutan-2-ol (640.0 mg, 2.0 mmol.) was dissolved in acetonitrile (10 mL) and cooled in an ice bath for 10 minutes. Iodine (50.0 mg, 0.2 mmol) was added to the mixture and the reaction was allowed to stir and warm up to room temperature overnight. The reaction was concentrated on a rotary evaporator and the resulting residue was purified by reversed-phase chromatography (gradient of acetonitrile in water with 0.1% trifluoroacetic acid) and recrystallized from ethanol to afford 100.0 mg (17%) of the desired product as a white solid. $^1$H NMR (400 MHz, CDCl$_3$) δ 7.94 (d, J=8.7 Hz, 2H), 7.44 (d, J=6.68 Hz, 2H), 7.22 (m, 5H), 6.94 (d, J=8.8 Hz, 2H), 6.66 (s, 1H), 4.29 (t, J=5.9 Hz, 2H), 3.86 (t, J=5.9 Hz, 2H), 2.73 (q, J=7.4 Hz, 2H), 1.08 (t, J=7.4 Hz, 3H); MS (ESI) (m/z) 287.1/289.1 (M+H)$^+$.

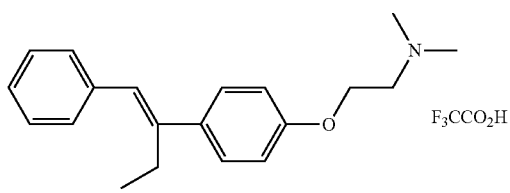

Step 3: (E)-N,N-dimethyl-2-(4-(1-phenylbut-1-en-2-yl)phenoxy)ethan-1-amine trifluoroacetate: (E)-1-(2-Chloroethoxy)-4-(1-phenylbut-1-en-2-yl)benzene (45.0 mg, 0.16 mmol) was suspended in 40% aqueous dimethylamine (2 mL) and stirred at reflux overnight. The reaction mixture was cooled to room temperature and then concentrated on a rotary evaporator. The resulting residue was purified by reversed-phase chromatography (C-18 column, gradient of acetonitrile in water with 0.1% trifluoroacetic acid) to provide 60.0 mg (93%) of the trifluoroacetate salt of the desired product as a white solid. $^1$H NMR (400 MHz, MeOD) δ 7.48 (d, J=8.8 Hz, 2H), 7.30 (m, 5H), 7.05 (d, J=8.8 Hz, 2H), 6.67 (s, 1H), 4.39 (t, J=5.5 Hz, 2H), 3.62 (t, J=5.5 Hz, 2H), 3.02 (s, 6H), 2.73 (q, J=7.5 Hz, 2H), 1.04 (t, J=7.4 Hz, 3H); MS (ESI) (m/z) 296.2 (M+H)$^+$.

Example 10: Synthesis of (E)-N,N-dimethyl-2-(4-(1-phenylbut-1-en-2-yl)phenoxy)ethan-1-amine (MC210164)

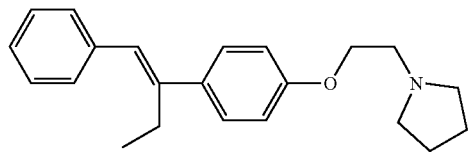 [SMILES: CC/C(=C\c1ccccc1)c1ccc(OCCN2CCCC2)cc1]

Step 1: (E)-1-(2-(4-(1-Phenylbut-1-en-2-yl)phenoxy) ethyl)pyrrolidine (Example 10): (E)-1-(2-Chloroethoxy)-4-(1-phenylbut-1-en-2-yl)benzene (Example 9, Step 2, 36.0 mg, 0.13 mmol) and pyrrolidine (0.25 mL, 3 mmol) were dissolved in ethanol (2 mL) and stirred at reflux for 24 hours. The reaction mixture was cooled to room temperature and then concentrated on a rotary evaporator. The resulting residue purified by chromatography on silica gel (methanol/ethyl acetate) to afford 18.1 mg (45%) of the desired product as a white solid. $^1$H NMR (400 MHz, MeOD) δ 7.48 (d, J=8.8 Hz, 2H), 7.28 (m, 5H), 6.96 (d, J=8.8 Hz, 2H), 6.65 (s, 1H), 4.17 (t, J=5.6 Hz, 2H), 2.96 (t, J=5.6 Hz, 2H), 2.70 (m, 6H), 1.86 (m, 4H), 1.05 (t, J=7.5 Hz, 3H); MS (ESI) (m/z) 322.2 (M+H)$^+$.

Example 11: Synthesis of 1-(4-(2-Dimethylaminoethoxy)-phenyl)-3-methyl-2-phenylbutan-1-one (MC150224)

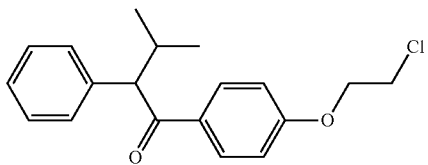 [SMILES: CC(C)C(C(=O)c1ccc(OCCCl)cc1)c1ccccc1]

Step 1: 1-(4-(2-Chloroethoxy)phenyl)-3-methyl-2-phenyl-buran-1-one: A stirred suspension of 60% sodium hydride in mineral oil (1.12 g, 28.0 mmol) in anhydrous tetrahydrofuran (50 mL) in an oven dried flask under a nitrogen atmosphere was cooled in an ice-water bath. To the cooled mixture was added 1-(4-(2-chloroethoxy)phenyl)-2-phenylethan-1-one (Example 4, Step 1, 5.52 g, 20.0 mmol) portionwise over 10 minutes. The resulting reaction mixture was stirred under cooling for 30 minutes and then iodoethane (1.9 mL, 24.0 mmol) was added. The ice bath was removed and the stirred reaction was allowed to come up to room temperature and then stirred for 3 hours. The mixture was partitioned between diethyl ether (75 mL) and water (75 mL). The aqueous layer was extracted twice more with diethyl ether (2×50 mL). The combined organic layers were washed with water (50 mL), dried over anhydrous magnesium sulfate and concentrated on a rotary evaporator. The resulting residue was purified by chromatography on silica gel (dichloromethane/hexane) and the desired compound (5.5 g, 89%) was obtained as a white solid after recrystallization from light petroleum ether (bp 80-100° C.). $^1$H NMR (400 MHz, CDCl$_3$) δ 7.96 (d, J=8.9 Hz, 2H), 7.22 (m, 5H), 6.88 (d, J=9.0 Hz, 2H), 4.38 (d, J=9.3 Hz, 1H), 4.24 (t, J=5.8 Hz, 2H), 3.81 (t, J=5.8 Hz, 2H), 2.50 (m, 1H), 0.92, (d, J=6.6 Hz, 3H), 0.64 (d, J=6.8 Hz, 3H); MS (ESI) (m/z) 317.2/319.2 (M+H)$^+$.

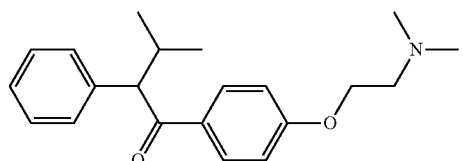

Step 2: 1-(4-(2-Dimethylaminoethoxy)-phenyl)-3-methyl-2-phenylbutan-1-one (Example 11): 1-(4-(2-Chloroethoxy)phenyl)-3-methyl-2-phenyl-buran-1-one (100.0 mg, 0.32 mmol) was suspended in 40% aqueous dimethylamine (4 mL) and stirred at reflux for 12 hours. The reaction mixture was cooled and then concentrated on a rotary evaporator. The resulting residue was purified by chromatography on silica gel (methanol/ethyl acetate with 0.1% concentrated ammonium hydroxide) to provide 74.0 mg (71%) of the desired product as a yellow solid. $^1$H NMR (400 MHz, CDCl$_3$) δ 7.91 (d, J=9.1 Hz, 2H), 7.23 (m, 5H), 6.80 (d, J=9.0 Hz, 2H), 4.33 (t, J=5.5 Hz, 2H), 4.07 (d, J=9.4 Hz, 1H), 3.38 (t, J=5.6 Hz, 2H), 2.53 (m, 1H), 2.41 (s, 6H), 0.92 (d, J=6.4 Hz, 3H), 0.65 (d, J=6.3 Hz, 3H); MS (ESI) (m/z) 326.2 (M+H)$^+$.

Example 12: Synthesis of 1-(4-(2-(Dimethylamino)ethoxy)phenyl)-2-phenylhexan-1-one (MC150235)

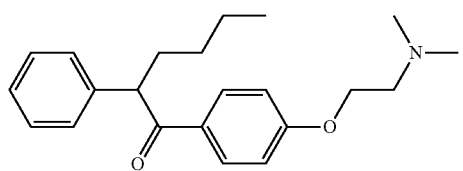 [SMILES: CCCCC(C(=O)c1ccc(OCCN(C)C)cc1)c1ccccc1]

1-(4-(2-(Dimethyl amino)-ethoxy)phenyl)-2-phenylethan-1-one (80.4 mg, 0.28 mmol) and n-butylbromide (33.7 µL, 0.31 mmol) dissolved in anhydrous tetrahydrofuran were treated with 60% sodium hydride in mineral oil (22.7 mg, 0.57 mmol) at 0° C. under a nitrogen atmosphere. The reaction was then stirred at reflux for 30 minutes, followed by stirring overnight at room temperature. The reaction was quenched by careful addition of methanol and concentrated to dryness on a rotary evaporator. The residue was partitioned between water (10 mL) and ethyl acetate (15 mL). The aqueous layer was extracted eiyh ethyl acetate (2×10 mL) and the combined organic layers were dried over anhydrous magnesium sulfate and concentrated on a rotary evaporator. The resulting residue was purification by reversed-phase chromatography (C-18 column, gradient of acetonitrile in water with 0.1% formic acid) to afford 58 ng (54%) of the desired product as a yellow solid. $^1$H NMR (400 MHz, MeOD) δ 8.06 (d, J=8.8 Hz, 2H), 7.28 (m, 5H), 7.05 (d, J=8.9 Hz, 2H), 4.68 (t, J=5.9 Hz, 1H), 4.43 (d, J=5.7 Hz, 2H), 3.65 (d, J=5.7 Hz, 2H), 3.00 (s, 6H), 2.18 (m, 1H), 1.77 (m, 1H), 1.38 (m, 4H), 0.88 (t, J=6.4 Hz, 3H); MS (ESI) (m/z) 340.2 (M+H)$^+$.

Example 13: Synthesis of 1-(4-(2-(Dimethylamino)ethoxy)pyrenyl)-5-methyl-2-phenylhexan-1-one (MC150268)

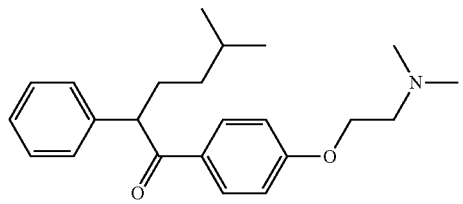 [SMILES: CC(C)CCC(C(=O)c1ccc(OCCN(C)C)cc1)c1ccccc1]

A stirred suspension of 60% sodium hydride in mineral oil (22.5 mg, 0.56 mmol) in anhydrous tetrahydrofuran (5 mL) in an oven dried flask under a nitrogen atmosphere was cooled in an ice-water bath. To the cooled mixture was added 1-(4-(2-dimethylaminoethoxy)phenyl)-2-phenylethan-1-one (Example 4, Step 2, 113.4 mg, 0.4 mmol). The resulting reaction mixture was stirred under cooling for 30 minutes and then iodoethane (38 uL, 0.48 mmol) was added. The ice bath was removed and the stirred reaction was allowed to come up to room temperature and then stirred for 3 hours. The mixture was partitioned between diethyl ether (10 mL) and water (10 mL). The aqueous layer was extracted twice more with diethyl ether (10 mL). The combined organic layers were washed with water (30 mL), dried over anhydrous magnesium sulfate and concentrated on a rotary evaporator. The resulting residue was purified by chromatography on silica gel (dichloromethane/hexane) to provide 73.5 mg (52%) of the desired product as a light yellow solid. $^1$H NMR (400 MHz, CDCl$_3$) δ 7.98 (d, J=9.2 Hz, 2H), 7.34 (m, 5H), 6.90 (d, J=9.1 Hz, 2H), 4.63 (t, J=7.8 Hz, 1H), 4.25 (t, J=5.8 Hz, 2H), 3.04 (t, J=6.7 Hz, 2H), 2.72 (s, 6H), 2.20 (m, 1H), 1.80 (m, 1H), 1.57 (m, 1H), 1.26 (m, 1H), 1.09 (m, 1H), 0.85 (d, J=5.9 Hz, 6H); MS (ESI) (m/z) 354.2 (M+H)$^+$.

Example 14 Synthesis of 1-(4-(2-(Dimethylamino)ethoxy)phenyl)-4-methyl-2-phenylpentan-1-one (MC150269)

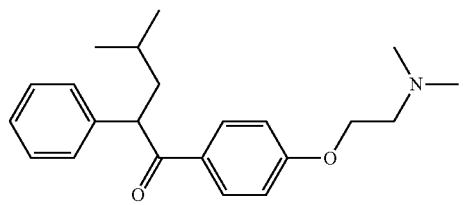 [SMILES: CC(C)CC(C(=O)c1ccc(OCCN(C)C)cc1)c1ccccc1]

Step 1: 1-(4-(2-(Dimethylamino)ethoxy)phenyl)-4-methyl-2-phenylpentan-1-one (Example 14): A stirred suspension of 60% sodium hydride in mineral oil (16.8 mg, 0.42 mmol) in anhydrous tetrahydrofuran (5 mL) in an oven dried flask under a nitrogen atmosphere was cooled in an ice-water bath. To the cooled mixture was added 1-(4-(2-dimethylaminoethoxy)phenyl)-2-phenylethan-1-one (Example 4, Step 2, 85.0 mg, 0.3 mmol). The resulting reaction mixture was stirred under cooling for 30 minutes and then iodoethane (29 uL, 0.36 mmol) was added. The ice bath was removed and the stirred reaction was allowed to come up to room temperature and then stirred for 3 hours. The mixture was partitioned between diethyl ether (10 mL) and water (10 mL). The aqueous layer was extracted twice more with diethyl ether (10 mL). The combined organic layers were washed with water (30 mL), dried over anhydrous magnesium sulfate and concentrated on a rotary evaporator. The resulting residue was purified by chromatography on silica gel (dichloromethane/hexane) to provide 47.0 mg (46%) of the desired product as a yellow solid. $^1$H NMR (400 MHz, CDCl$_3$) δ 7.95 (d, J=9.0 Hz, 2H), 7.30 (m, 5H), 6.88 (d, J=8.9 Hz, 2H), 4.47 (t, J=7.5 Hz, 1H), 4.31 (t, J=5.6 Hz, 2H), 3.24 (t, J=5.5 Hz, 2H), 2.72 (s, 6H), 2.10 (m, 1H), 1.75 (m, 1H), 1.50 (m, 1H), 0.95 (d, 6H); MS (ESI) (m/z) 340.2 (M+H)$^+$.

Example 15: Synthesis of 1-(4-(2-(dimethylamino)ethoxy)phenyl)-2-(2-vinylphenyl)hexan-1-one (MC150279)

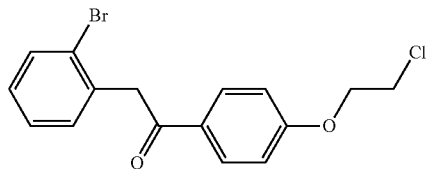 [SMILES: O=C(Cc1ccccc1Br)c1ccc(OCCCl)cc1]

Step 1: 2-(2-Bromophenyl)-1-(2-chloroethoxy)phenyl)ethan-1-one: 2-Bromophenyl acetic acid (5.0 g, 23.3 mmol,) was suspended in trifluoroacetic anhydride (13.5 mL, 93.5 mmol). Chloroethyoxylbenzene (3.3 mL, 23.3 mmol) was added to the stirred suspension dropwise. The resulting mixture was allowed to stir overnight at room temperature. The reaction was quenched with 40% aqueous sodium hydroxide solution and then extracted with ethyl acetate (2×20 mL). The combined organic layers were dried over anhydrous magnesium sulfate and concentrated on a rotary evaporator. The resulting residue was purified by chromatography on silica gel (ethyl acetate/hexane) to afford 5.98 g (73%) of the desired product as a light orange solid. $^1$H NMR (400 MHz, CDCl$_3$) δ 8.05 (d, J=8.9 Hz, 2H), 7.60 (d, J=8.5 Hz, 1H), 7.24 (m, 2H), 7.18 (m, 1H), 6.96 (d, J=9.0 Hz, 2H), 4.40 (s, 2H), 4.37 (t, J=5.5 Hz, 2H), 3.88 (t, J=5.7 Hz, 2H); MS (ESI) (m/z) 354.0/356.0 (M+H)$^+$.

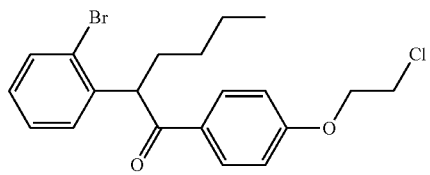 [SMILES: CCCCC(C(=O)c1ccc(OCCCl)cc1)c1ccccc1Br]

Step 2: 2-(2-Bromophenyl)-1-(4-(2-chloroethoxy)phenyl)hexan-1-one: A stirred suspension of 60% sodium hydride in mineral oil (52.0 mg, 1.3 mmol) in anhydrous tetrahydrofuran (5 mL) in an oven dried flask under a nitrogen atmosphere was cooled in an ice-water bath. To the cooled mixture was added 2-(2-bromophenyl)-1-(2-chloroethoxy)phenyl)ethan-1-one (460.0 mg, 1.3 mmol) portionwise over 10 minutes. The resulting reaction mixture was stirred under cooling for 30 minutes and then 1-bromobutane (225.6 uL, 1.3 mmol) was added. The ice bath was removed and the stirred reaction was allowed to come up to room temperature and then stirred for 3 hours. The mixture was partitioned between diethyl ether (15 mL) and water (15 mL). The aqueous layer was extracted twice more with diethyl ether (15 mL). The combined organic layers were washed with water (15 mL), dried over anhydrous magnesium sulfate and concentrated on a rotary evaporator. The resulting residue was purified by chromatography on silica gel (dichloromethane/hexane) and the desired compound (404.5 g, 75%) was obtained as a white solid after recrystallization from light petroleum ether (bp 80-100° C.). $^1$H NMR (400 MHz, CDCl$_3$) δ 8.00 (d, J=8.8 Hz, 2H), 7.59 (d, J=8.3 Hz, 1H), 7.26 (m, 2H), 7.16 (m 1H), 6.89 (d, J=8.9 Hz, 2H), 5.03 (t, J=7.5 Hz, 1H), 4.28 (t, J=5.5 Hz, 2H), 4.17 (t, J=5.4 Hz, 2H), 2.17 (m, 1H), 1.73 (m, 1H), 1.60 (m, 3H), 1.39 (m, 1H), 0.91 (t, J=6.8 Hz, 2H); MS (ESI) (m/z) 411.1/413.1 (M+H)$^+$.

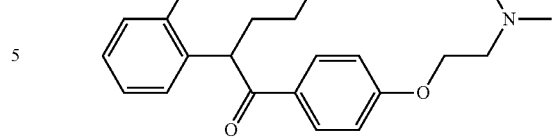

Step 3: 2-(2-bromophenyl)-1-(4-(2-(dimethylamino)ethoxy)phenyl)hexan-1-one: 2-(2-Bromophenyl)-1-(4-(2-chloroethoxy)phenyl)hexan-1-one (100.0 mg, 0.24 mmol) was suspended in 40% aqueous dimethylamine (4 mL) and stirred at reflux for 12 hours. The reaction mixture was cooled and then concentrated on a rotary evaporator. The resulting residue was purified by chromatography on silica gel (dichloromethane/hexane) to provide 85.3 mg (85%) of the desired product as a light orange solid. $^1$H NMR (400 MHz, CDCl$_3$) δ 7.93 (d, J=9.0 Hz, 2H), 7.48 (d, J=8.4 Hz, 1H), 7.23 (m, 2H), 7.08 (m, 1H), 6.88 (d, J=9.0 Hz, 2H), 5.02 (t, J=7.3 Hz, 1H), 4.22 (t, J=5.9 Hz, 2H), 2.95 (t, J=5.8 Hz, 2H), 2.49 (s, 6H), 2.16 (m, 1H), 1.73 (m, 1H), 1.40 (m, 3H), 1.26 (m, 1H), 0.89 (t, J=6.6 Hz, 3H); MS (ESI) (m/z) 418.1/420.1 (M+H)$^+$.

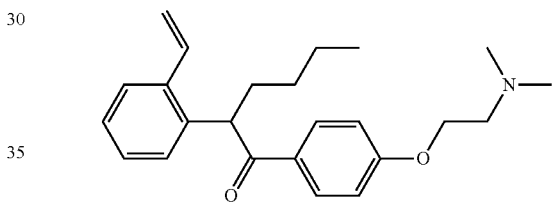

Step 4: 1-(4-(2-(dimethylamino)ethoxy)phenyl)-2-(2-vinylphenyl)hexan-1-one (Example 15): A stirred mixture of 2-(2-bromophenyl)-1-(4-(2-(dimethylamino)ethoxy)phenyl)hexan-1-one (70.0 mg, 0.17 mmol), 4,4,5,5-tetramethyl-2-vinyl-1,3,2-dioxaborolane (77.5 mg, 0.50 mmol), potassium carbonate (115.5 mg, 0.84 mmol), tetrakis(triphenylphosphine)palladium(0) (6.0 mg, 0.005 mmol), tetrahydrofuran (1.0 mL) and water (1.0 mL) in a closed vial under a nitrogen atmosphere was heated at 65° C. for 9 hours. The cooled reaction mixture was diluted with chloroform (30 mL) and water (30 mL), shaken and the layers were separated. The aqueous layer was extracted with an additional 20 mL portion of chloroform. The combined organic layers were dried over anhydrous magnesium sulfate and concentrated on a rotary evaporator. The resulting residue was purified by chromatography on silica gel (dichloromethane/hexane) to provide 20.7 mg (35%) of the desired product as a yellow oil that hardened upon standing. $^1$H NMR (400 MHz, CDCl$_3$) δ 8.00 (d, J=8.8 Hz, 2H), 7.51 (d, J=8.3 Hz, 1H), 7.38 (m, 2H), 7.14 (m, 1H), 6.88 (d, J=8.9 Hz, 2H), 6.68 (dd, J1=17.9 Hz, J2=11.2 Hz, 1H), 5.71 (d, J=17.8 Hz, 1H), 5.22 (d, J=11.1 Hz, 1H), 4.49 (t, J=7.4 Hz, 1H), 4.32 (t, J=5.9 Hz, 2H), 3.18 (t, J=5.8 Hz, 2H), 2.66 (s, 6H), 2.18 (m, 1H), 1.82 (m, 1H), 1.31 (m, 3H), 1.27 (m, 1H), 0.87 (t, J=6.4 Hz, 3H); MS (ESI) (m/z) 366.2 (M+H)$^+$.

Example 16: Synthesis of 1-(4-(2-(dimethylamino) ethoxy)phenyl)-2-(2-ethylphenyl)hexan-1-one (MC150281)

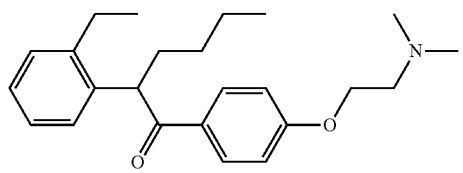

Step 1: 1-(4-(2-(dimethylamino)ethoxy)phenyl)-2-(2-ethylphenyl)hexan-1-one (Example 16): A solution of 1-(4-(2-(dimethylamino)ethoxy)phenyl)-2-(2-vinylphenyl)hexan-1-one (Example 15, 15.0 mg, 0.04 mmol) in methanol (5 mL) was treated with 10% palladium on carbon (2 mg) and then hydrogenated on a Parr shaker at 40 psig for 18 hours. The reaction mixture was filtered through Celite and the Celite was washed with methanol (10 mL). The combined organic fractions were concentrated on a rotary evaporator and the resulting residue was chromatographed on silica gel (dichloromethane/hexane) to provide 13.5 mg (92%) of the desired compound as a yellow oil that hardened upon standing. $^1$H NMR (400 MHz, CDCl$_3$) δ 7.96 (d, J=8.8 Hz, 2H), 7.49 (m, 1H), 7.30 (m, 2H), 7.08 (m, 1H), 6.85 (d, J=8.9 Hz, 2H), 4.48 (t, J=7.7 Hz, 1H), 4.27 (t, J=5.9 Hz, 2H), 3.15 (t, J=5.9 Hz, 2H), 2.41 (s, 6H), 2.00 (m, 1H), 1.62 (m, 1H), 1.60 (m, 6H), 1.00 (t, J=7.2 Hz, 3H), 0.69 (t, J=7.0 Hz, 3H); MS (ESI) (m/z) 368.3 (M+H)$^+$.

Example 17: Synthesis of 1-(4-(2-(dimethylamino) ethoxy)phenyl)-2-(2-prop-1-en-2-yl)phenyl)hexan-1-one (MC150278)

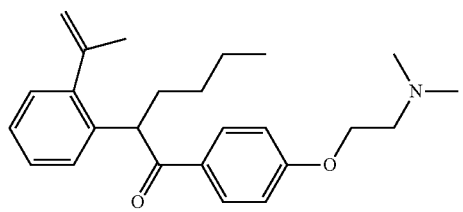 [SMILES: C=C(C)c1ccccc1C(CCCC)C(=O)c1ccc(OCCN(C)C)cc1]

Step 1—1-(4-(2-(dimethylamino)ethoxy)phenyl)-2-(2-prop-1-en-2-yl)phenyl)hexan-1-one (Example 17): A stirred mixture of 2-(2-bromophenyl)-1-(4-(2-(dimethylamino) ethoxy)phenyl)hexan-1-one (Example 15, Step 3, 150.0 mg, 0.36 mmol), 4,4,5,5-tetramethyl-2-(propo-1-en-2-yl)-1,3,2-dioxaborolane (185.4 mg, 1.13 mmol), potassium carbonate (260.0 mg, 1.89 mmol), tetrakis(triphenylphosphine)palladium(0) (13.6 mg, 0.02 mmol), tetrahydrofuran (5.0 mL) and water (5.0 mL) in a closed pressure flask under a nitrogen atmosphere was heated at 65° C. for 9 hours. The cooled reaction mixture was diluted with chloroform (70 mL) and water (70 mL), shaken and the layers were separated. The aqueous layer was extracted with an additional 50 mL portion of chloroform. The combined organic layers were dried over anhydrous magnesium sulfate and concentrated on a rotary evaporator. The resulting residue was purified by chromatography on silica gel (dichloromethane/hexane) to provide 64.1 mg (47%) of the desired product as a yellow solid. $^1$H NMR (400 MHz, CDCl$_3$) δ 7.80 (d, J=8.7 Hz, 2H), 7.47 (d, J=8.3 Hz, 1H), 7.26 (m, 2H), 7.06 (m, 1H), 6.74 (d, J=8.7 Hz, 2H), 5.32 (s, 1H), 4.90 (s, 1H), 4.34 (t, J=7.3 Hz, 1H), 4.18 (t, J=5.5 Hz, 2H), 3.07 (t, J=5.4 Hz, 2H), 2.52 (s, 6H), 2.02 (m, 1H), 1.65 (m, 1H), 1.14 (m, 4H), 0.72 (t, J=7.1 Hz, 3H); MS (ESI) (m/z) 380.3 (M+H)$^+$.

Example 18 Synthesis of 1-(4-(2-(Dimethylamino) ethoxy)phenyl)-2-(2-isopropylphenyl)hexan-1-one (MC150280)

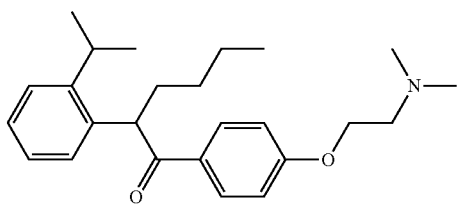 [SMILES: CCCCC(C(=O)c1ccc(OCCN(C)C)cc1)c1ccccc1C(C)C]

Step 1—1-(4-(2-(Dimethylamino)ethoxy)phenyl)-2-(2-isopropylphenyl)hexan-1-one (Example 18): A solution of 1-(4-(2-(dimethylamino)ethoxy)phenyl)-2-(2-prop-1-en-2-yl)phenyl)hexan-1-one (Example 17, 35.0 mg, 0.09 mmol) in methanol (15 mL) was treated with 10% palladium on carbon (5 mg) and then hydrogenated on a Parr shaker at 40 psig for 18 hours. The reaction mixture was filtered through Celite and the Celite was washed with methanol (25 mL). The combined organic fractions were concentrated on a rotary evaporator and the resulting residue was chromatographed on silica gel (dichloromethane/hexane) to provide 30.7 mg (90%) of the desired compound as a yellow oil that hardened upon standing. $^1$H NMR (400 MHz, CDCl$_3$) δ 7.94 (d, J=8.9 Hz, 2H), 7.56 (d, J=8.4 Hz, 1H), 7.40 (m, 2H), 7.16 (m, 1H), 6.91 (d, J=9.0 Hz, 2H), 4.47 (t, J=7.2 Hz, 1H), 4.30 (t, J=5.6 Hz, 2H), 3.19 (t, J=5.5 Hz, 2H), 2.83 (m, 1H), 2.41 (s, 6H), 2.20 (m, 1H), 1.30 (m, 1H), 1.33 (m, 4H), 1.20 (d, J=6.9 Hz, 6H), 0.86 (d, J=7.2 Hz, 3H); MS (ESI) (m/z) 382.3 (M+H)$^+$.

Example 19: Synthesis of 1-(4-(2-(dimethylamino) ethoxy)phenyl)-2-(2-isopropylphenyl)-4-methylpentan-1-one (MC-260013)

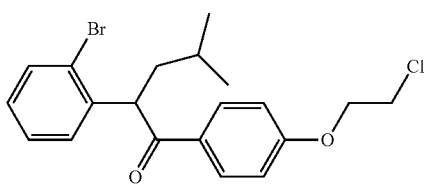 [SMILES: CC(C)CC(C(=O)c1ccc(OCCCl)cc1)c1ccccc1Br]

Step 1—2-(2-Bromophenyl)-1-(4-(2-chloroethoxy)phenyl)-4-methylpentan-1-one. A stirred suspension of 60% sodium hydride in mineral (160.0 mg, 4.0 mmol) and anhydrous tetrahydrofuran (5 mL) in an oven dried flask was cooled in an ice water bath under a nitrogen atmosphere. To the cooled mixture, 2-(2-bromophenyl)-1-(4-(2-chloroethoxy)phenyl)ethan-1-one (Example 15, Step 1, 460.0 mg, 1.30 mmol) was added portionwise over 5 minutes. The resulting mixture was stirred under cooling for 30 minutes and then 1-bromo-2-methylpropane (141 µL, 1.30 mmol) was added. The ice bath was removed and the resulting mixture was stirred at room temperature overnight, then stirred at 65° C. for 5 hours. The reaction mixture was partitioned between ethyl acetate and water. The aqueous layer was extracted twice more with ethyl acetate. The combined organic phases were dried anhydrous magnesium sulfate and concentrated on a rotary evaporator. The resulting residue was purified by chromatography on silica gel (dichloromethane/hexane) to afford the desired compound 70 mg, 13% yield) as a yellow solid. $^1$H NMR (400 MHz, MeOD) δ 8.01 (d, J=8.9 Hz, 2H), 7.64 (d, J=8.0, 1H), 7.27-7.21 (m, 2H), 7.15-7.11 (m, 1H), 7.51 (d, J=8.9 Hz, 2H), 5.22-5.19 (m, 1H), 4.31 (t, J=5.4 Hz, 2H), 3.87 (t, J=5.4 Hz, 2H), 2.13-2.07 (m, 1H), 1.62-1.57 (m, 1H), 1.53-1.46 (m, 1H), 1.00-0.95 (m, 6H); MS (ESI) (m/z) 409 (M+H)$^+$.

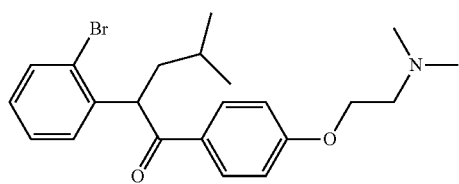 [SMILES: CC(C)CC(C(=O)c1ccc(OCCN(C)C)cc1)c1ccccc1Br]

Step 2—2-(2-Bromophenyl)-1-(4-(2-(dimethylamino)ethoxy)phenyl)-4-methylpentan-1-one. 2-(2-Bromophenyl)-1-(4-(2-chloroethoxy)phenyl)ethan-1-one (70.0 mg, 0.17 mmol) and dimethylamine (40% aqueous solution, 10 mL) were stirred at 100° C. for 12 hours. The cooled reaction mixture was concentrated on a rotary evaporator and the residue was purified by reversed phase chromatography (C-18 column, gradient of 10-100% acetonitrile in water with 0.1% formic acid) to afford 60.0 mg (84% yield) of the desired compound as a yellow wax. $^1$H NMR (400 MHz, MeOD) δ 8.01 (d, J=8.9 Hz, 2H), 7.64 (d, J=8.0 Hz, 1H), 7.26-7.19 (m, 2H), 7.13-7.08 (m, 3H), 5.22-5.19 (m, 1H), 4.43 (t, J=4.9 Hz, 2H), 3.62 (t, J=4.9 Hz, 2H), 2.99 (s, 6H), 2.15-2.03 (m, 1H), 1.62-1.57 (m, 1H), 1.53-1.47 (m, 1H), 1.00-0.95 (m, 6H); MS (ESI) (m/z) 420 (M+H)$^+$.

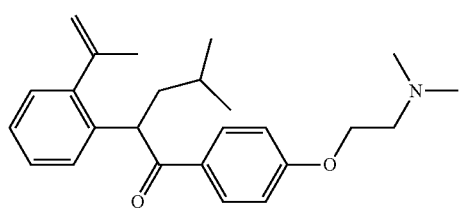 [SMILES: C=C(C)c1ccccc1C(CC(C)C)C(=O)c1ccc(OCCN(C)C)cc1]

Step 3—1-(4-(2-(Dimethylamino)ethoxy)phenyl)-4-methyl-2-(2-(prop-1-en-2-yl)phenyl)pentan-1-one. 2-(2-Bromophenyl)-1-(4-(2-(dimethylamino)ethoxy)phenyl)-4-methylpentan-1-one (60 mg, 0.14 mmol), 4,4,5,5-tetramethyl-2-(prop-1-en-2-yl)-1,3,2-dioxaborolane (0.1 mL, 0.53 mmol), potassium carbonate (6.0 mg, 0.04 mmol), tetrakis(triphenylphosphine)palladium(0) (4 mg, 0.003 mmol), water (1 mL) were mixed together and then heated at 120° C. for 20 minutes in a microwave reactor. The mixture was diluted with water (9 mL) and extracted with chloroform three times. The combined extracts were dried over anhydrous magnesium sulfate and concentrated on a rotary evaporator. The resulting residue was purified by reversed phase chromatography (C-18 column, gradient of 10-100% acetonitrile in water with 0.1% formic acid) to afford the desired product (22.8 mg, 44% yield) as a yellow solid. $^1$H NMR (400 MHz, MeOD) δ 7.98 (d, J=6.9 Hz, 2H), 7.30-7.27 (m, 1H), 7.20-7.14 (m, 3H), 7.08 (d, J=6.9 Hz, 2H), 5.43 (s, 1H), 5.09-5.07 (m, 1H), 4.92 (s, 1H), 4.43 (t, J=4.8 Hz, 2H), 3.62 (t, J=4.9 Hz, 2H), 2.96 (s, 6H), 2.30-2.23 (m, 1H), 2.14 (s, 3H), 1.61-1.32 (m, 2H), 1.00-0.93 (m, 6H); MS (ESI) (m/z) 380 (M+H)$^+$.

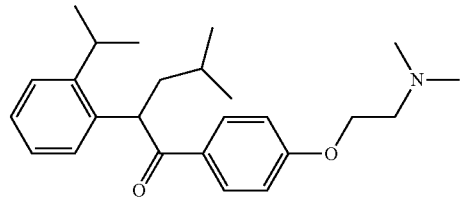 [SMILES: CC(C)CC(C(=O)c1ccc(OCCN(C)C)cc1)c1ccccc1C(C)C]

Step 4—1-(4-(2-(Dimethylamino)ethoxy)phenyl)-2-(2-isopropylphenyl)-4-methylpentan-1-one. 1-(4-(2-(Dimethylamino)ethoxy)phenyl)-4-methyl-2-(2-(prop-1-en-2-yl)phenyl)pentan-1-one (22.8 mg, 0.06 mmol) and palladium on carbon (4 mg) were mixed in 5 ml of methanol and then stir under 1 atm. hydrogen at room temperature for 2 days. The palladium on carbon was removed by filtration and the resulting solution was concentrated on a rotary evaporator. The resulting residue was purified by reversed phase chromatography to afford 3.45 mg (15% yield) expected product as a yellow solid (6.5%). $^1$H NMR (400 MHz, MeOD) δ 7.83 (d, J=7.00, 2H), 7.24 (d, J=7.67 Hz, 1H), 7.12-7.09 (m, 1H), 6.96-6.93 (m, 4H), 4.91-4.88 (m, 2H), 4.30 (t, J=5.0 Hz, 2H), 3.50 (t, J=4.9 Hz, 2H), 2.88 (s, 6H), 2.14-2.07 (m, 1H), 1.54-1.52 (m, 1H), 1.51-1.49 (m, 1H), 1.23 (d, J=6.80, 3H), 1.17 (d, J=6.80, 3H), 0.88-0.86 (m, 6H); MS (ESI) (m/z) 382 (M+H)$^+$.

Example 20: Synthesis of 1-(4-(2-(dimethylamino)ethoxy)phenyl)-2-(3-isopropylphenyl)-4-methylpentan-1-one (MC-260015)

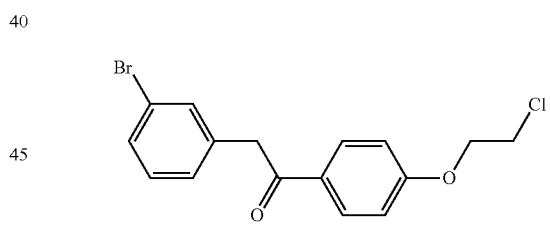

Step 1—2-(3-Bromophenyl)-1-(4-(2-chloroethoxy)phenyl)ethan-1-one. 3-Bromophenylacetic acid (4.0 g, 18.6 mmol) was dissolved in trifluoroacetic anhydride (3.6 mL, 25.9 mmol), then (2-chloroethoxy)benzene (2.56 mL, 18.6 mmol) was added dropwise. The resulting mixture was allowed to stir at room temperature overnight. The reaction mixture was quenched with saturated aqueous sodium bicarbonate solution and then extracted twice with ethyl acetate. The organic layers were combined, dried over anhydrous magnesium sulfate and then concentrated on a rotary evaporator. The resulting residue was purified by chromatography on silica gel to afford the desired product (5.46 g, 83% yield) as a yellow solid. $^1$H NMR (400 MHz, MeOD) δ 8.07 (d, J=8.9 Hz, 2H), 7.47-7.40 (m, 2H), 7.25-7.24 (m, 2H), 7.07 (d, J=8.9 Hz, 2H), 4.37-4.33 (m, 4H), 3.92-3.89 (m, 2H); MS (ESI) (m/z) 355 (M+H)$^+$.

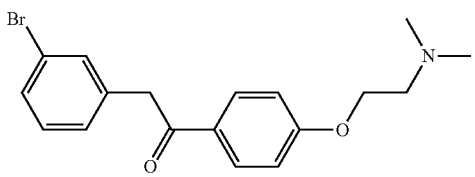 [SMILES: CN(C)CCOc1ccc(C(=O)Cc2cccc(Br)c2)cc1]

Step 2—2-(3-Bromophenyl)-1-(4-(2-(dimethylamino)ethoxy)phenyl)ethan-1-one. 2-(3-Bromophenyl)-1-(4-(2-chloroethoxy)phenyl)ethan-1-one (4.0 g, 11.3 mmol) and dimethylamine (40% aqueous solution, 42 mL) were stirred at 100° C. for 4 hours. The cooled reaction mixture was concentrated on a rotary evaporator and the residue was purified by chromatography on silica gel (dichloromethane/hexane) to afford the desired product (3.79 g, 68.5% yield) as a yellow wax. $^1$H NMR (400 MHz, CDCl$_3$) δ 7.35 (d, J=8.9 Hz, 2H), 7.31-7.30 (m, 2H), 7.13-7.11 (m, 2H), 6.89 (d, J=8.9 Hz, 2H), 4.13-4.04 (m, 4H), 2.73 (t, J=5.2 Hz, 2H), 2.31 (s, 6H); MS (ESI) (m/z) 364 (M+H)$^+$.

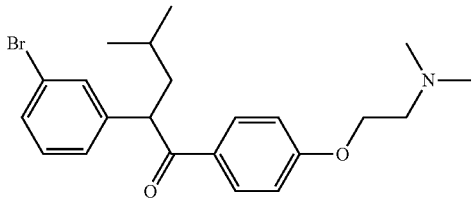 [SMILES: CC(C)CC(C(=O)c1ccc(OCCN(C)C)cc1)c1cccc(Br)c1]

Step 3—2-(3-Bromophenyl)-1-(4-(2-(dimethylamino)ethoxy)phenyl)-4-methylpentan-1-one. A stirred suspension of 60% sodium hydride in mineral (290 mg, 7.25 mmol) and anhydrous tetrahydrofuran (18 mL) in an oven dried flask was cooled in an ice water bath under a nitrogen atmosphere. To the cooled mixture, 2-(3-bromophenyl)-1-(4-(2-(dimethylamino)ethoxy)phenyl)ethan-1-one (800 mg, 2.21 mmol) was added portionwise over 5 minutes. The resulting mixture was stirred under cooling for 30 minutes and then 1-bromo-2-methylpropane (1.5 mL, 13.8 mmol) was added. The ice bath was removed and the resulting mixture was stirred at room temperature overnight. The reaction mixture was partitioned between ethyl acetate and water then extracted twice more with ethyl acetate. The combined organic layers were dried over anhydrous magnesium sulfate and concentrated on a rotary evaporator. The resulting residue was purified by chromatography on silica gel (dichloromethane/hexane) to afford the desired product (255 mg, 27% yield) as a yellow solid. $^1$H NMR (400 MHz, CDCl$_3$) δ 7.91 (d, J=8.9 Hz, 2H), 7.26-7.24 (m, 1H), 7.17-7.16 (m, 1H), 7.10 (s, 1H), 7.08-7.06 (M, 1H), 6.85 (d, J=8.9 Hz, 2H), 4.52 (t, J=7.4 Hz, 1H), 4.22 (s, 2H), 2.96-2.90 (m, 2H), 2.48 (s, 6H), 2.02-1.95 (m, 1H), 1.64-1.58 (m, 1H), 1.44-1.37 (m, 1H), 0.87-0.81 (m, 6H); MS (ESI) (m/z) 380 (M+H)$^+$.

Step 4—1-(4-(2-(Dimethylamino)ethoxy)phenyl)-4-methyl-2-(3-(prop-1-en-2-yl)phenyl)pentan-1-one. 2-(3-Bromophenyl)-1-(4-(2-(dimethylamino)ethoxy)phenyl)-4-methylpentan-1-one (255 mg, 0.69 mmol), 4,4,5,5-tetramethyl-2-(prop-1-en-2-yl)-1,3,2-dioxaborolane (0.6 mL, 3.18 mmol), potassium carbonate (500 mg, 3.33 mmol), tetrakis(triphenylphosphine)palladium(0) (30 mg, 0.026 mmol), water (2.5 mL), tetrahydrofuran (3 mL) were mixed and then heated at 120° C. for 15 min in a microwave reactor. The reaction mixture was diluted with water (24 mL) and extracted three times with chloroform. The combined organic layers were dried over anhydrous magnesium sulfate and concentrated on a rotary evaporator. The resulting rescue was purified by reversed phase chromatography (C-18 column, gradient of acetonitrile in water with 0.1% formic acid) to afford the desired product (143 mg, 62% yield) as a yellow solid. $^1$H NMR (400 MHz, MeOD) δ 7.91 (d, J=8.9 Hz, 2H), 7.34 (s, 1H), 7.14-7.12 (m, 3H), 6.89 (d, J=8.9 Hz, 2H), 5.22 (s, 1H), 4.96 (s, 1H), 4.69 (t, J=7.6 Hz, 1H), 4.07 (t, J=5.4 Hz, 2H), 2.74 (t, J=5.4 Hz, 2H), 2.28 (s, 6H), 2.00 (s, 3H), 1.95-1.81 (m, 1H), 1.60-1.53 (m, 1H), 1.41-1.34 (m, 1H), 0.86-0.79 (m, 6H); MS (ESI) (m/z) 380 (M+H)$^+$.

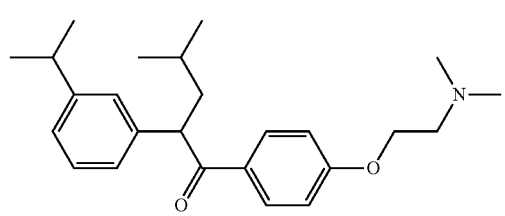 [SMILES: CC(C)CC(C(=O)c1ccc(OCCN(C)C)cc1)c1cccc(C(C)C)c1]

Step 5—1-(4-(2-(Dimethylamino)ethoxy)phenyl)-2-(3-isopropylphenyl)-4-methylpentan-1-one. 1-(4-(2-(Dimethylamino)ethoxy)phenyl)-4-methyl-2-(3-(prop-1-en-2-yl)phenyl)pentan-1-one (143 mg, 0.38 mmol) and palladium on carbon (15 mg) were mixed in 5 mL of methanol and then stirred under 1 atmosphere of hydrogen at room temperature for 2 days. The palladium on carbon was removed by filtration and the reaction mixture was concentrated on a rotary evaporator. The resulting residue was purified by reversed phase chromatography (C-18 column, gradient of acetonitrile in water with 0.1% formic acid) to afford the desired product (108 mg, 75%) as a yellow solid. $^1$H NMR (400 MHz, MeOD) δ 7.90 (d, J=8.7 Hz, 2H), 7.08-7.06 (m, 2H), 7.03-7.00 (m, 1H), 6.96-6.94 (m, 1H), 6.87 (d, J=8.7 Hz, 2H), 4.64 (t, J=7.3 Hz, 1H), 4.05 (t, J=5.4 Hz, 2H), 2.78-2.72 (m, 1H), 2.67 (t, J=5.4 Hz, 2H), 2.24 (s, 6H), 1.97-1.90 (m, 1H), 1.58-1.51 (m, 1H), 1.40-1.32 (m, 1H), 1.11-1.05 (m, 6H), 0.85-0.70 (m, 6H); MS (ESI) (m/z) 382 (M+H)$^+$.

Example 21: Synthesis of 2-(2-cyclopropylphenyl)-1-(4-(2-(dimethylamino)ethoxy)phenyl)-4-methyl-pentan-21-one (MC-290045)

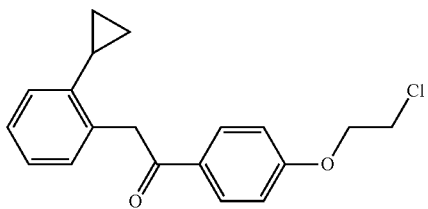 [SMILES: O=C(Cc1ccccc1C1CC1)c1ccc(OCCCl)cc1]

Step 1—1-(4-(2-chloroethoxy)phenyl)-2-(2-cyclopropylphenyl)ethanone. A mixture of 2-(2-bromophenyl)-1-(4-(2-chloroethoxy)phenyl)ethanone (Example 15, Step 1, 2.0 gm, 5.66 mmol), cyclopropylboronic acid (0.97 gm, 11.3 mmol), anhydrous potassium fluoride (1.08 gm, 18.6 mmol), bis(dibenzylidineacetone)palladium(0) (0.25 gm, 0.28 mmol) and tri-tert-butylphosphine (2.49 mL, 0.84 mmol) and anhydrous tetrahydrofuran (30 mL) were heated under a nitrogen atmosphere in a sealed vessel at 65° C. overnight (approx. 18 hours). The reaction mixture was cooled to room temperature and concentrated on a rotary evaporator. The residue was partitioned between chloroform and water. The aqueous layer was extracted twice more with chloroform. The combined organic layers were dried over anhydrous magnesium sulfate and concentrated on a rotary evaporator. The resulting residue was purified by chromatography on silica gel (hexane/ethyl acetate) to give the desired product as a yellow oil which precipitated as a yellow solid upon trituration (0.92 gm, 26% yield). $^1$H NMR (400 MHz, CDCl$_3$) δ 8.05 (d, J=8.9 Hz, 2H), 7.27-7.19 (m, 2H), 7.09 (m, 1H), 6.98 (d, J=8.9 Hz, 2H), 4.47 (s, 2H), 4.323 (t, J=5.8 Hz, 2H), 3.86 (t, J=5.8 Hz, 2H), 1.85 (m, 1H), 0.87 (m, 2H), 0.67 (m, 2H); MS (ESI) (m/z) 315 (M+H)$^+$.

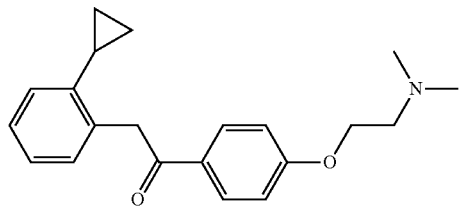 [SMILES: CN(C)CCOc1ccc(C(=O)Cc2ccccc2C2CC2)cc1]

Step 2—2-(2-Cyclopropylphenyl)-1-(4-(2-(dimethylamino)ethoxy)phenyl)ethanone. 1-(4-(2-Chloroethoxy)phenyl)-2-(2-cyclopropylphenyl)ethanone (0.84 g, 2.67 mmol) and dimethylamine (40% aqueous solution, 20 mL) were stirred at 100° C. overnight (approx. 18 hours). The reaction mixture was cooled to room temperature and extracted with four portions of diethyl ether. The combined organic layers were dried over anhydrous magnesium sulfate and concentrated on a rotary evaporator. The desired product (0.45 g, 52% yield) was obtained as a waxy yellow solid and was used without further purification. $^1$H NMR (400 MHz, CDCl$_3$) δ 8.03 (d, J=8.8 Hz, 2H), 7.30-7.20 (m, 3H), 7.15 (m, 1H), 6.98 (d, J=8.9 Hz, 2H), 4.47 (s, 2H), 4.19 (t, J=5.6 Hz, 2H), 2.83 (t, J=5.6 Hz, 2H), 2.41 (s, 6H), 1.83 (m, 1H), 0.87 (m, 2H), 0.66 (m, 2H); MS (ESI) (m/z) 324 (M+H)$^+$.

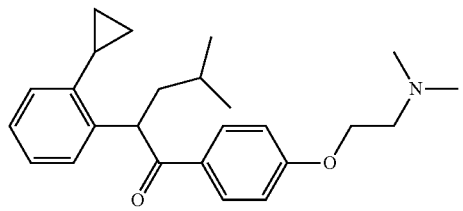 [SMILES: CC(C)CC(C(=O)c1ccc(OCCN(C)C)cc1)c1ccccc1C1CC1]

Step 3—2-(2-Cyclopropylphenyl)-1-(4-(2-(dimethylamino)ethoxy)phenyl)-4-methylpentan-21-one. A mixture of 2-(2-cyclopropylphenyl)-1-(4-(2-(dimethylamino)ethoxy)phenyl)ethanone (0.45 g, 1.38 mmol) and 1-bromo-2-methylpropane (0.20 mL, 1.84 mmol) in anhydrous tetrahydrofuran (10 mL) under a nitrogen atmosphere was treated with 60% sodium hydride in mineral oil (0.10 g, 2.5 mmolmmol) at room temperature. The resulting reaction mixture was heated at 55° C. under nitrogen overnight (approx. 18 hours). The next day another portion of 1-bromo-2-methylpropane (0.20 mL, 1.84 mmol) and 60% sodium hydride in mineral oil (0.10 gm, 2.5 mmol) were added and heating at 55° C. under nitrogen was continued another 24 hours. The resulting reaction mixture was cooled to room temperature and partitioned between ethyl acetate and saturated aqueous ammonium chloride solution. The aqueous layer was extracted twice with additional portions of ethyl acetate. The combined organic layers were dried over anhydrous magnesium sulfate and concentrated on a rotary evaporator. The resulting residue was purified by chromatography on a RediSep Rf Gold™ High Performance Amine Column (gradient of ethyl acetate in hexane) to provide the desired compound (0.10 g, 20% yield) as a yellow solid. $^1$H NMR (400 MHz, CDCl$_3$) δ 7.74 (d, J=8.9 Hz, 2H), 6.94 (m, 1H), 6.89-6.79 (m, 3H), 6.72 (d, J=8.9 Hz, 2H), 5.03 (m, 1H), 3.92 (t, J=5.7 Hz, 2H), 2.63 (t, J=5.6 Hz, 2H), 2.25 (s, 6H), 2.05 (m, 1H), 1.88 (m, 1H), 1.48 (m, 1H), 1.31 (m, 1H), 0.75 (m, 6H), 0.6 (m, 2H), 0.51 (m, 2H); MS (ESI) (m/z) 380 (M+H)$^+$.

Formulations

The present invention also relates to compositions or formulations which comprise the functionalized N,N-dialkylamino phenyl ethers according to the present invention. In general, the compositions of the present invention comprise an effective amount of one or more functionalized N,N-dialkylamino phenyl ethers and salts thereof according to the present invention which are effective for treating and preventing diseases and conditions that involve lysosomal storage dysfunction, including, for example, Gaucher's disease, Tay-Sachs disease, Sandhoffs diseae, Sandhoff-Jatzkewitz disease, Fabry disease, Niemann Pick disease Type C, Pompe diseae, type III A mucopolysaccharidosis, Sanfilippo syndrome, α-mannosidosis, GM1 gangliosidosis, and GM2 gangliosidosis; and one or more excipients. In addition, the compositions of the present invention comprise an effective amount of one or more functionalized N,N-dialkylamino phenyl ethers and salts thereof according to the present invention which are effective for treating and preventing diseases and conditions that involve misfolding of lysosomal related proteins and one or more excipients. Further, the compositions of the present invention comprise an effective amount of one or more functionalized N,N-dialkylamino phenyl ethers and salts thereof according to the present invention which are effective for treating and preventing Parkinson's disease and synucleinopathies dementia with Lewy bodies (DLB), pure autonomic failure (PAF), and multiple system atrophy (MSA). In addition, the compositions of the present invention comprise an effective amount of one or more functionalized N,N-dialkylamino phenyl ethers and salts thereof according to the present invention which are effective for treating and preventing fungal infections. Further, the compositions of the present invention comprise an effective amount of one or more functionalized N,N-dialkylamino phenyl ethers and salts thereof according to the present invention which are effective for treating and preventing diseases and conditions that involve calcium signaling dysfunction. Further, the compositions of the present invention comprise an effective amount of one or more functionalized N,N-dialkylamino phenyl ethers and salts thereof according to the present invention which are effective for treating and preventing diseases and conditions that involve β-glucocerebrosidase dysfunction. Further, the compositions of the present invention comprise an effective amount of one or more functionalized N,N-dialkylamino phenyl ethers and salts thereof according to the present invention which are effective for treating and preventing diseases and conditions that involve α-galactosidase A dysfunction. Further, the compositions of the present invention comprise an effective amount of one or more functionalized N,N-dialkylamino phenyl ethers and salts thereof according to the present invention which are effective for treating and preventing diseases and conditions that involve β-galactosidase dysfunction. Further, the compositions of the present invention comprise an effective amount of one or more functionalized N,N-dialkylamino phenyl ethers and salts thereof according to the present invention which are effective for treating and preventing diseases and conditions that involve β-hexosaminidase dysfunction. Further, the compositions of the present invention comprise an effective amount of one or more functionalized N,N-dialkylamino phenyl ethers and salts thereof according to the present invention which are effective for treating and preventing diseases and conditions that involve α-glucosidase dysfunction. Further, the compositions of the present invention comprise an effective amount of one or more functionalized N,N-dialkylamino phenyl ethers and salts thereof according to the present invention which are effective for treating and preventing diseases and conditions that involve N-acetylgalactosamine-4-sulfatase dysfunction. Further, the compositions of the present invention comprise an effective amount of one or more functionalized N,N-dialkylamino phenyl ethers and salts thereof according to the present invention which are effective for treating and preventing diseases and conditions that involve heparan sulfate acetyl-CoA dysfunction. Further, the compositions of the present invention comprise an effective amount of one or more functionalized N,N-dialkylamino phenyl ethers and salts thereof according to the present invention which are effective for treating and preventing diseases and conditions that involve α-glucosaminidine N-acetyltransferase dysfunction. Further, the compositions of the present invention comprise an effective amount of one or more functionalized N,N-dialkylamino phenyl ethers and salts thereof according to the present invention which are effective for treating and preventing diseases and conditions that involve galactocerebrosidase dysfunction. Further, the compositions of the present invention comprise an effective amount of one or more functionalized N,N-dialkylamino phenyl ethers and salts thereof according to the present invention which are effective for treating and preventing diseases and conditions that involve mucolipins 1 dysfunction. Further, the compositions of the present invention comprise an effective amount of one or more functionalized N,N-dialkylamino phenyl ethers and salts thereof according to the present invention which are effective for treating and preventing diseases and conditions that involve mucolipins 2 dysfunction. Further, the compositions of the present invention comprise an effective amount of one or more functionalized N,N-dialkylamino phenyl ethers and salts thereof according to the present invention which are effective for treating and preventing diseases and conditions that involve mucolipins 3 dysfunction.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, PA (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known therapeutic agents. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more functionalized N,N-dialkylamino phenyl ethers according to the present invention and one or more excipients; from about 0.01 mg to about 100 mg of one or more functionalized N,N-dialkylamino phenyl ethers according to the present invention and one or more excipients; and from about 0.1 mg to about 10 mg of one or more functionalized N,N-dialkylamino phenyl ethers according to the present invention; and one or more excipients.

Procedures

The following procedures can be utilized in evaluating and selecting compounds as therapeutic agents.

Phenotypic Assay: A phenotypic cellular assay utilizing lysosomal storage disorder (LSD) patient derived cells was developed to identify compounds with disease modifying activity to reverse or attenuate the disease phenotype to non-disease levels. The phenotypic assay was based on a functional readout we observed in cell lines derived from LSD disease patients reflective of the LSD diseased state. This functional readout of the LSD diseased state was developed into a high throughput screening assay.

Disruption of lysosomal calcium homeostasis has been linked to the pathophysiology of lysosomal storage disorders including Gaucher disease (Lloyd-Evans, E, Morgan A J, He X, Smith D A, Elliot-Smith E, Sillence D J, Churchill G C, Schuchman E H, Galione A, Platt F M. (2008) Niemann-Pick disease type C1 is a sphingosine storage disease that causes deregulation of lysosomal calcium. Nat Med. 14(11):1247-55. Lloyd-Evans E, Platt F M. (2011) Lysosomal Ca(2+) homeostasis: role in pathogenesis of lysosomal storage diseases. Cell Calcium. 50(2):200-205. Morgan, A J, Platt, F M, Lloyd-Evans, E and Galione, A (2011) Molecular mechanism of endolysosomal Ca2+ signaling in health and disease. Biochem. J. 439:349-374.). Calcium release from acidic lysosomal stores can be induced by addition of Gly-Phe-p-napthylamide (GPN), a substrate of cathepsin C, which upon hydrolysis, produces osmotic lysis of lysosomes and release of calcium specifically from lysosomal acidic stores into the cytosol (de la Mata M, Cotán D, Oropesa-Ávila M, Garrido-Maraver J, Cordero M D, Villanueva Paz M, Delgado Pavón A, Alcocer-Gómez E, de Lavera I, Ybot-González P, Paula Zaderenko A, Ortiz Mellet C, Garcia Fernández J M, Sánchez-Alcázar J A. Pharmacological chaperones and Coenzyme Q10 treatment improves mutant β-Glucocerebrosidase activity and mitochondrial function in neuronopathic forms of Gaucher Disease. Sci Rep. 2015 Jun. 5; 5:10903. Lockhart, D J. Treatment of Gaucher Disease with specific pharmacological chaperones and monitoring treatment using surrogate markers (2013) U.S. Pat. No. 8,399,525). The increase of intracellular calcium released from lysosomes can be detected with cell membrane permeable calcium sensitive indicators. In comparison to fibroblasts from wild-type, non-affected patients, fibroblasts derived from Gaucher disease, Tay-Sachs, Fabry and Nieman Pick Type C patients all exhibited a reduced release of calcium in response to GPN (FIG. 1). The reduction in lysosomal calcium release in comparison to normal, wild-type patient fibroblasts is a functional readout reflective of the LSD disease state and was further developed as the basis of a cellular, phenotypic assay to use for identifying compounds with activity to restore the LSD disease to normal.

Gaucher patient fibroblasts (Coreill Institute, GM08760) were cultured in EMEM with 15% FBS, 1% Pen/Strep at 37° C./5% $CO_2$. Wild-type patient fibroblasts (Coriell Institute, GM 005659) were used as a control cell line. Cells are plated with a MultiFlo dispenser (800 cells/well in 30 μL of complete growth media) in black/clear bottom 384-well plates and cultured for 24 hours at 37° C., 5% $CO_2$. Compounds of the disclosure are then added to the cells (12 point dose response curve, 150 nM to 30 uM final compound concentration using a 5.0 μL of a 7× stock solution (1.05 μM to 210 μM)) under sterile conditions and continued in culture for 72 hours at 37° C., 5% $CO_2$. For intracellular calcium measurements, media is removed and 20 μL of calcium dye mixture (Screen Quest™ Fluo-8 No Wash Calcium mix, ATT Bioquest) is added to each well, incubated for 30 minutes at 37° C., followed by 22° C. for 30 minutes. Changes in fluorescence intensity are monitored on the FDSS gCell fluorescence kinetic plate reader, (excitation, 480 nm, emission 540 nm) reading at 1 Hz for a 20 seconds baseline followed by a 5 minute recording after addition of 50 μM GPN. The data from each well were normalized with basal fluorescence by dividing the maximum fluorescence over the entire real time reading by the initial basal fluorescence. Results are expressed as peak fluorescence change in relative fluorescence units (RFU).

Figure 2:
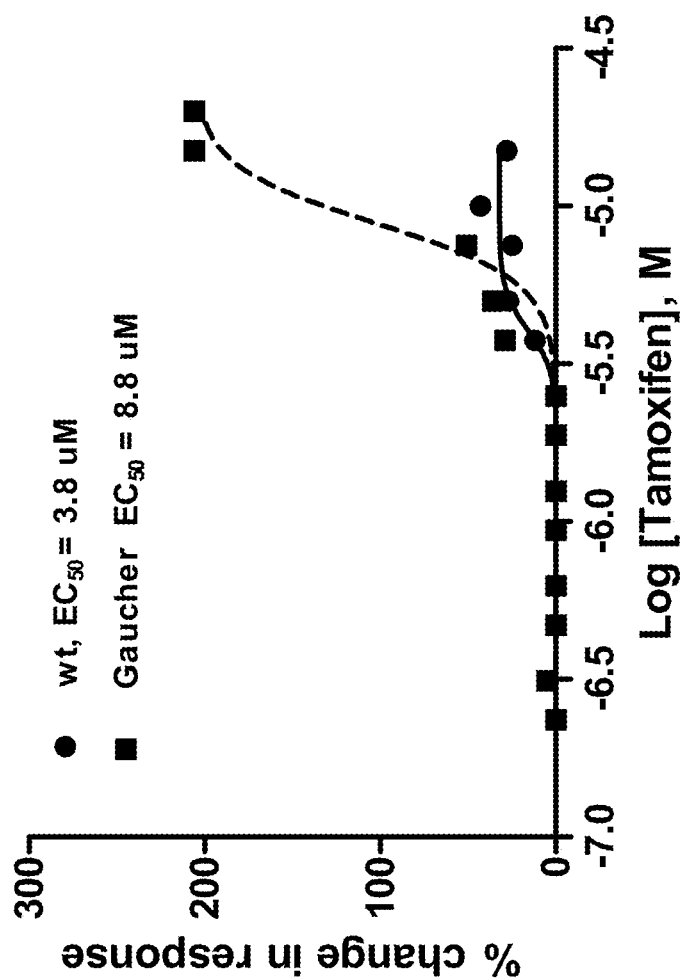
FIG. 2 is a chart depicting the dose response curves of Tamoxifen on GPN-induced release of calcium measured on Gaucher and wild Type patient fibroblasts.

Identification of Tamoxifen as active in reversing LSD disease phenotype: The Prestwick Chemical Library, a collection of 1200 known FDA approved drugs, was screened to identify compounds with activity to restore the LSD disease phenotype in Gaucher patient cells to normal levels. Cells (800 cells/well) were plated with a MultiFlo dispenser (BioTek) and cultured for 24 h at 37° C., 5% $CO_2$. The screening compounds were then added to cells under sterile conditions and continued in culture for 72 hours. Cells were loaded with Screen Quest™ Fluo-8 No Wash Calcium mix (ATT Bio) and analyzed for changes in response to GPN. The data from each well were normalized with basal fluorescence by dividing the maximum fluorescence over the entire real time reading by the initial basal fluorescence. Tamoxifen was identified as an active compound to increase lysosomal calcium signaling as a measure of disease phenotype reversal. The activity of Tamoxifien was confirmed in triplicate and the functional potency was determined on Gaucher patient and compared to wild type, normal patient cells. $EC_{50}$ and Hill slope values are determined using a four-parameter dose-response (variable slope) equation in GraphPad Prism. The % change in GPN response is calculated as the ratio of GPN response measured in the presence of drug/GPN response measured in the absence of drug X 100. Tamoxifen exhibited $EC_{50}=8.8\pm0.18$ μM and 200±50% increase in calcium response compared with 0.1% DMSO treated Gaucher patient cells. The maximal % change in GPN response is calculated as the ratio of GPN response measured in the presence of drug/GPN response measured in the absence of drug X 100. Tamoxifen also increased the GPN-induced response on wild type cells, $EC_{50}=4.0\pm0.38$ μM, however in comparison with Gaucher cells, the increase in GPN-induced calcium response was smaller (40+/−20%) (FIG. 2).

Determination of the activity, $EC_{50}$ and % maximal response of synthesized analogs measured in Gaucher patient cells: The functional potency ($EC_{50}$) and % maximal activation of compounds of the disclosure were measured in the GPN induced calcium assay on Gaucher patient cells. A 12-point dilution curve in triplicate was prepared from 10 mM compounds stocks in 100% DMSO and added to Gaucher cells. After 72 hours, cells were loaded with Screen Quest™ Fluo-8 No Wash Calcium mix (ATT Bio) and analyzed for changes in response to GPN. The data from each well were normalized with basal fluorescence by dividing the maximum fluorescence over the entire real time reading by the initial basal fluorescence. The maximal % change in GPN response is calculated as the ratio of GPN response measured in the presence of drug/GPN response measured in the absence of drug X 100.

TABLE 28

Functional potency ($EC_{50}$) and % maximal change in the GPN induced calcium release in Gaucher patient cells of representative compounds of the disclosure.

| Example | MC-number | Maximal % Change in GPN Response | $EC_{50}$ (μM) |
|---|---|---|---|
| 1 | 210150 | 70% | 6.0 |
| 2 | 210151 | 62% | 14.1 |
| 3 | 210154 | 175% | 5.3 |
| 4 | 210167 | 56% | 7.2 |
| 5 | 150262 | 72% | 2.1 |
| 6 | 260001 | 47% | 4.3 |
| 7 | 260002 | 70% | 5.4 |

TABLE 28-continued

Functional potency ($EC_{50}$) and % maximal change in the GPN induced calcium release in Gaucher patient cells of representative compounds of the disclosure.

Figure 3:
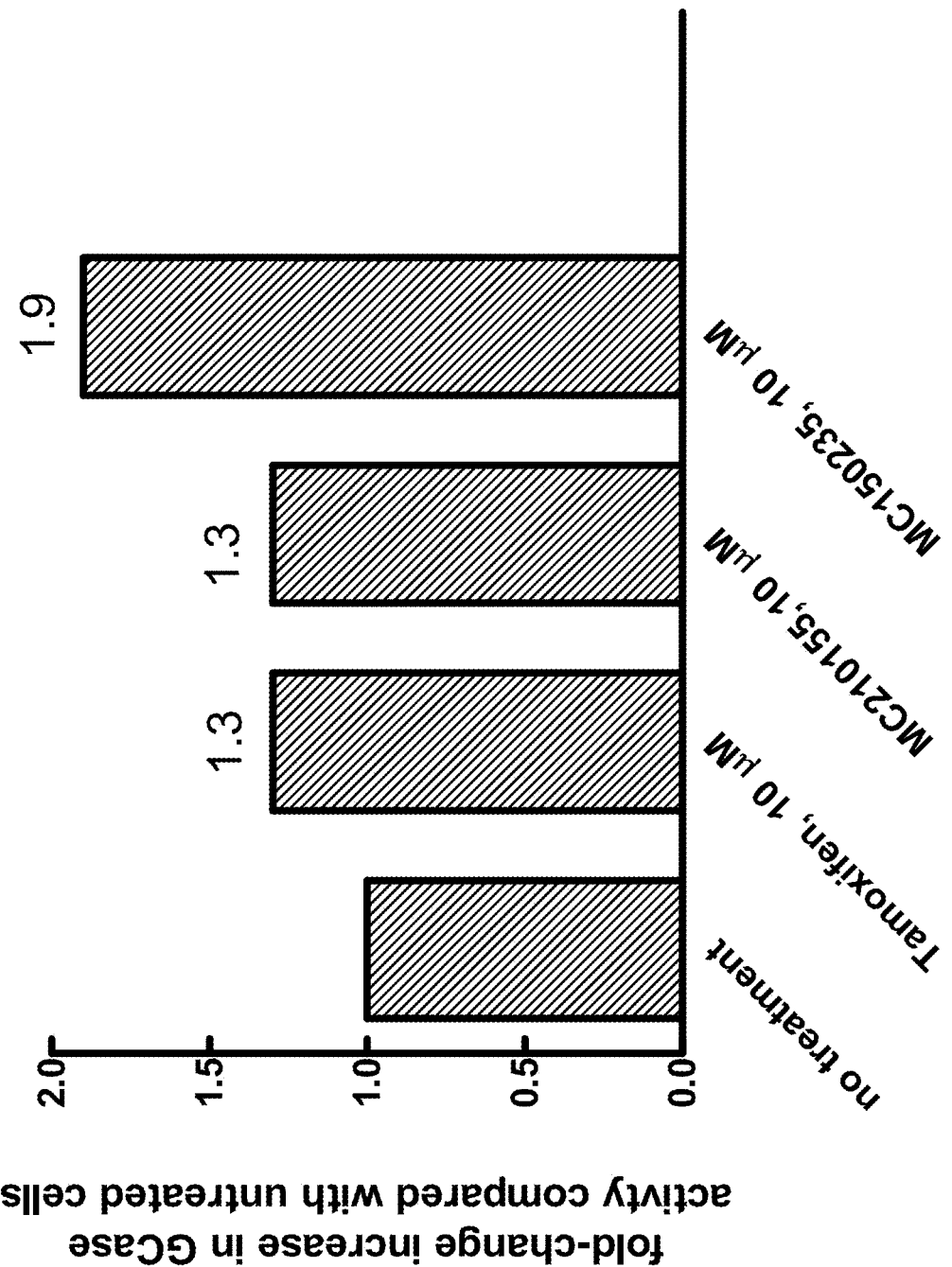
FIG. 3 is a chart depicting the increased β-Glucocerebrosidase (GCAse) activity measured from cell lysates prepared from Gaucher patient cells treated with tamoxifen or analogs after three day treatment. The fold-change increase in GCase activity relative to untreated cells is indicated where no change in activity=1.0.

| Example | MC-number | Maximal % Change in GPN Response | $EC_{50}$ (μM) |
|---|---|---|---|
| 8 | 210155 | 154% | 4.8 |
| 9 | 210163 | 53% | 3.0 |
| 10 | 210164 | 48% | 1.1 |
| 11 | 150224 | 54% | 3.3 |
| 12 | 150235 | 87% | 2.4 |
| 13 | 150268 | 191% | 1.5 |
| 14 | 150269 | 108% | 0.7 |
| 15 | 150279 | 217% | 2.7 |
| 16 | 150281 | 138% | 0.65 |
| 17 | 150278 | 275% | 2.2 |
| 18 | 150280 | 233% | 0.33 |

β-Glucocerebrosidase Activity Enhanced in Gaucher Patient Cells after Tamoxifen and synthesized analog treatment: Gaucher patient fibroblasts were cultured for 3 days in 10 μM final concentration tamoxifen, MC210155 or MC150235. Cellular lysates were prepared from compound treated cells and non-treated cells were included as a control. β-Glucocerebrosidase (GCase) activity was directly measured from lysates prepared from treated cells using a fluorescent substrate 4-methylumbelliferyl-β-D-glucopyranoside (MUG). Cells were washed 3× with phosphate-buffered saline (PBS) and detached by scraping. After centrifugation, The pellets were frozen on dry ice, thawed and lysed in McIlvaine (MI) buffer (100 mM sodium citrate, 200 mM sodium phosphate dibasic, 0.25% sodium taurocholate, and 0.1% Triton X-100, pH 5.2 containing protease inhibitors). Lysates are incubated with 3.0 mM 4-methylumbeliferryl-β-glucoside (4-MUG) substrate in MI buffer (50 μL) at 37° C. for 60 minutes. Reactions were stopped by addition of 0.4 M glycine, pH 10.6 (70 μL). Fluorescence was measured on a Clariostar plate reader (BMG Labtech) for one second per well using 355 nm excitation and 460 nm emission. Total protein was determined with the Bradford protein assay kit (BioRad) according to the manufacturer's instructions. The GCase activity measured after compound treatment is normalized to non-treated cells and expressed as relative activity where no change in GCAse activity is equal 1 (FIG. 3). Tamoxifen, MC210155, and MC150235 all produced an increase in GCase activity in Gaucher patient cells.

Antifungal activity assay to determine MIC and MFC: Antifungal activity of the compounds of the disclosure may be evaluated using USA standards, Clinical and Laboratory Standards Institute (CLSI) criteria. In brief, inocula from 24 hour *Candida* cultures on Sabouraud's dextore agar are standardized to a turbidity equivalent of 0.5 McFarland standards at 520 nm with a spectrophotometer. The suspensions are further diluted in Rosewell Park Memorial Institute (RPMI) 1640 medium (Life technologies, New York, USA) to yield an inoculum concentration of approximately 0.5 $1\times10^3$ to 2.5 $1\times10^3$ Cells/ml. Minimum inhibitory concentration (MIC) and minimum fungicidal concentration (MFC) assay are performed in 96-well plates and *Candida* species are exposed to a double dilution of compounds of the disclosure. Amphotericin B may be used as a positive control. All the experiments are preformed three times with duplicates. The pates are incubated at 35° C. for 48 hours to evaluate MIC.

Antifungal activity assay against biofilm: Antifungal activity of the compounds of the disclosure may be determined using sessile cells of an appropriate species. Isolates may be propagated in yeast peptone dextrose (YPD) medium (1% (wt/vol) yeast extract, 2% (wt/vol) peptone, 2% (wt/vol) dextrose). Flasks containing liquid medium (20 ml) may be inoculated with a loopful of cells from YPD agar plates containing freshly grown isolates and incubated overnight in an orbital shaker (100 rpm) at 30° C. Strains grow in the budding yeast phase under these conditions. Cells may be harvested and washed in sterile phosphate-buffered saline (PBS; 10 mM phosphate buffer, 2.7 mM potassium chloride, 137 mM sodium chloride (pH 7.4)). Cells may re-suspended in RPMI 1640 supplemented with 1-glutamine and buffered with morpholinepropanesulfonic acid to a cellular density equivalent to $1.0 \times 10^6$ cells per ml. Biofilms may be formed on commercially available presterilized, polystyrene, flat-bottom 96-well microtiter plates by pipetting standardized cell suspensions (100 of the $10^6$ cells/ml) into selected wells of the microtiter plate and incubating them for 48 hours at 37° C. After biofilm formation, the medium may be aspirated and non-adherent cells removed by thoroughly washing the biofilms three times in sterile PBS. Residual PBS may be removed by blotting with paper towels before the addition of compounds of the disclosure in serially double-diluted concentrations (1,024 to 1 g/ml and 32 to 0.125 g/ml, respectively, from stock solutions of each antifungal agent prepared in RPMI medium directly) and incubated for a further 48 h at 35° C. A series of antifungal agent-free wells and biofilm-free wells were also included to serve as positive and negative controls, respectively. Sessile MICs (SMICs) were determined at 50 and 80% inhibition $SMIC_{50}$ and $SMIC_{80}$, respectively) by using the XTT reduction assay.

XTT-reduction assay: A semiquantitative measure of biofilm formation are calculated by using an XTT [2,3-bis(2-methoxy-4-nitro-5-sulfo-phenyl)-2H-tetrazolium-5-carboxanilide]-reduction assay. Briefly, XTT is prepared in a saturated solution at 0.5 g/liter in Ringer's lactate. The solution is filter sterilized through a 0.22-μm-pore-size filter, aliquoted, and stored at −70° C. Prior to each assay, an aliquot of stock XTT is thawed, and menadione (10 mM prepared in acetone) is added to a final concentration of 1 μM. A 100-μl aliquot of the XTT-menadione solution is then added to each prewashed biofilm and to control wells (for the measurement of background XTT-reduction levels). The plates are incubated in the dark for 2 hours at 37° C. A colorimetric change in the XTT-reduction assay, a direct correlation of the metabolic activity of the biofilm, is then measured in a microtiter plate reader at 490 nm.

What is claimed is:

1. A compound having formula (I):

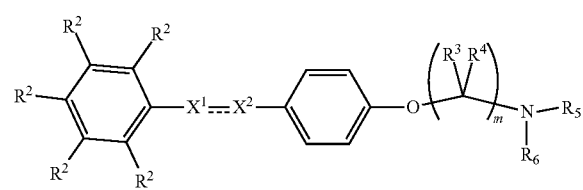

(I)

Including enantiomers, diastereomers, hydrates, solvates, pharmaceutically acceptable salts, prodrugs and complexes thereof, wherein:

the compound having the formula (I) is an N,N-dialkylamino phenyl ether compound, the bond between $X^1$ and $X^2$ is selected from a double bond and a single bond, when the bond between $X^1$ and $X^2$ is a single bond
  $X^1$ is $CHR^1$
  $X^2$ is selected from $CH_2$, $CHR^1$, and CO;
  $X^1$ and $X^2$ are not both $CH_2$, and $X^1$ and $X^2$ are not both $CHR^1$;

when the bond between $X^1$ and $X^2$ is a double bond
  $X^1$ is selected from CH and $CR^1$
  $X^2$ is selected from CH and $CR^1$
  $X^1$ and $X^2$ are not both CH, and $X^1$ and $X^2$ are not both $CR^1$;

$R^1$ is selected from the group consisting of $C_{1-10}$ linear alkyl, $C_{3-10}$ branched alkyl, $C_{3-10}$ cycloalkyl, $C_{1-10}$ linear alkenyl, $C_{3-10}$ branched alkenyl, $C_{1-10}$ linear alkynyl, and $C_{3-10}$ branched alkynyl;

$R^2$ is at each occurrence independently selected from the group consisting of H, OH, CN, $NO_2$, $C_{1-10}$ alkoxy, $C_{3-10}$ branched alkoxy, $C_{1-10}$ haloalkoxy, $C_{3-10}$ branched haloalkoxy, $NR^7R^8$, $C(O)OR^9$, $C_{1-10}$ thioalkyl, $C_{3-10}$ branched thioalkyl, $C_{1-10}$ halothioalkyl, —$S(O)C_{1-10}$ alkyl, —$S(O)C_{3-10}$ branched alkyl, —$S(O)C_{1-10}$ haloalkyl, —$S(O)C_{3-10}$ branched haloalkyl, —$SO_2C_{1-10}$ alkyl, —$SO_2C_{3-10}$ branched alkyl, —$SO_2C_{1-10}$ haloalkyl, —$SO_2C_{3-10}$ branched haloalkyl, $SO_2NR^{10}R^{11}$, —$NR^{10}SO_2R^{12}$, $C(O)$—$NR^{10}R^{11}$, wherein at least one instance of $R^2$ is not H;

$R^3$ is selected from the group consisting of hydrogen, $C_{1-6}$ linear alkyl, $C_{3-7}$ branched alkyl;

$R^4$ is selected from the group consisting of hydrogen, $C_{1-6}$ linear alkyl, $C_{3-7}$ branched alkyl;

m is 2, 3, 4, 5, 6, 7, 8, 9, or 10;

$R^5$ is selected from the group consisting of methyl, $C_{3-6}$ linear alkyl, and $C_{3-7}$ branched alkyl;

$R^6$ is selected from the group consisting of methyl, $C_{3-6}$ linear alkyl, and $C_{3-7}$ branched alkyl;

In some embodiments, $R^5$ and $R^6$ are taken together with the atoms to which they are bound to form a ring containing 4 to 7 members, optionally containing a member selected from the group consisting of O, S, and $NR^{13}$;

$R^7$ is at each occurrence independently selected from the group consisting of hydrogen, $C_{1-6}$ linear alkyl, $C_{3-7}$ branched alkyl;

$R^8$ is at each occurrence independently selected from the group consisting of hydrogen, $C_{1-6}$ linear alkyl, $C_{3-7}$ branched alkyl;

$R^9$ is at each occurrence independently selected from the group consisting of hydrogen, $C_{1-6}$ linear alkyl, $C_{3-7}$ branched alkyl;

$R^{10}$ is at each occurrence independently selected from the group consisting of hydrogen, $C_{1-6}$ linear alkyl, $C_{3-7}$ branched alkyl;

$R^{11}$ is at each occurrence independently selected from the group consisting of hydrogen, $C_{1-6}$ linear alkyl, $C_{3-7}$ branched alkyl;

$R^{12}$ is at each occurrence independently selected from the group consisting of hydrogen, $C_{1-6}$ linear alkyl, $C_{3-7}$ branched alkyl;

$R^{13}$ is at each occurrence independently selected from the group consisting of hydrogen, $C_{1-6}$ linear alkyl, $C_{3-7}$ branched alkyl; and the pharmaceutically acceptable salts are formed using bases or acids selected from the group consisting of acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, isethionic, maleic, malic, malonic, mandelic, methanesulfonic, mucic, napthalenesulfonic, nitric, oxalic, pamoic, pantothenic, phosphoric, phthalic, succinic, sulfuric, toluenesulfonic, and any combination thereof;

wherein the following compounds are specifically excluded from the scope of the markush:

1-[4-[3-(diethylamino)propoxy]phenyl]-2-phenyl-1-Propanone;
1-[4-[2-(diethylamino)ethoxy]phenyl]-2-phenyl-1-pentanone;
2-phenyl-1-[4-[2-(1-piperidinyl)ethoxy]phenyl]-1-Butanone;
1-[4-[2-(dimethylamino)ethoxy]phenyl]-2-phenyl-1-Butanone;
2-(4-aminophenyl)-1-[4-[2-(1-pyrrolidinyl)ethoxy]phenyl]-1-Butanone;
2-(4-nitrophenyl)-1-[4-[2-(1-pyrrolidinyl)ethoxy]phenyl]-1-Butanone;
1-[4-[2-(dimethylamino)ethoxy]phenyl]-2-[4-(1-methylethyl)phenyl]-1-Butanone;
4'-(2-diethylaminoethoxy)-2-phenylButyrophenone;
2-(4-bromophenyl)-1-[4-[2-(dimethylamino)ethoxy]phenyl]-1-Butanone;
1-[3,5-dibromo-4-[2-(dimethylamino)ethoxy]phenyl]-2-phenyl-1-Butanone;
2-(4-bromophenyl)-1-[4-[2-(dimethylamino)ethoxy]phenyl]-1-Butanone;
1-[4-[[6-(dimethylamino)hexyl]oxy]phenyl]-2-phenyl-1-Butanone;
1-[4-[2-(dimethylamino)ethoxy]phenyl]-2-(4-ethylphenyl)-1-Butanone;
1-[4-[2-(dimethylamino)ethoxy]phenyl]-2-(4-fluorophenyl)-1-Butanone;
1-[4-[3-(diethylamino)propoxy]phenyl]-2-phenyl-1-Butanone;
1-[4-[[5-(dimethylamino)pentyl]oxy]phenyl]-2-phenyl-1-Butanone;
2-phenyl-1-[4-[2-(1-pyrrolidinyl)ethoxy]phenyl]-1-Butanone;
1-[4-[4-(dimethylamino)butoxy]phenyl]-2-phenyl-1-Butanone;
1-[4-[2-(dimethylamino)ethoxy]phenyl]-2-(4-methylphenyl)-1-Butanone;
1-[4-[2-(diethylamino)ethoxy]phenyl]-3-methyl-2-phenyl-1-Butanone;
1-[4-[2-(diethylamino)ethoxy]phenyl]-2-phenyl-1-Butanone;
1-[4-[2-(dimethylamino)ethoxy]phenyl]-2-phenyl-1-Butanone;
4'-(2-morpholinoethoxy)-2-phenyl-Butyrophenone;
1-[4-[2-(dimethylamino)ethoxy]phenyl]-2-phenyl-1-Propanone;
2-cyclohexyl-1-[3,5-dimethyl-4-[2-(4-morpholinyl)ethoxy]phenyl]-2-phenyl-Ethanone;
N,N-dimethyl-2-[4-[(1Z)-2-phenyl-1-buten-1-yl]phenoxy]-Ethanamine;
N,N-diethyl-2-[4-[2-(4-methoxyphenyl)-1-propen-1-yl]phenoxy]-Ethanamine;
4-[(1E)-2-[4-[2-(diethylamino)ethoxy]phenyl]-1-methylethenyl]-Phenol;
4-[2-[4-[2-(diethylamino)ethoxy]phenyl]-1-methylethenyl]-Phenol;
2-[p-(p-methoxy-b-methylstyryl)phenoxy]-Triethylamine;
N,N-diethyl-3-[4-(1-methyl-2-phenylethenyl)phenoxy]-1-Propanamine;
N,N-diethyl-2-[4-[1-(phenylmethylene)propyl]phenoxy]-Ethanamine;
N,N-diethyl-2-[4-(1-methyl-2-phenylethenyl)phenoxy]-Ethanamine;
2-[p-(p-methoxy-a-methylstyryl)phenoxy]-Triethylamine;
4'-[2-(diethylamino)ethoxy]-a'-methyl-4-Stilbenol;
(E)-1-[2-[4-(1-cyclopentyl-2-phenylethenyl)phenoxy]ethyl]-Pyrrolidine;
(Z)-1-[2-[4-(1-cyclopentyl-2-phenylethenyl)phenoxy]ethyl]-Pyrrolidine;
2-[4-[1-cyclohexyl-2-(4-methoxyphenyl)ethenyl]phenoxy]-N,N-diethyl-Ethanamine;
N,N-diethyl-2-[4-[2-(4-methoxyphenyl)propyl]phenoxy]-Ethanamine;
4-[2-[4-[2-(diethylamino)ethoxy]phenyl]-1-methylethyl]-Phenol;
N,N-diethyl-3-[4-(1-methyl-2-phenylethyl)phenoxy]-1-Propanamine;
N,N-diethyl-2-[4-(1-methyl-2-phenylethyl)phenoxy]-Ethanamine;
N,N-diethyl-2-[4-[1-[(4-methoxyphenyl)methyl]propyl]phenoxy]-Ethanamine;
N,N-diethyl-2-[4-[2-(4-methoxyphenyl)-1-methylethyl]phenoxy]-Ethanamine;
4-[2-[4-[2-(diethylamino)ethoxy]phenyl]propyl]-Phenol; and 2-[4-[1-cyclohexyl-2-(4-methoxyphenyl)ethyl]phenoxy]-N,N-diethyl-Ethanamine.

2. The compound of claim 1, wherein the compound of formula (I) is a compound of formula (II), formula (VIII), formula (XI), formula (XIV), formula (XVII), or formula (XX):

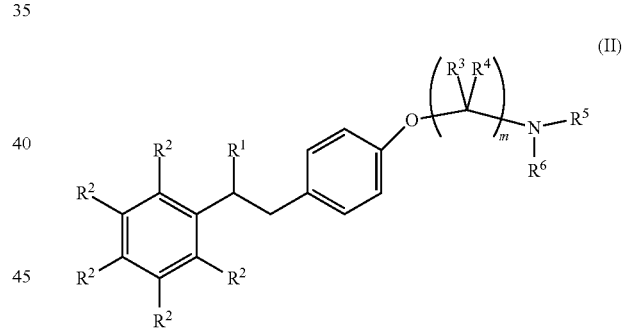

(II)

Including enantiomers, diastereomers, hydrates, solvates, pharmaceutically acceptable salts, prodrugs and complexes thereof;

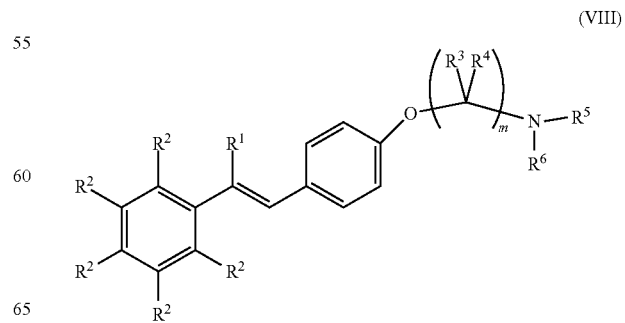

(VIII)

Including enantiomers, diastereomers, hydrates, solvates, pharmaceutically acceptable salts, prodrugs and complexes thereof,

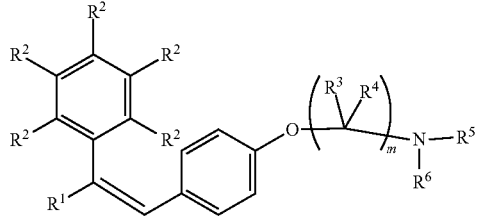
(XI)

Including enantiomers, diastereomers, hydrates, solvates, pharmaceutically acceptable salts, prodrugs and complexes thereof;

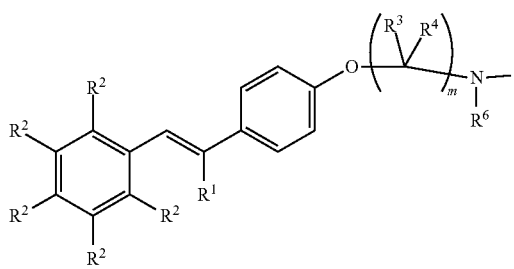
(XIV)

Including enantiomers, diastereomers, hydrates, solvates, pharmaceutically acceptable salts, prodrugs and complexes thereof;

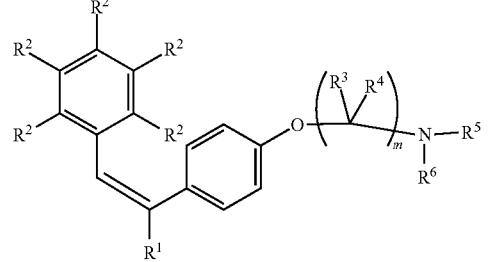
(XVII)

Including enantiomers, diastereomers, hydrates, solvates, pharmaceutically acceptable salts, prodrugs and complexes thereof;

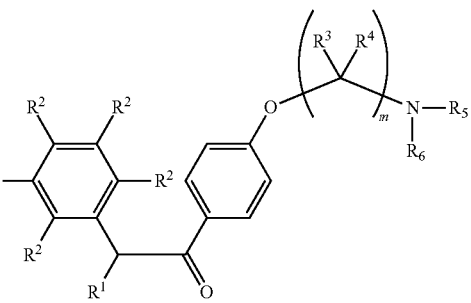
(XX)

Including enantiomers, diastereomers, hydrates, solvates, pharmaceutically acceptable salts, prodrugs and complexes thereof.

3. The compound of claim 1, wherein the compound of formula (I) is a compound of formula (III), formula (IV), formula (IX), formula (X), formula (XII), formula (XIII), formula (XV), formula (XVI), formula (XVIII), formula (XIX), formula (XXI), or formula (XXII):

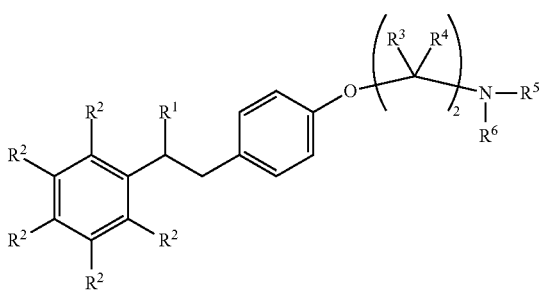
(III)

Including enantiomers, diastereomers, hydrates, solvates, pharmaceutically acceptable salts, prodrugs and complexes thereof;

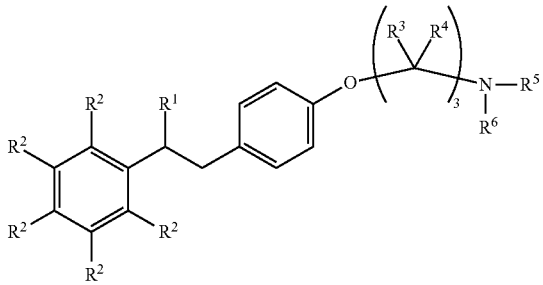
(IV)

Including enantiomers, diastereomers, hydrates, solvates, pharmaceutically acceptable salts, prodrugs and complexes thereof;

(IX)

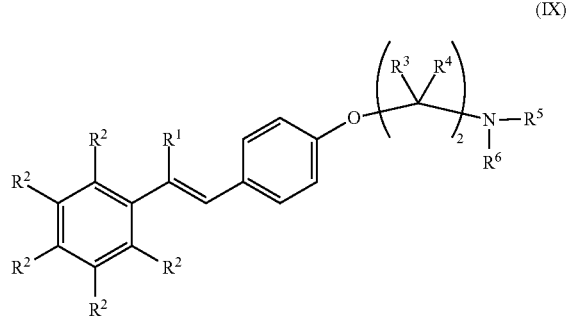

Including enantiomers, diastereomers, hydrates, solvates, pharmaceutically acceptable salts, prodrugs and complexes thereof;

(X)

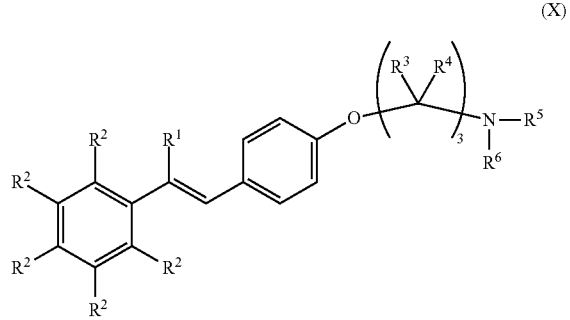

Including enantiomers, diastereomers, hydrates, solvates, pharmaceutically acceptable salts, prodrugs and complexes thereof;

(XII)

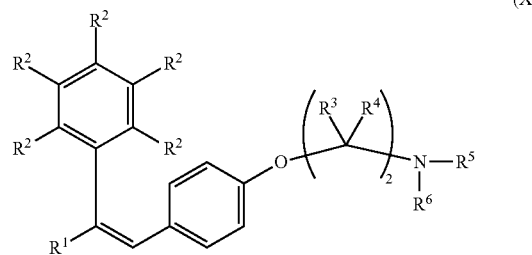

Including enantiomers, diastereomers, hydrates, solvates, pharmaceutically acceptable salts, prodrugs and complexes thereof;

(XIII)

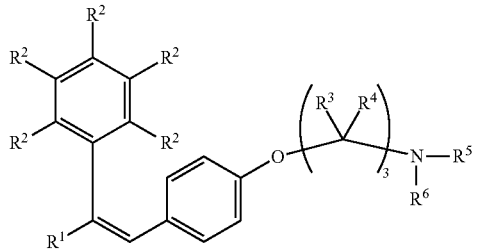

Including enantiomers, diastereomers, hydrates, solvates, pharmaceutically acceptable salts, prodrugs and complexes thereof;

(XV)

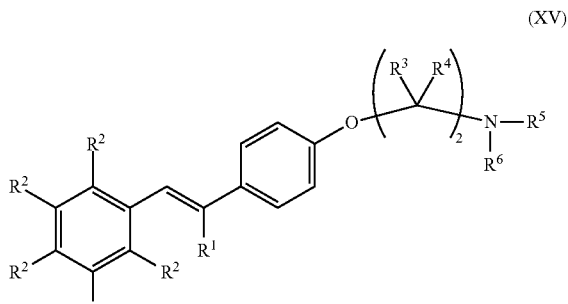

Including enantiomers, diastereomers, hydrates, solvates, pharmaceutically acceptable salts, prodrugs and complexes thereof;

(XVI)

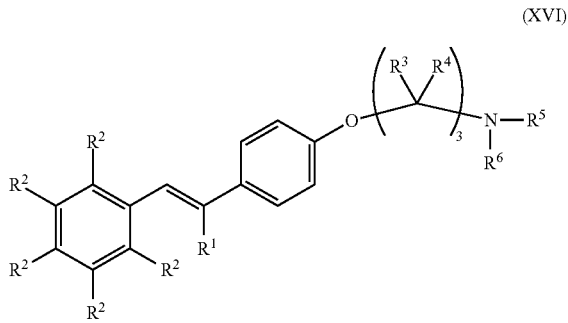

Including enantiomers, diastereomers, hydrates, solvates, pharmaceutically acceptable salts, prodrugs and complexes thereof;

(XVIII)

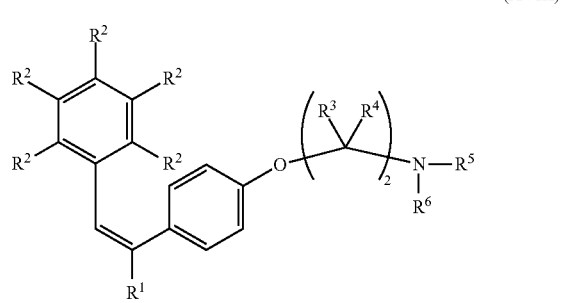

Including enantiomers, diastereomers, hydrates, solvates, pharmaceutically acceptable salts, prodrugs and complexes thereof;

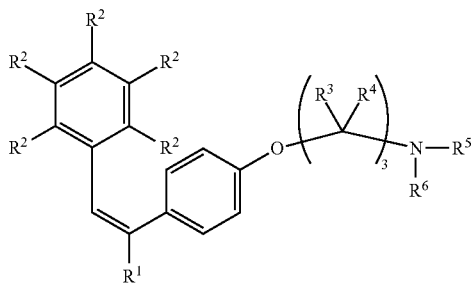

(XIX)

Including enantiomers, diastereomers, hydrates, solvates, pharmaceutically acceptable salts, prodrugs and complexes thereof;

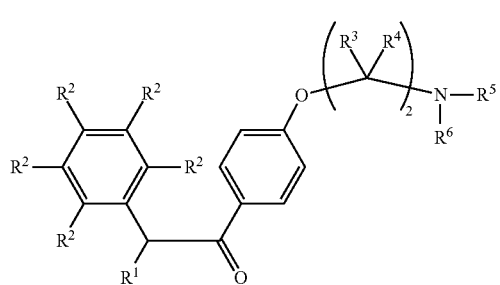

(XXI)

Including enantiomers, diastereomers, hydrates, solvates, pharmaceutically acceptable salts, prodrugs and complexes thereof;

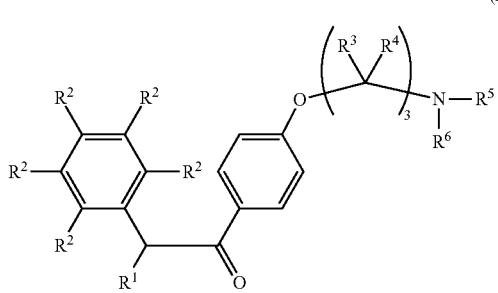

(XXII)

Including enantiomers, diastereomers, hydrates, solvates, pharmaceutically acceptable salts, prodrugs and complexes thereof.

4. A composition comprising at least one compound according to claim 1 and at least one excipient.

5. A method for treating or preventing a disease or conditions that involve lysosomal storage dysfunction, said method comprising administering to a subject an effective amount of at least one compound according to claim 1.

6. The method of claim 5 wherein the disease or conditions that involve lysosomal storage dysfunction is Gaucher's disease, Tay-Sachs disease, Sandhoff's disease, Sandhoff-Jatzkewitz disease, Fabry disease, Niemann Pick disease Type C, Pompe disease, type III A mucopolysaccharidosis, Sanfilippo syndrome, α-mannosidosis, GM1 gangliosidosis, or GM2 gangliosidosis.

7. The method of claim 5, wherein the at least one compound is administered in a composition further comprising at least one excipient.

8. A method of treating or preventing a fungal infection, said method comprising administering to a subject an effective amount of at least one compound according to claim 1.

9. The method of claim 8, wherein the at least one compound is administered in a composition further comprising at least one excipient.

10. A method of treating or preventing Parkinson's disease, said method comprising administering to a subject an effective amount of at least one compound according to claim 1.

11. The method of claim 10, wherein the at least one compound is administered in a composition further comprising at least one excipient.

12. A method of treating synucleinopathies such as dementia with Lewy bodies (DLB), pure autonomic failure (PAF), and multiple system atrophy (MSA), said method comprising administering to a subject an effective amount of at least one compound according to claim 1.

13. The method of claim 12, wherein the at least one compound is administered in a composition further comprising at least one excipient.

* * * * *